(12) United States Patent
Grandien et al.

(10) Patent No.: US 7,319,024 B1
(45) Date of Patent: Jan. 15, 2008

(54) C. ELEGANS P21-ACTIVATED KINASE (PAK) GENE AND ASSOCIATED LOSS-OF-FUNCTION PHENOTYPES THAT FACILITATE SCREENING FOR SMALL MOLECULE MODULATORS OF PAK ACTIVITY IN THE NEMATODE, CAENORHABDITIS ELEGANS

(75) Inventors: Kaj Grandien, Kelkheim (DE); Jonathan Rothblatt, Somerville, MA (US); Paola Concari, Munich (DE); Isabelle Quelo, Schwalbach (DE); Bert Klebl, Gunzlhofen (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 229 days.

(21) Appl. No.: 11/045,439

(22) Filed: Jan. 28, 2005

Related U.S. Application Data

(60) Provisional application No. 60/580,275, filed on Jun. 16, 2004.

(30) Foreign Application Priority Data

Jan. 28, 2004 (EP) ................................ 04001748

(51) Int. Cl.
*C12P 19/34* (2006.01)
*C12N 1/20* (2006.01)
*C12N 15/00* (2006.01)
*C07H 21/04* (2006.01)

(52) U.S. Cl. .............................. 435/91.3; 435/252.33; 435/325; 435/320.1; 536/23.2; 536/23.5

(58) Field of Classification Search ................. None
See application file for complete search history.

(56) References Cited

OTHER PUBLICATIONS

Database: GENBANK, Accession No. AL032639 (May 14, 2001).*
Reboul et al. Database: EST, Accession No. CB392803/c (May 15, 2003).*
Reboul et al. Database: EST, Accession No. CB388866 (May 15, 2003).*
Kohara et al. Database: EST, Accession No. BJ120228 (Jan. 23, 2002).*
Kohara et al. Database: EST, Accession No. BJ101260 (Jan. 18, 2002).*
Bokoch, G.M., Biology of the p21—Activated Kinases, Annu. Rev. Biochem, Vol. 72, 2003, pp. 743-781.
Chen et al., The Caenorhabditis elgans p21-activated Kinase (CePAK) Colocalizes with CeRacl and CDC42Ce at Hypodermal Cell Boundaries during Embryo Elongation, Journ. of Biological Chemistry, vol. 271, No. 42, Oct. 18, 1996, pp. 26362-26368.
Fire et al., Potent and specific genetic interference by double-stranded RNA in Caenorhabditis elegans, Nature, vol. 391, Feb. 19, 1998, pp. 806-811.
Iino et al., Expression Pattern of the C. elegans p21-Activated Protein Kinase, CePAK, Biochemical and Biophysical Res. Commu. vol. 245, 1998, pp. 177-184.
Kamath et al., Effectiveness of specific RNA-mediated interference through ingested double-stranded RNA in Caenorhabditis elegans, Genome Biology, vol. 2, 2000, research0002.1-0002.10.
Maeda et al., Large-scale analysis of gene function in Caenorhabditis elegans by high-throughput RNAI, Current Biology, vol. 11, No. 3, 2000, pp. 171-176.
Nishiwaki K., Mutations Affecting Symmetrical Migration of Distal Tip Cells in Caenorhabditis elegans, Genetics, vol. 152, Jul. 1999, pp. 985-997.
Reddien et al., CED-2/Crkll and CED-10/Rac control phagocytosis and cell migration in Caenorhabditis elegans, Nature Cell Biology, vol. 2, Mar. 2000, pp. 131-136.
Schlotterer et al., M13mtvh: an imporved M13 vector for rapid and simple cloning of PCR products, Trends in Genetics, vol. 12, 1996, pp. 286-287.
Su et al., Regulation of the UNC-5 netrin receptor initiates the first reorientation of migrating distal tip cells in Caenorhabditis elegans, Development, vol. 127, 2000, pp. 585-594.
Sulston et al., Post-embryonic Cell Lineages of the Nematode Caenorhabdiis elegans, Developmental Biology, vol. 56, 1977, pp. 110-156.
Tavernarakis et al., Heritable and inducible genetic interference by double-stranded RNA encoded transgenes, Nature genetics, vol. 24, Feb. 2000, pp. 180-183.
Timmons et al., Ingestion of bacterially expressed dsRNAs can produce specific and potent genetic interference in Caenorhabditis elegans, Gene, vol. 263, 20001, pp. 103-112.
Bishop et al., Rho GTPases and their effector proteins, Biochem J. vol. 348, 2000, pp. 241-255.

* cited by examiner

*Primary Examiner*—Nashaat T. Nashed

(57) ABSTRACT

The invention refers to a novel *C. elegans* p21-activated kinase gene, the pak-3 gene, and associated loss-of-function phenotypes. These phenotypes can be used to elucidate PAK signaling pathways in *C. elegans* and to screen compounds that modulate PAK signaling.

7 Claims, 38 Drawing Sheets

Fig. 1:

>pKG40\ORF\pak-3a\WT
atgtttcaaaatagtccgatgatgtacgactggtggaatgacaccaccaaaccgaaacaccagcagccga
cacttaacgtgttgtcaccatggggagcatatttcaatcacattggaaatgaactgctgcatctgaaaat
cgcatcgtcgacagtatcctcgggatgctcgtctccacaacagtattcgtctgctcgatccgttggtaac
tcgctctccaacggcagtgttgtctccacaacatcgtcagatggtgatgtgcaattgtcgaataaggaaa
attcgaatgacaaatcagttggagacaagaatgggaacaccaccacaaacaaaacgaccgtcgaaccacc
tccaccagaagagccacctgttcgtgttcgagcatctcatcgtgaaaagctttctgattccgaagtgctc
aatcaactccgcgagattgttaatccaagtaatccacttggaaagtacgagatgaagaagcaaatcggtg
ttggagcatccggaactgtattcgttgctaatgtggccggcagcactgatgtggtggctgtgaagagaat
ggctttcaagactcagccgaagaaggagatgttgctcaccgagattaaggttatgaagcagtatcgacac
ccgaacctcgtcaactacattgaatcgtatctggttgatgctgatgatctttgggtagtgatggattatc
tggaaggtggaaacttgacagatgtcgttgtgaagactgagttggacgaaggacaaattgcagcagtttt
gcaagaatgtcttaaagcgcttcacttccttcatagacactccatagtgcaccgagatatcaagagtgac
aacgtgctgctcggcatgaacggagaggttaagctcaccgatatgggattctgtgctcagattcagccgg
gatcgaaaagagatactgtcgtcggaactccatattggatgtcgccggagatattgaacaagaagcagta
caactataaggttgacatttggtcgctgggaattatggctctagagatgattgatggagagccaccatat
ttgagagaaacacctttgaaggctatctacttgattgctcaaaacgggaagccagagatcaagcaacgcg
acagactgtcttcagagttcaacaatttccttgacaagtgtcttgttgttgatccggatcagagagccga
tacaacggagctcttggcacatccattcctgaaaaaggcgaagccactctcaagcctgattccatacatc
agagccgtccgagaaaagtag

Fig. 2:

>pKG123\ORF\pak-3b\WT\v1
atgtcaacttcaaaaagttccaaggtgcgaatacggaatttcatcgggcgaatcttctctcccagcgata
aagacaaggatcgagacgatgagatgaagccatcctcgtccgcaatggatattagtcagccatataacac
agtgcatcgagtccacgttggatacgacggccagaagttcagcggactgccgcaaccatggatggatatt
cttctccgagacattagtcttgccgatcagaagaaggatccgaacgcggtggtgactgcgttgaagttct
acgcacaatcaatgaaggagaacgagaagacgaaattcatgacgacgaatagtgttttcacgaatagcga
tgacgatgatgtggacgttcagttgaccggacaagtcacggaacatttgaggaatttgcagtgtagtaat
ggttccgcaacttccccatctacatcagtgtcagcttcatcttcttctgctcgtccactgacaaatggaa
ataatcatctttccacggcgtcgtctaccgacacatctctctcattatcggaaggaataacgttccgtc
tccagctccagttccatatagtgaaagtgctccacaactgaaaacattcaccggagagactccaaaactg
catccacgatctccgttcccgcctcaaccgccagttcttccgcaacgaagcaaaaccgcatcggcagtgg
cgacgacgacgacgaatccgacgacttcgaatggagcaccaccaccagttcctggatcgaaaggaccccc
ggtgccaccgaaaccatcgcatctgaaaatcgcatcgtcgacagtatcctcgggatgctcgtctccacaa
cagtattcgtctgctcgatccgttggtaactcgctctccaacggcagtgttgtctccacaacatcgtcag
atggtgatgtgcaattgtcgaataaggaaaattcgaatgacaaatcagttggagacaagaatgggaacac
caccacaaacaaaacgaccgtcgaaccacctccaccagaagagccacctgttcgtgttcgagcatctcat
cgtgaaaagctttctgattccgaagtgctcaatcaactccgcgagattgttaatccaagtaatccacttg
gaaagtacgagatgaagaagcaaatcggtgttggagcatccggaactgtattcgttgctaatgtggccgg
cagcactgatgtggtggctgtgaagagaatggctttcaagactcagccgaagaaggagatgttgctcacc
gagattaaggttatgaagcagtatcgacacccgaacctcgtcaactacattgaatcgtatctggttgatg
ctgatgatctttgggtagtgatggattatctggaaggtggaaacttgacagatgtcgttgtgaagactga
gttggacgaaggacaaattgcagcagttttgcaagaatgtcttaaagcgcttcacttccttcatagacac
tccatagtgcaccgagatatcaagagtgacaacgtgctgctcggcatgaacggagaggttaagctcaccg
atatgggattctgtgctcagattcagccgggatcgaaaagagatactgtcgtcggaactccatattggat
gtcgccggagatattgaacaagaagcagtacaactataaggttgacatttggtcgctgggaattatggct
ctagagatgattgatggagagccaccatatttgagagaaacacctttgaaggctatctacttgattgctc
aaaacgggaagccagagatcaagcaacgcgacagactgtcttcagagttcaacaatttccttgacaagtg
tcttgttgttgatccggatcagagagccgatacaacggagctcttggcacatccattcctgaaaaaggcg
aagccactctcaagcctgattccatacatcagagccgtccgagaaaagtag

Fig. 3:

```
>pKG43\ORF\pak-3b\v2
atgtcaacttcaaaaagttccaaggtgcgaatacggaatttcatcgggcgaatcttctctcccagcgata
aagacaaggatcgagacgatgagatgaagccatcctcgtccgcaatggatattagtcagccatataacac
agtgcatcgagtccacgttggatacgacggccagaagttcagcggactgccgcaaccatggatggatatt
cttctccgagacattagtcttgccgatcagaagaaggatccgaacgcggtggtgactgcgttgaagttct
acgcacaatcaatgaaggagaacgagaagacgaaattcatgacgacgaatagtgttttcacgaatagcga
tgacgatgatgtggacgttcagttgaccggacaagtcacggaacatttgaggaatttgcagtgtagtaat
ggttccgcaacttccccatctacatcagtgtcagcttcatcttcttctgctcgtccactgacaaatggaa
ataatcatctttccacggcgtcgtctaccgacacatctctctcattatcggaaaggaataacgttccgtc
tccagctccagttccatatagtgaaagtgctccacaactgaaaacattcaccggagagactccaaaactg
catccacgatctccgttcccgcctcaaccgccagttcttccgcaacgaagcaaaaccgcatcggcagtgg
cgacgacgacgacgaatccgacgacttcgaatggagcaccaccaccagttcctggatcgaaaggacccc
ggtgccaccgaaaccatcgcatctgaaaatcgcatcgtcgacagtatcctcgggatgctcgtctccacaa
cagtattcgtctgctcgatccgttggtaactcgctctccaacggcagtgttgtctccacaacatcgtcag
atggtgatgtgcaattgtcgaataaggaaaattcgaatgacaaatcagttggagacaagaatgggaacac
caccacaaacaaaacgaccgtcgaaccacctccaccagaagagccacctgttcgtgttcgagcatctcat
cgtgaaaagctttctgattccgaagtgctcaatcaactccgcgagattgttaatccaagtaatccacttg
gaaagtacgagatgaagaagcaaatcggtgttggagcatccggaactgtattcgttgctaatgtggccgg
cagcactgatgtggtggctgtgaagagaatggctttcaagactcagccgaagaaggagatgttgctcacc
gagattaaggttatgaagcagtatcgacacccgaacctcgtcaactacattgaatcgtatctggttgatg
ctgatgatctttgggtagtgatggattatctggaaggtggaaacttgacagatgtcgttgtgaagactga
gttggacgaaggacaaattgcagcagttttgcaagaatgtcttaaagcgcttcacttccttcatagacac
tccatagtgcaccgagatatcaagagtgacaacgtgctgctcggcatgaacggagaggttaagctcaccg
atatgggattctgtgctcagattcagccgggatcgaaaagagatactgtcgtcggaactccatattggat
gtcgccggagatattgaacaagaagcagtacaactataaggttgacatttggtcgctgggaattatggcc
ctagagatgattgatggagagccaccatatttgagagaaacacctttgaaggctatctacttgattgctc
aaaacgggaagccagagatcaagcaacgcgacagactgtcttcagagttcaacaatttccttgacaagtg
tcttgttgttgatccggatcagagagccgatacaacggagctcttggcacatccattcctgaaaaaggcg
aagccactctcaagcctgattccatacatcagagccgtccgagaaaagtag
```

Fig. 4:

>pKG44\ORF\pak-3b\v3
```
atgtcaacttcaaaaagttccaaggtgcgaatacggaatttcatcgggcgaatcttctctcccagcgata
aagacaaggatcgagacgatgagatgaagccatcctcgtccgcaatggatattagtcagccatataacac
agtgcatcgagtccacgttggatacgacggccagaagttcagcggactgccgcaaccatggatggatatt
cttctccgagacattagtcttgccgatcagaagaaggatccgaacgcggtggtgactgcgttgaagttct
acgcacaatcaatgaaggagaacgagaagacgaaattcatgacgacgaatagtgttttcacgaatagcga
tgacgatgatgtggacgttcagttgaccggacaagtcacggaacatttgaggaatttgcagtgtagtaat
ggttccgcaacttccccatctacatcagtgtcagcttcatcttcttctgctcgtccactgacaaatggaa
ataatcatctttccacggcgtcgtctaccgacacatctctctcattatcggaaaggaataacgttccgtc
tccagctccagttccatatagtgaaagtgctccacaactgaaaacattcaccggagagactccaaaactg
catccacgatctccgttcccgcctcaaccgccagttcttccgcaacgaagcaaaaccgcatcggcagtgg
cgacgacgacgacgaatccgacgacttcgaatggagcaccaccaccagttcctggatcgaaaggaccccc
ggtgccaccgaaaccatcgcatctgaaaatcgcatcgtcgacagtatcctcgggatgctcgtctccacaa
cagtattcgtctgctcgatccgttggtaactcgctctccaacggcagtgttgtctccacaacatcgtcag
atggtgatgtgcaattgtcgaataaggaaaattcgaatgacaaatcagttggagacaagaatgggaacac
caccacaaacaaaacgaccgtcgaaccacctccaccagaagagccacctgttcgtgttcgagcatctcat
cgtgaaaagctttctgattccgaagtgctcaatcaactccgcgagattgttaatccaagtaatccacttg
gaaagtacgagatgaagaagcaaatcggtgttggagcatccggaactgtattcgttgctaatgtggccgg
cagcactgatgtggtggctgtgaagagaatggctttcaagactcagccgaagaaggagatgttgctcacc
gagattaaggttatgaagcagtatcgacacccgaacctcgtcaactacattgaatcgtatctggttgatg
ctgatgatctttgggtagtgatggattatctggaaggtggaaacttgacagatgtcgttgtgaagactga
gttggacgaaggacaaattgcagcagttttgcaagaatgtcttaaagcgcttcacttccttcatagacac
tccatagtgcaccgagatatcaagagtgacaacgtgctgctcggcatgaacggagaggttaagctcaccg
atatgggattctgtgctcagattcagccgggatcgaaaagttgtagagatactgtcgtcggaactccata
ttggatgtcgccggagatattgaacaagaagcagtacaactataaggttgacatttggtcgctgggaatt
atggccctagagatgattgatggagagccaccatatttgagagaaacacctttgaaggctatctacttga
ttgctcaaaacgggaagccagagatcaagcaacgcgacagactgtcttcagagttcaacaatttccttga
caagtgtcttgttgttgatccggatcagagagccgatacaacggagctcttggcacatccattcctgaaa
aaggcgaagccactctcaagcctgattccatacatcagagccgtccgagaaaagtag
```

Fig. 5:

```
>pKG58\ORF\pak-3b\v4
atgtcaacttcaaaaaagttccaaggtgcgaatacggaatttcatcgggcgaatcttctctcccagcgata
aagacaaggatcgagacgatgagatgaagccatcctcgtccgcaatggatattagtcagccatataacac
agtgcatcgagtccacgttggatacgacggccagaagttcagcggactgccgcaaccatggatggatatt
cttctccgagacattagctatttcagtcttgccgatcagaagaaggatccgaacgcggtggtgactgcgt
tgaagttctacgcacaatcaatgaaggagaacgagaagacgaaattcatgacgacgaatagtgttttcac
gaatagcgatgacgatgatgtggacgttcagttgaccggacaagtcacggaacatttgaggaatttgcag
tgtagtaatggttccgcaacttccccatctacatcagtgtcagcttcatcttcttctgctcgtccactga
caaatggaaataatcatctttccacggcgtcgtctaccgacacatctctctcattatcggaaaggaataa
cgttccgtctccagctccagttccatatagtgaaagtgctccacaactgaaaacattcaccggagagact
ccaaaactgcatccacgatctccgttcccgcctcaaccgccagttcttccgcaacgaagcaaaaccgcat
cggcagtggcgacgacgacgacgaatccgacgacttcgaatggagcaccaccaccagttcctggatcgaa
aggaccccggtgccaccgaaaccatcgaaggaaaattcgaatgacaaatcagttggagacaagaatggg
aacaccaccacaaacaaaacgaccgtcgaaccacctccaccagaagagccacctgttcgtgttcgagcat
ctcatcgtgaaaagctttctgattccgaagtgctcaatcaactccgcgagattgttaatccaagtaatcc
acttggaaagtacgagatgaagaagcaaatcggtgttggagcatccggaactgtattcgttgctaatgtg
gccggcagcactgatgtggtggctgtgaagagaatggctttcaagactcagccgaagaaggagatgttgc
tcaccgagattaaggttatgaagcagtatcgacacccgaacctcgtcaactacattgaatcgtatctggt
tgatgctgatgatcttttgggtagtgatggattatctggaaggtggaaacttgacagatgtcgttgtgaag
actgagttggacgaaggacaaattgcagcagttttgcaagaatgtcttaaagcgcttcacttccttcata
gacactccatagtgcaccgagatatcaagagtgacaacgtgctgctcggcatgaacggagaggttaagct
caccgatatgggattctgtgctcagattcagccgggatcgaaaagagatactgtcgtcggaactccatat
tggatgtcgccggagatattgaacaagaagcagtacaactataaggttgacatttggtcgctgggaatta
tggctctagagatgattgatggagagccaccatatttgagagaaacacctttgaaggctatctacttgat
tgctcaaaacgggaagccagagatcaagcaacgcgacagactgtcttcagagttcaacaatttccttgac
aagtgtcttgttgttgatccggatcagagagccgatacaacggagctcttggcacatccattcctgaaaa
aggcgaagccactctcaagcctgattccatacatcagagccgtccgagaaaagtag
```

Fig. 6:

>pKG59\ORF\pak-3b\v5
atgtcaacttcaaaaagttccaaggtgcgaatacggaatttcgtcgggcgaatcttctctcccagcgata
aagacaaggatcgagacgatgagatgaagccatcctcgtccgcaatggatattagtcagccatataacac
agtgcatcgagtccacgttggatacgacggccagaagttcagcggactgccgcaaccatggatggatatt
cttctccgagacattagtcttgccgatcagaagaaggatccgaacgcggtggtgactgcgttgaagttct
acgcacaatcaatgaaggagaacgagaagacgaaattcatgacgacgaatagtgttttcacgaatagcga
tgacgatgatgtggacgttcagttgaccggacaagtcacggaacatttgaggaatttgcagtgtagtaat
ggttccgcaacttccccatctacatcagtgtcagcttcatcttcttctgctcgtccactgacaaatggaa
ataatcatctttccacggcgtcgtctaccgacacatctctctcattatcggaaaggaataacgttccgtc
tccagctccagttccatatagtgaaagtgctccacaactgaaaacattcaccggagagactccaaaactg
catccacgatctccgttcccgcctcaaccgccagttcttccgcaacgaagcaaaaccgcatcggcagtgg
cgacgacgacgacgaatccgacgacttcgaatggagcaccaccaccagttcctggatcgaaaggaccccc
ggtgccaccgaaaccatcgcatctgaaaatcgcatcgtcgacagtatcctcgggatgctcgtctccacaa
cagtattcgtctgctcgatccgttggtaactcgctctccaacggcagtgttgtctccacaacatcgtcag
atggtgatgtgcaattgtcgaataaggaaaattcgaatgacaaatcagttggagacaagaatgggaacac
caccacaaacaaaacgaccgtcgaaccacctccaccagaagagccacctgttcgtgttcgagcatctcat
cgtgaaaagctttctgattccgaagtgctcaatcaactccgcgagattgttaatccaagtaatccacttg
gaaagtacgagatgaagaagcaaatcggtgttggagcatccggaactgtattcgttgctaatgtggccgg
cagcactgatgtggtggctgtgaagagaatggctttcaagactcagccgaagaaggagatgttgctcacc
gagattaaggttatgaagcagtatcgacacccgaacctcgtcaactacattgaatcgtatctggttgatg
ctgatgatctttgggtagtgatggattatctggaaggtggaaacttgacagatgtcgttgtgaagactga
gttggacgaaggacaaattgcagcagttttgcaagaatgtcttaaagcgcttcacttccttcatagacac
tccatagtgcaccgagatatcaagagtgacaacgtgctgctcggcatgaacggagaggttaagctcaccg
atatgggattctgtgctcagattcagccgggatcgaaaagttgtagagatactgtcgtcggaactccata
ttggatgtcgccggagatattgaacaagaagcagtacaactataaggttgacatttggtcgctgggaatt
atggctctagagatgattgatggagagccaccatatttgagagaaacacctttgaaggctatctacttga
ttgctcaaaacgggaagccagagatcaagcaacgcgacagactgtcttcagagttcaacaatttccttga
caagtgtcttgttgttgatccggatcagagagccgatacaacggagctcttggcacatccattcctgaaa
aaggcgaagccactctcaagcctgattccatacatcagagccgtccgagaaaagtag

Fig. 7:

>pKG40\Pep\pak-3a\WT
MFQNSPMMYDWWNDTTKPKHQQPTLNVLSPWGAYFNHIGNELLHLKIASSTVSSGCSSPQQYSSARSVGN
SLSNGSVVSTTSSDGDVQLSNKENSNDKSVGDKNGNTTTNKTTVEPPPPEEPPVRVRASHREKLSDSEVL
NQLREIVNPSNPLGKYEMKKQIGVGASGTVFVANVAGSTDVVAVKRMAFKTQPKKEMLLTEIKVMKQYRH
PNLVNYIESYLVDADDLWVVMDYLEGGNLTDVVVKTELDEGQIAAVLQECLKALHFLHRHSIVHRDIKSD
NVLLGMNGEVKLTDMGFCAQIQPGSKRDTVVGTPYWMSPEILNKKQYNYKVDIWSLGIMALEMIDGEPPY
LRETPLKAIYLIAQNGKPEIKQRDRLSSEFNNFLDKCLVVDPDQRADTTELLAHPFLKKAKPLSSLIPYI
RAVREK*

Fig. 8:

>pKG123\Pep\pak-3b\WT\v1
MSTSKSSKVRIRNFIGRIFSPSDKDKDRDDEMKPSSSAMDISQPYNTVHRVHVGYDGQKFSGLPQPWMDI
LLRDISLADQKKDPNAVVTALKFYAQSMKENEKTKFMTTNSVFTNSDDDDVDVQLTGQVTEHLRNLQCSN
GSATSPSTSVSASSSSARPLTNGNNHLSTASSTDTSLSLSERNNVPSPAPVPYSESAPQLKTFTGETPKL
HPRSPFPPQPPVLPQRSKTASAVATTTTNPTTSNGAPPPVPGSKGPPVPPKPSHLKIASSTVSSGCSSPQ
QYSSARSVGNSLSNGSVVSTTSSDGDVQLSNKENSNDKSVGDKNGNTTTNKTTVEPPPPEEPPVRVRASH
REKLSDSEVLNQLREIVNPSNPLGKYEMKKQIGVGASGTVFVANVAGSTDVVAVKRMAFKTQPKKEMLLT
EIKVMKQYRHPNLVNYIESYLVDADDLWVVMDYLEGGNLTDVVVKTELDEGQIAAVLQECLKALHFLHRH
SIVHRDIKSDNVLLGMNGEVKLTDMGFCAQIQPGSKRDTVVGTPYWMSPEILNKKQYNYKVDIWSLGIMA
LEMIDGEPPYLRETPLKAIYLIAQNGKPEIKQRDRLSSEFNNFLDKCLVVDPDQRADTTELLAHPFLKKA
KPLSSLIPYIRAVREK*

Fig. 9:

>pKG43\Pep\pak-3b\v2
MSTSKSSKVRIRNFIGRIFSPSDKDKDRDDEMKPSSSAMDISQPYNTVHRVHVGYDGQKFSGLPQPWMDI
LLRDISLADQKKDPNAVVTALKFYAQSMKENEKTKFMTTNSVFTNSDDDDVDVQLTGQVTEHLRNLQCSN
GSATSPSTSVSASSSSARPLTNGNNHLSTASSTDTSLSLSERNNVPSPAPVPYSESAPQLKTFTGETPKL
HPRSPFPPQPPVLPQRSKTASAVATTTTNPTTSNGAPPPVPGSKGPPVPPKPSHLKIASSTVSSGCSSPQ
QYSSARSVGNSLSNGSVVSTTSSDGDVQLSNKENSNDKSVGDKNGNTTTNKTTVEPPPPEEPPVRVRASH
REKLSDSEVLNQLREIVNPSNPLGKYEMKKQIGVGASGTVFVANVAGSTDVVAVKRMAFKTQPKKEMLLT
EIKVMKQYRHPNLVNYIESYLVDADDLWVVMDYLEGGNLTDVVVKTELDEGQIAAVLQECLKALHFLHRH
SIVHRDIKSDNVLLGMNGEVKLTDMGFCAQIQPGSKRDTVVGTPYWMSPEILNKKQYNYKVDIWSLGIMA
LEMIDGEPPYLRETPLKAIYLIAQNGKPEIKQRDRLSSEFNNFLDKCLVVDPDQRADTTELLAHPFLKKA
KPLSSLIPYIRAVREK*

Fig. 10:

>pKG44\Pep\pak-3b\v3
MSTSKSSKVRIRNFIGRIFSPSDKDKDRDDEMKPSSSAMDISQPYNTVHRVHVGYDGQKFSGLPQPWMDI
LLRDISLADQKKDPNAVVTALKFYAQSMKENEKTKFMTTNSVFTNSDDDDVDVQLTGQVTEHLRNLQCSN
GSATSPSTSVSASSSSARPLTNGNNHLSTASSTDTSLSLSERNNVPSPAPVPYSESAPQLKTFTGETPKL
HPRSPFPPQPPVLPQRSKTASAVATTTTNPTTSNGAPPPVPGSKGPPVPPKPSHLKIASSTVSSGCSSPQ
QYSSARSVGNSLSNGSVVSTTSSDGDVQLSNKENSNDKSVGDKNGNTTTNKTTVEPPPPEEPPVRVRASH
REKLSDSEVLNQLREIVNPSNPLGKYEMKKQIGVGASGTVFVANVAGSTDVVAVKRMAFKTQPKKEMLLT
EIKVMKQYRHPNLVNYIESYLVDADDLWVVMDYLEGGNLTDVVVKTELDEGQIAAVLQECLKALHFLHRH
SIVHRDIKSDNVLLGMNGEVKLTDMGFCAQIQPGSKSCRDTVVGTPYWMSPEILNKKQYNYKVDIWSLGI
MALEMIDGEPPYLRETPLKAIYLIAQNGKPEIKQRDRLSSEFNNFLDKCLVVDPDQRADTTELLAHPFLK
KAKPLSSLIPYIRAVREK*

Fig. 11:

>pKG58\Pep\pak-3b\v4
MSTSKSSKVRIRNFIGRIFSPSDKDKDRDDEMKPSSSAMDISQPYNTVHRVHVGYDGQKFSGLPQPWMDI
LLRDISYFSLADQKKDPNAVVTALKFYAQSMKENEKTKFMTTNSVFTNSDDDDVDVQLTGQVTEHLRNLQ
CSNGSATSPSTSVSASSSSARPLTNGNNHLSTASSTDTSLSLSERNNVPSPAPVPYSESAPQLKTFTGET
PKLHPRSPFPPQPPVLPQRSKTASAVATTTTNPTTSNGAPPPVPGSKGPPVPPKPSKENSNDKSVGDKNG
NTTTNKTTVEPPPPEEPPVRVRASHREKLSDSEVLNQLREIVNPSNPLGKYEMKKQIGVGASGTVFVANV
AGSTDVVAVKRMAFKTQPKKEMLLTEIKVMKQYRHPNLVNYIESYLVDADDLWVVMDYLEGGNLTDVVVK
TELDEGQIAAVLQECLKALHFLHRHSIVHRDIKSDNVLLGMNGEVKLTDMGFCAQIQPGSKRDTVVGTPY
WMSPEILNKKQYNYKVDIWSLGIMALEMIDGEPPYLRETPLKAIYLIAQNGKPEIKQRDRLSSEFNNFLD
KCLVVDPDQRADTTELLAHPFLKKAKPLSSLIPYIRAVREK*

Fig. 12:

>pKG59\Pep\pak-3b\v5
MSTSKSSKVRIRNFVGRIFSPSDKDKDRDDEMKPSSSAMDISQPYNTVHRVHVGYDGQKFSGLPQPWMDI
LLRDISLADQKKDPNAVVTALKFYAQSMKENEKTKFMTTNSVFTNSDDDDVDVQLTGQVTEHLRNLQCSN
GSATSPSTSVSASSSSARPLTNGNNHLSTASSTDTSLSLSERNNVPSPAPVPYSESAPQLKTFTGETPKL
HPRSPFPPQPPVLPQRSKTASAVATTTTNPTTSNGAPPPVPGSKGPPVPPKPSHLKIASSTVSSGCSSPQ
QYSSARSVGNSLSNGSVVSTTSSDGDVQLSNKENSNDKSVGDKNGNTTTNKTTVEPPPPEEPPVRVRASH
REKLSDSEVLNQLREIVNPSNPLGKYEMKKQIGVGASGTVFVANVAGSTDVVAVKRMAFKTQPKKEMLLT
EIKVMKQYRHPNLVNYIESYLVDADDLWVVMDYLEGGNLTDVVVKTELDEGQIAAVLQECLKALHFLHRH
SIVHRDIKSDNVLLGMNGEVKLTDMGFCAQIQPGSKSCRDTVVGTPYWMSPEILNKKQYNYKVDIWSLGI
MALEMIDGEPPYLRETPLKAIYLIAQNGKPEIKQRDRLSSEFNNFLDKCLVVDPDQRADTTELLAHPFLK
KAKPLSSLIPYIRAVREK*

Fig. 13A:

```
LOCUS           pKG40\pDON    3541 bp    DNA    circular
SOURCE
  ORGANISM
COMMENT         corresponds to deposited material of DSM 16147
COMMENT         pKG40 pak-3a (kg25/26 seq through WT mp15-220301)

COMMENT         This file is created by Vector NTI
                http://www.informaxinc.com/
COMMENT         VNTDATE|302615684|
COMMENT         VNTDBDATE|302623140|
COMMENT         VNTNAME|pKG40 pDONR pak-3a|
COMMENT         VNTAUTHORNAME|Kaj Grandien|
COMMENT         VNTAUTHORTEL|+49-89-8995117|
COMMENT         VNTAUTHOREML|kaj.grandien@aventis.com|
FEATURES              Location/Qualifiers
     primer_bind      3538..21
                      /vntifkey="28"
                      /label=kg3
     primer_bind      complement(1537..1560)
                      /vntifkey="28"
                      /label=kg4
     CDS              133..1413
                      /vntifkey="4"
                      /label=pak-3a\CDS
     misc_feature     598..1353
                      /vntifkey="21"
                      /label=kinase\domain
BASE COUNT       957 a      805 c      855 g      924 t
ORIGIN
        1 gttaacgcta gcatggatct cgggccccaa ataatgattt tattttgact gatagtgacc
       61 tgttcgttgc aacaaattga tgagcaatgc ttttttataa tgccaacttt gtacaaaaaa
      121 gcaggctcaa aaatgtttca aaatagtccg atgatgtacg actggtggaa tgacaccacc
      181 aaaccgaaac accagcagcc gacacttaac gtgttgtcac catggggagc atatttcaat
      241 cacattggaa atgaactgct gcatctgaaa atcgcatcgt cgacagtatc ctcgggatgc
      301 tcgtctccac aacagtattc gtctgctcga tccgttggta actcgctctc caacggcagt
      361 gttgtctcca acatcgtc agatggtgat gtgcaattgt cgaataagga aaattcgaat
      421 gacaaatcag ttggagacaa gaatgggaac accaccacaa acaaaacgac cgtcgaacca
      481 cctccaccag aagagccacc tgttcgtgtt cgagcatctc atcgtgaaaa gctttctgat
      541 tccgaagtgc tcaatcaact ccgcgagatt gttaatccaa gtaatccact tggaaagtac
      601 gagatgaaga agcaaatcgg tgttggagca tccggaactg tattcgttgc taatgtggcc
      661 ggcagcactg atgtggtggc tgtgaagaga atggctttca agactcagcc gaagaaggag
      721 atgttgctca ccgagattaa ggttatgaag cagtatcgac acccgaacct cgtcaactac
      781 attgaatcgt atctggttga tgctgatgat ctttgggtag tgatggatta tctggaaggt
      841 ggaaacttga cagatgtcgt tgtgaagact gagttggacg aaggacaaat tgcagcagtt
      901 ttgcaagaat gtcttaaagc gcttcacttc cttcatagac actccatagt gcaccagatt
      961 atcaagagtg caacgtgct gctcggcatg aacggagagg ttaagctcac cgatatggga
     1021 ttctgtgctc agattcagcc gggatcgaaa agagatactg tcgtcggaac tccatattgg
     1081 atgtcgccgg agatattgaa caagaagcag tacaactata aggttgacat ttggtcgctg
     1141 ggaattatgg ctctagagat gattgatgga gagccaccat atttgagaga aacacctttg
     1201 aaggctatct acttgattgc tcaaaacggg aagccagaga tcaagcaacg cgacagactg
     1261 tcttcagagt tcaacaattt ccttgacaag tgtcttgttg ttgatccgga tcagagagcc
     1321 gatacaacgg agctcttggc acatccattc ctgaaaaagg cgaagccact ctcaagcctg
     1381 attccataca tcagagccgt ccgagaaaag tagacccagc tttcttgtac aaagttggca
```

Fig. 13B: (cont'd from Fig. 13A)

```
1441 ttataagaaa gcattgctta tcaatttgtt gcaacgaaca ggtcactatc agtcaaaata
1501 aaatcattat ttgccatcca gctgcagctc tggcccgtgt ctcaaaatct ctgatgttac
1561 attgcacaag ataaaaatat atcatcatga acaataaaac tgtctgctta cataaacagt
1621 aatacaaggg gtgttatgag ccatattcaa cgggaaacgt cgaggccgcg attaaattcc
1681 aacatggatg ctgatttata tgggtataaa tgggctcgcg ataatgtcgg gcaatcaggt
1741 gcgacaatct atcgcttgta tgggaagccc gatgcgccag agttgtttct gaaacatggc
1801 aaaggtagcg ttgccaatga tgttacagat gagatggtca gactaaactg gctgacggaa
1861 tttatgcctc ttccgaccat caagcatttt atccgtactc ctgatgatgc atggttactc
1921 accactgcga tccccggaaa aacagcattc caggtattag aagaatatcc tgattcaggt
1981 gaaaatattg ttgatgcgct ggcagtgttc ctgcgccggt tgcattcgat tcctgtttgt
2041 aattgtcctt ttaacagcga tcgcgtattt cgtctcgctc aggcgcaatc acgaatgaat
2101 aacggtttgg ttgatgcgag tgattttgat gacgagcgta atggctggcc tgttgaacaa
2161 gtctggaaag aaatgcataa acttttgcca ttctcaccgg attcagtcgt cactcatggt
2221 gatttctcac ttgataacct tattttgac gaggggaaat taataggttg tattgatgtt
2281 ggacgagtcg gaatcgcaga ccgataccag gatcttgcca tcctatggaa ctgcctcggt
2341 gagttttctc cttcattaca gaaacggctt tttcaaaaat atggtattga taatcctgat
2401 atgaataaat tgcagtttca tttgatgctc gatgagtttt tctaatcaga attggttaat
2461 tggttgtaac actggcagag cattacgctg acttgacggg acggcgcaag ctcatgacca
2521 aaatccctta acgtgagttt tcgttccact gagcgtcaga ccccgtagaa aagatcaaag
2581 gatcttcttg agatcctttt tttctgcgcg taatctgctg cttgcaaaca aaaaaaccac
2641 cgctaccagc ggtggtttgt ttgccggatc aagagctacc aactcttttt ccgaaggtaa
2701 ctggcttcag cagagcgcag ataccaaata ctgtccttct agtgtagccg tagttaggcc
2761 accacttcaa gaactctgta gcaccgccta catacctcgc tctgctaatc ctgttaccag
2821 tggctgctgc cagtggcgat aagtcgtgtc ttaccgggtt ggactcaaga cgatagttac
2881 cggataaggc gcagcggtcg ggctgaacgg ggggttcgtg cacacagccc agcttggagc
2941 gaacgaccta caccgaactg agatacctac agcgtgagct atgagaaagc gccacgcttc
3001 ccgaaggag aaaggcggac aggtatccgg taagcggcag ggtcggaaca ggagagcgca
3061 cgagggagct ccaggggga acgcctggt atctttatag tcctgtcggg tttcgccacc
3121 tctgacttga gcgtcgattt ttgtgatgct cgtcagggg gcggagccta tggaaaaacg
3181 ccagcaacgc ggcctttta cggttcctgg cctttgctg gccttttgct cacatgttct
3241 ttcctgcgtt atcccctgat tctgtggata accgtattac cgctagccag gaagagtttg
3301 tagaaacgca aaaaggccat ccgtcaggat ggccttctgc ttagtttgat gcctggcagt
3361 ttatggcggg cgtcctgccc gccaccctcc gggccgttgc ttcacaacgt tcaaatccgc
3421 tcccggcgga tttgtcctac tcaggagagc gttcaccgac aaacaacaga taaaacgaaa
3481 ggcccagtct tccgactgag cctttcgttt tatttgatgc ctggcagttc cctactctcg
3541 c
```

Fig. 14A:

```
LOCUS       pKG123\pDO    4201 bp    DNA    circular
SOURCE
  ORGANISM
COMMENT     corresponds to deposited material of DSM 16152
COMMENT     This file is created by Vector NTI
            http://www.informaxinc.com/
COMMENT     VNTDATE|302552679|
COMMENT     VNTDBDATE|302623140|
COMMENT     VNTNAME|pKG123 pDONR pak-3 WT|
COMMENT     VNTAUTHORNAME|Kaj Grandien|
COMMENT     VNTAUTHORTEL|+49-89-8995117|
COMMENT     VNTAUTHOREML|kaj.grandien@aventis.com|
FEATURES             Location/Qualifiers
     primer_bind     4198..21
                     /vntifkey="28"
                     /label=kg3
     primer_bind     complement(2197..2220)
                     /vntifkey="28"
                     /label=kg4
     CDS             133..2073
                     /vntifkey="4"
                     /label=pak-3b\CDS
     misc_feature    253..426
                     /vntifkey="21"
                     /label=CRIB\domain
     misc_feature    1258..2013
                     /vntifkey="21"
                     /label=kinase\domain
BASE COUNT     1142 a    987 c    1006 g    1066 t
ORIGIN
        1 gttaacgcta gcatggatct cgggccccaa ataatgattt tattttgact gatagtgacc
       61 tgttcgttgc aacaaattga tgagcaatgc ttttttataa tgccaacttt gtacaaaaaa
      121 gcaggctcaa aaatgtcaac ttcaaaaagt tccaaggtgc gaatacggaa tttcatcggg
      181 cgaatcttct ctcccagcga taaagacaag gatcgagacg atgagatgaa gccatcctcg
      241 tccgcaatgg atattagtca gccatataac acagtgcatc gagtccacgt tggatacgac
      301 ggccagaagt tcagcggact gccgcaacca tggatggata ttcttctccg agacattagt
      361 cttgccgatc agaagaagga tccgaacgcg gtggtgactg cgttgaagtt ctacgcacaa
      421 tcaatgaagg agaacgagaa gacgaaattc atgacgacga atagtgtttt cacgaatagc
      481 gatgacgatg atgtggacgt tcagttgacc ggacaagtca cggaacattt gaggaatttg
      541 cagtgtagta atggttccgc aacttcccca tctacatcag tgtcagcttc atcttcttct
      601 gctcgtccac tgacaaatgg aaataatcat ctttccacgg cgtcgtctac cgacacatct
      661 ctctcattat cggaaaggaa taacgttccg tctccagctc cagttccata tagtgaaagt
      721 gctccacaac tgaaaacatt caccggagag actccaaaac tgcatccacg atctccgttc
      781 ccgcctcaac cgccagttct tccgcaacga agcaaaaccg catcggcagt ggcgacgacg
      841 acgacgaatc cgacgacttc gaatggagca ccaccaccag ttcctggatc gaaaggaccc
      901 ccggtgccac cgaaaccatc gcatctgaaa atcgcatcgt cgacagtatc ctcgggatgc
      961 tcgtctccac aacagtattc gtctgctcga tccgttggta actcgctctc caacggcagt
     1021 gttgtctcca caacatcgtc agatggtgat gtgcaattgt cgaataagga aaattcgaat
     1081 gacaaatcag ttggagacaa gaatgggaac accaccacaa acaaaacgac cgtcgaacca
     1141 cctccaccag aagagccacc tgttcgtgtt cgagcatctc atcgtgaaaa gctttctgat
     1201 tccgaagtgc tcaatcaact ccgcgagatt gttaatccaa gtaatccact tggaaagtac
     1261 gagatgaaga agcaaatcgg tgttggagca tccggaactg tattcgttgc taatgtggcc
     1321 ggcagcactg atgtggtggc tgtgaagaga atggctttca agactcagcc gaagaaggag
```

Fig. 14B: (cont'd from Fig. 14A)

```
1381 atgttgctca ccgagattaa ggttatgaag cagtatcgac acccgaacct cgtcaactac
1441 attgaatcgt atctggttga tgctgatgat ctttgggtag tgatggatta tctggaaggt
1501 ggaaacttga cagatgtcgt tgtgaagact gagttggacg aaggacaaat tgcagcagtt
1561 ttgcaagaat gtcttaaagc gcttcacttc cttcatagac actccatagt gcaccgagat
1621 atcaagagtg acaacgtgct gctcggcatg aacggagagg ttaagctcac cgatatggga
1681 ttctgtgctc agattcagcc gggatcgaaa agagatactg tcgtcggaac tccatattgg
1741 atgtcgccgg agatattgaa caagaagcag tacaactata aggttgacat tggtcgctg
1801 ggaattatgg ctctagagat gattgatgga gagccaccat atttgagaga aacacctttg
1861 aaggctatct acttgattgc tcaaaacggg aagccagaga tcaagcaacg cgacagactg
1921 tcttcagagt tcaacaattt ccttgacaag tgtcttgttg ttgatccgga tcagagagcc
1981 gatacaacgg agctcttggc acatccattc ctgaaaaagg cgaagccact ctcaagcctg
2041 attccataca tcagagccgt ccgagaaaag tagacccagc tttcttgtac aaagttggca
2101 ttataagaaa gcattgctta tcaatttgtt gcaacgaaca ggtcactatc agtcaaaata
2161 aaatcattat ttgccatcca gctgcagctc tggcccgtgt ctcaaaatct ctgatgttac
2221 attgcacaag ataaaaatat atcatcatga acaataaaac tgtctgctta cataaacagt
2281 aatacaaggg gtgttatgag ccatattcaa cgggaaacgt cgaggccgcg attaaattcc
2341 aacatggatg ctgatttata tgggtataaa tgggctcgcg ataatgtcgg gcaatcaggt
2401 gcgacaatct atcgcttgta tgggaagccc gatgcgccag agttgtttct gaaacatggc
2461 aaaggtagcg ttgccaatga tgttacagat gagatggtca gactaaactg gctgacggaa
2521 tttatgcctc ttccgaccat caagcatttt atccgtactc ctgatgatgc atggttactc
2581 accactgcga tccccggaaa aacagcattc caggtattag aagaatatcc tgattcaggt
2641 gaaatattg ttgatgcgct ggcagtgttc ctgcgccggt tgcattcgat tcctgtttgt
2701 aattgtcctt ttaacagcga tcgcgtattt cgtctcgctc aggcgcaatc acgaatgaat
2761 aacggtttgg ttgatgcgag tgatttttgat gacgagcgta atggctggcc tgttgaacaa
2821 gtctggaaag aaatgcataa acttttgcca ttctcaccgg attcagtcgt cactcatggt
2881 gatttctcac ttgataacct tatttttgac gaggggaaat taataggttg tattgatgtt
2941 ggacgagtcg gaatcgcaga ccgataccag gatcttgcca tcctatggaa ctgcctcggt
3001 gagttttctc cttcattaca gaaacggctt tttcaaaaat atggtattga taatcctgat
3061 atgaataaat tgcagtttca tttgatgctc gatgagtttt tctaatcaga attggttaat
3121 tggttgtaac actggcagag cattacgctg acttgacggg acggcgcaag ctcatgacca
3181 aaatcccta acgtgagttt tcgttccact gagcgtcaga ccccgtagaa aagatcaaag
3241 gatcttcttg agatcctttt tttctgcgcg taatctgctg cttgcaaaca aaaaaccac
3301 cgctaccagc ggtggtttgt ttgccggatc aagagctacc aactcttttt ccgaaggtaa
3361 ctggcttcag cagagcgcag ataccaaata ctgtccttct agtgtagccg tagttaggcc
3421 accacttcaa gaactctgta gcaccgccta catacctcgc tctgctaatc ctgttaccag
3481 tggctgctgc cagtggcgat aagtcgtgtc ttaccgggtt ggactcaaga cgatagttac
3541 cggataaggc gcagcggtcg ggctgaacgg ggggttcgtg cacacagccc agcttggagc
3601 gaacgaccta caccgaactg agatacctac agcgtgagct atgagaaagc gccacgcttc
3661 ccgaagggag aaaggcggac aggtatccgg taagcggcag ggtcggaaca ggagagcgca
3721 cgagggagct tccaggggga aacgcctggt atctttatag tcctgtcggg tttcgccacc
3781 tctgacttga gcgtcgattt ttgtgatgct cgtcagggg gcggagccta tggaaaaacg
3841 ccagcaacgc ggccttttta cggttcctgg cttttgctg gcctttgct cacatgttct
3901 ttcctgcgtt atccctgat tctgtggata accgtattac cgctagccag gaagagtttg
3961 tagaaacgca aaaggccat ccgtcaggat ggccttctgc ttagtttgat gcctggcagt
4021 ttatggcggg cgtcctgccc gccaccctcc gggccgttgc ttcacaacgt tcaaatccgc
4081 tcccggcgga tttgtcctac tcaggagagc gttcaccgac aaacaacaga taaaacgaaa
4141 ggcccagtct ccgactgag cctttcgttt tatttgatgc ctggcagttc cctactctcg
4201 c
```

Fig. 15A:

```
LOCUS        pKG43\pDON    4278 bp    DNA    circular
SOURCE
  ORGANISM
COMMENT      corresponds to deposited material of DSM 16148
COMMENT      This file is created by Vector NTI
             http://www.informaxinc.com/
COMMENT      VNTDATE|302608604|
COMMENT      VNTDBDATE|302623141|
COMMENT      VNTNAME|pKG43 pDONR pak-3b SL1 Ala-Ala|
COMMENT      VNTAUTHORNAME|Kaj Grandien|
COMMENT      VNTAUTHORTEL|+49-89-8995117|
COMMENT      VNTAUTHOREML|kaj.grandien@aventis.com|
FEATURES             Location/Qualifiers
     primer_bind     4275..21
                     /vntifkey="28"
                     /label=kg3
     primer_bind     complement(2274..2297)
                     /vntifkey="28"
                     /label=kg4
     CDS             210..2150
                     /vntifkey="4"
                     /label=pa-3b\CDS
     conflict        1889..1889
                     /vntifkey="83"
                     /label=gct->gcc\(Ala->Ala)
     misc_feature    330..503
                     /vntifkey="21"
                     /label=CRIB\domain
     misc_feature    1335..2090
                     /vntifkey="21"
                     /label=Kinase\domain
     misc_feature    128..149
                     /vntifkey="21"
                     /label=SL1\leader
BASE COUNT     1160 a     1007 c     1020 g     1091 t
ORIGIN
        1 gttaacgcta gcatggatct cgggccccaa ataatgattt tattttgact gatagtgacc
       61 tgttcgttgc aacaaattga tgagcaatgc ttttttataa tgccaacttt gtacaaaaaa
      121 gcaggctggt ttaattaccc aagtttgaga tttaccttaa catcgggtct gacaaccgtg
      181 tcgcttacga cgcattctaa tcattaacca tgtcaacttc aaaaagttcc aaggtgcgaa
      241 tacggaattt catcgggcga atcttctctc ccagcgataa agacaaggat cgagacgatg
      301 agatgaagcc atcctcgtcc gcaatggata ttagtcagcc atataacaca gtgcatcgag
      361 tccacgttgg atacgacggc cagaagttca gcggactgcc gcaaccatgg atggatattc
      421 ttctccgaga cattagtctt gccgatcaga agaaggatcc gaacgcggtg gtgactgcgt
      481 tgaagttcta cgcacaatca atgaaggaga acgagaagac gaaattcatg acgacgaata
      541 gtgttttcac gaatagcgat gacgatgatg tggacgttca gttgaccgga caagtcacgg
      601 aacatttgag gaatttgcag tgtagtaatg gttccgcaac ttccccatct acatcagtgt
      661 cagcttcatc ttcttctgct cgtccactga caatggaaa taatcatctt tccacggcgt
      721 cgtctaccga cacatctctc tcattatcgg aaaggaataa cgttccgtct ccagctccag
      781 ttccatatag tgaaagtgct ccacaactga aacattcac cggagagact ccaaaactgc
      841 atccacgatc tccgttcccg cctcaaccgc cagttcttcc gcaacgaagc aaaaccgcat
      901 cggcagtggc gacgacgacg acgaatccga cgacttcgaa tggagcacca ccaccagttc
      961 ctggatcgaa aggaccccg gtgccaccga aaccatcgca tctgaaaatc gcatcgtcga
     1021 cagtatcctc gggatgctcg tctccacaac agtattcgtc tgctcgatcc gttggtaact
```

Fig. 15B: (cont'd from Fig. 15A)

```
1081 cgctctccaa cggcagtgtt gtctccacaa catcgtcaga tggtgatgtg caattgtcga
1141 ataaggaaaa ttcgaatgac aaatcagttg gagacaagaa tgggaacacc accacaaaca
1201 aaacgaccgt cgaaccacct ccaccagaag agccacctgt tcgtgttcga gcatctcatc
1261 gtgaaaagct ttctgattcc gaagtgctca atcaactccg cgagattgtt aatccaagta
1321 atccacttgg aaagtacgag atgaagaagc aaatcggtgt tggagcatcc ggaactgtat
1381 tcgttgctaa tgtggccggc agcactgatg tggtggctgt gaagagaatg gctttcaaga
1441 ctcagccgaa gaaggagatg ttgctcaccg agattaaggt tatgaagcag tatcgacacc
1501 cgaacctcgt caactacatt gaatcgtatc tggttgatgc tgatgatctt tgggtagtga
1561 tggattatct ggaaggtgga aacttgacag atgtcgttgt gaagactgag ttggacgaag
1621 gacaaattgc agcagttttg caagaatgtc ttaaagcgct tcacttcctt catagacact
1681 ccatagtgca ccgagatatc aagagtgaca acgtgctgct cggcatgaac ggagaggtta
1741 agctcaccga tatgggattc tgtgctcaga ttcagccggg atcgaaaaga gatactgtcg
1801 tcggaactcc atattggatg tcgccggaga tattgaacaa gaagcagtac aactataagg
1861 ttgacatttg gtcgctggga attatggccc tagagatgat tgatggagag ccaccatatt
1921 tgagagaaac acctttgaag gctatctact tgattgctca aaacgggaag ccagagatca
1981 agcaacgcga cagactgtct tcagagttca caatttcct tgacaagtgt cttgttgttg
2041 atccggatca gagagccgat acaacggagc tcttggcaca tccattcctg aaaaaggcga
2101 agccactctc aagcctgatt ccatacatca gagccgtccg agaaagtag acccagcttt
2161 cttgtacaaa gttggcatta taagaaagca ttgcttatca atttgttgca acgaacaggt
2221 cactatcagt caaaataaaa tcattatttg ccatccagct gcagctctgg cccgtgtctc
2281 aaaatctctg atgttacatt gcacaagata aaaatatatc atcatgaaca ataaaactgt
2341 ctgcttacat aaacagtaat acaaggggtg ttatgagcca tattcaacgg gaaacgtcga
2401 ggccgcgatt aaattccaac atggatgctg atttatatgg gtataatgg gctcgcgata
2461 atgtcgggca atcaggtgcg acaatctatc gcttgtatgg gaagcccgat gcgccagagt
2521 tgtttctgaa acatggcaaa ggtagcgttg ccaatgatgt tacagatgag atggtcagac
2581 taaactggct gacggaattt atgcctcttc cgaccatcaa gcattttatc cgtactcctg
2641 atgatgcatg gttactcacc actgcgatcc ccggaaaaac agcattccag gtattagaag
2701 aatatcctga ttcaggtgaa aatattgttg atgcgctggc agtgttcctg cgccggttgc
2761 attcgattcc tgtttgtaat tgtccttta acagcgatcg cgtatttcgt ctcgctcagg
2821 cgcaatcacg aatgaataac ggtttggttg atgcgagtga ttttgatgac gagcgtaatg
2881 gctggcctgt tgaacaagtc tggaaagaaa tgcataaact tttgccattc tcaccggatt
2941 cagtcgtcac tcatggtgat ttctcacttg ataaccttat ttttgacgag gggaaattaa
3001 taggttgtat tgatgttgga cgagtcggaa tcgcagaccg ataccaggat cttgccatcc
3061 tatggaactg cctcggtgag ttttctcctt cattacagaa acggcttttt caaaaatatg
3121 gtattgataa tcctgatatg aataaattgc agtttcattt gatgctcgat gagttttct
3181 aatcagaatt ggttaattgg ttgtaacact ggcagagcat tacgctgact tgacgggacg
3241 gcgcaagctc atgaccaaaa tcccttaacg tgagttttcg ttccactgag cgtcagaccc
3301 cgtagaaaag atcaaaggat cttcttgaga tcctttttt ctgcgcgtaa tctgctgctt
3361 gcaaacaaaa aaaccaccgc taccagcggt ggtttgtttg ccggatcaag agctaccaac
3421 tctttttccg aaggtaactg gcttcagcag agcgcagata ccaaatactg tccttctagt
3481 gtagccgtag ttaggccacc acttcaagaa ctctgtagca ccgcctacat acctcgctct
3541 gctaatcctg ttaccagtgg ctgctgccag tggcgataag tcgtgtctta ccgggttgga
3601 ctcaagacga tagttaccgg ataaggcgca gcggtcgggc tgaacggggg gttcgtgcac
3661 acagcccagc ttggagcgaa cgacctacac cgaactgaga tacctacagc gtgagctatg
3721 agaaagcgcc acgcttccg aagggagaaa ggcggacagg tatccggtaa gcggcagggt
3781 cggaacagga gagcgcacga gggagcttcc agggggaaac gcctggtatc tttatagtcc
3841 tgtcgggttt cgccacctct gacttgagcg tcgatttttg tgatgctcgt caggggggcg
3901 gagcctatgg aaaaacgcca gcaacgcggc cttttacgg ttcctggcct tttgctggcc
3961 ttttgctcac atgttcttc ctgcgttatc cctgattct gtggataacc gtattaccgc
4021 tagccaggaa gagtttgtag aaacgcaaaa aggccatccg tcaggatggc cttctgctta
4081 gtttgatgcc tggcagttta tggcgggcgt cctgcccgcc acctcgggg ccgttgcttc
4141 acaacgttca atccgctcc ggcggatt gtcctactca ggagagcgtt caccgacaaa
4201 caacagataa aacgaaaggc ccagtcttcc gactgagcct ttcgttttat ttgatgcctg
4261 gcagttccct actctcgc
```

Fig. 16A:

```
LOCUS        pKG44\pDON    4207 bp    DNA    circular
SOURCE
  ORGANISM
COMMENT      corresponds to deposited material of DSM 16149
COMMENT      This file is created by Vector NTI
             http://www.informaxinc.com/
COMMENT      VNTDATE|302609280|
COMMENT      VNTDBDATE|302623141|
COMMENT      VNTNAME|pKG44 pDONR pak-3b 6bp ins+ Ala-Ala|
COMMENT      VNTAUTHORNAME|Kaj Grandien|
COMMENT      VNTAUTHORTEL|+49-89-8995117|
COMMENT      VNTAUTHOREML|kaj.grandien@aventis.com|
FEATURES             Location/Qualifiers
     primer_bind     4204..21
                     /vntifkey="28"
                     /label=kg3
     primer_bind     complement(2203..2226)
                     /vntifkey="28"
                     /label=kg4
     conflict        1713..1718
                     /vntifkey="83"
                     /label=Insertion\6bp\in-frame
                     /note="Splice variant"
     misc_feature    253..426
                     /vntifkey="21"
                     /label=CRIB\domain
     misc_feature    1258..2019
                     /vntifkey="21"
                     /label=kinase\domain
     CDS             133..2079
                     /vntifkey="4"
                     /label=pak-3b\CDS
     conflict        1818..1818
                     /vntifkey="83"
                     /label=gct->gcc\(Ala->Ala)
                     /note="likely polymorphism"
BASE COUNT      1143 a      988 c     1008 g     1068 t
ORIGIN
    1 gttaacgcta gcatggatct cgggccccaa ataatgattt tattttgact gatagtgacc
   61 tgttcgttgc aacaaattga tgagcaatgc ttttttataa tgccaacttt gtacaaaaaa
  121 gcaggctcaa aaatgtcaac ttcaaaaagt tccaaggtgc gaatacggaa tttcatcggg
  181 cgaatcttct ctcccagcga taaagacaag gatcgagacg atgagatgaa gccatcctcg
  241 tccgcaatgg atattagtca gccatataac acagtgcatc gagtccacgt tggatacgac
  301 ggccagaagt tcagcggact gccgcaacca tggatggata ttcttctccg agacattagt
  361 cttgccgatc agaagaagga tccgaacgcg gtggtgactg cgttgaagtt ctacgcacaa
  421 tcaatgaagg agaacgagaa gacgaaattc atgacgacga atagtgtttt cacgaatagc
  481 gatgacgatg atgtggacgt tcagttgacc ggacaagtca cggaacattt gaggaatttg
  541 cagtgtagta atggttccgc aacttcccca tctacatcag tgtcagcttc atcttcttct
  601 gctcgtccac tgacaaatgg aaataatcat ctttccacgg cgtcgtctac cgacacatct
  661 ctctcattat cggaaaggaa taacgttccg tctccagctc cagttccata tagtgaaagt
  721 gctccacaac tgaaaacatt caccggagag actccaaaac tgcatccacg atctccgttc
  781 ccgcctcaac cgccagttct tccgcaacga agcaaaaccg catcggcagt ggcgacgacg
  841 acgacgaatc cgacgacttc gaatggagca ccaccaccag ttcctggatc gaaaggaccc
  901 ccggtgccac cgaaaccatc gcatctgaaa atcgcatcgt cgacagtatc ctcgggatgc
```

Fig. 16B: (cont'd from Fig. 16A)

```
 961 tcgtctccac aacagtattc gtctgctcga tccgttggta actcgctctc caacggcagt
1021 gttgtctcca caacatcgtc agatggtgat gtgcaattgt cgaataagga aaattcgaat
1081 gacaaatcag ttggagacaa gaatgggaac accaccacaa acaaaacgac cgtcgaacca
1141 cctccaccag aagagccacc tgttcgtgtt cgagcatctc atcgtgaaaa gctttctgat
1201 tccgaagtgc tcaatcaact ccgcgagatt gttaatccaa gtaatccact tggaaagtac
1261 gagatgaaga agcaaatcgg tgttggagca tccggaactg tattcgttgc taatgtggcc
1321 ggcagcactg atgtggtggc tgtgaagaga atggctttca agactcagcc gaagaaggag
1381 atgttgctca ccgagattaa ggttatgaag cagtatcgac acccgaacct cgtcaactac
1441 attgaatcgt atctggttga tgctgatgat ctttgggtag tgatggatta tctggaaggt
1501 ggaaacttga cagatgtcgt tgtgaagact gagttggacg aaggacaaat tgcagcagtt
1561 ttgcaagaat gtcttaaagc gcttcacttc cttcatagac actccatagt gcaccgagat
1621 atcaagagtg acaacgtgct gctcggcatg aacggagagg ttaagctcac cgatatggga
1681 ttctgtgctc agattcagcc gggatcgaaa agttgtagag atactgtcgt cggaactcca
1741 tattggatgt cgccggagat attgaacaag aagcagtaca actataaggt tgacatttgg
1801 tcgctgggaa ttatggccct agagatgatt gatggagagc caccatattt gagagaaaca
1861 cctttgaagg ctatctactt gattgctcaa aacgggaagc cagagatcaa gcaacgcgac
1921 agactgtctt cagagttcaa caatttcctt gacaagtgtc ttgttgttga tccggatcag
1981 agagccgata caacggagct cttggcacat ccattcctga aaaggcgaaa gccactctca
2041 agcctgattc catacatcag agccgtccga gaaaagtaga cccagctttc ttgtacaaag
2101 ttggcattat aagaaagcat tgcttatcaa tttgttgcaa cgaacaggtc actatcagtc
2161 aaaataaaat cattatttgc catccagctg cagctctggc ccgtgtctca aaatctctga
2221 tgttacattg cacaagataa aaatatatca tcatgaacaa taaaactgtc tgcttacata
2281 aacagtaata caaggggtgt tatgagccat attcaacggg aaacgtcgag gccgcgatta
2341 aattccaaca tggatgctga tttatatggg tataaatggg ctcgcgataa tgtcgggcaa
2401 tcaggtgcga caatctatcg cttgtatggg aagcccgatg cgccagagtt gtttctgaaa
2461 catggcaaag gtagcgttgc caatgatgtt acagatgaga tggtcagact aaactggctg
2521 acggaattta tgcctcttcc gaccatcaag cattttatcc gtactcctga tgatgcatgg
2581 ttactcacca ctgcgatccc cggaaaaaca gcattccagg tattagaaga atatcctgat
2641 tcaggtgaaa atattgttga tgcgctggca gtgttcctgc gccggttgca ttcgattcct
2701 gtttgtaatt gtccttttaa cagcgatcgc gtatttcgtc tcgctcaggc gcaatcacga
2761 atgaataacg gtttggttga tgcgagtgat tttgatgacg agcgtaatgg ctggcctgtt
2821 gaacaagtct ggaaagaaat gcataaactt ttgccattct caccggattc agtcgtcact
2881 catggtgatt tctcacttga taaccttatt tttgacgagg ggaaattaat aggttgtatt
2941 gatgttggac gagtcggaat cgcagaccga taccaggatc ttgccatcct atggaactgc
3001 ctcggtgagt tttctccttc attacagaaa cggctttttc aaaaatatgg tattgataat
3061 cctgatatga ataaattgca gtttcatttg atgctcgatg agttttttcta atcagaattg
3121 gttaattggt tgtaacactg gcagagcatt acgctgactt gacgggacgg cgcaagctca
3181 tgaccaaaat cccttaacgt gagttttcgt tccactgagc gtcagacccc gtagaaaaga
3241 tcaaaggatc ttcttgagat cctttttttc tgcgcgtaat ctgctgcttg caaacaaaaa
3301 aaccaccgct accagcggtg tttgtttgc cggatcaaga ctaccaact cttttccga
3361 aggtaactgg cttcagcaga gcgcagatac caaatactgt ccttctagtg tagccgtagt
3421 taggccacca cttcaagaac tctgtagcac cgcctacata cctcgctctg ctaatcctgt
3481 taccagtggc tgctgccagt ggcgataagt cgtgtcttac cgggttggac tcaagacgat
3541 agttaccgga taaggcgcag cggtcgggct gaacggggg ttcgtgcaca cagcccagct
3601 tggagcgaac gacctacacc gaactgagat acctacagcg tgagctatga gaaagcgcca
3661 cgcttcccga agggagaaag gcggacaggt atccggtaag cggcagggtc ggaacaggag
3721 agcgcacgag ggagcttcca gggggaaacg cctggtatct ttatagtcct gtcgggtttc
3781 gccacctctg acttgagcgt cgatttttgt gatgctcgtc agggggggcgg agcctatgga
3841 aaaacgccag caacgcggcc tttttacggt tcctggcctt ttgctggcct tttgctcaca
3901 tgttctttcc tgcgttatcc cctgattctg tggataaccg tattaccgct agccaggaag
3961 agtttgtaga aacgcaaaaa ggccatccgt caggatggcc ttctgcttag tttgatgcct
4021 ggcagtttat ggcgggcgtc ctgcccgcca ccctccgggc cgttgcttca caacgttcaa
4081 atccgctccc ggcggatttg tcctactcag gagagcgttc accgacaaac aacagataaa
4141 acgaaaggcc cagtcttccg actgagcctt tcgttttatt tgatgcctgg cagttccctca
4201 ctctcgc
```

Fig. 17A:

```
LOCUS       pKG58\pDON    4066 bp   DNA    circular
SOURCE
  ORGANISM
COMMENT     corresponds to deposited material of DSM 16150
COMMENT     This file is created by Vector NTI
            http://www.informaxinc.com/
COMMENT     VNTDATE|302611721|
COMMENT     VNTDBDATE|302623141|
COMMENT     VNTNAME|pKG58 pDONR 9bp ins + Delta exon 7|
COMMENT     VNTAUTHORNAME|Kaj Grandien|
COMMENT     VNTAUTHORTEL|+49-89-8995117|
COMMENT     VNTAUTHOREML|kaj.grandien@aventis.com|
FEATURES             Location/Qualifiers
     primer_bind     4063..21
                     /vntifkey="28"
                     /label=kg3
     primer_bind     complement(2062..2085)
                     /vntifkey="28"
                     /label=kg4
     CDS             133..1938
                     /vntifkey="4"
                     /label=pak-3b\variant\CDS
     conflict        360..368
                     /vntifkey="83"
                     /label=9bp\insertion\in-frame
                     /note="splice variant"
     conflict        930..930
                     /vntifkey="83"
                     /label=Exon\7\deletion\144bp
                     /note="After this nucleotide, likely splice variant"
     misc_feature    253..435
                     /vntifkey="21"
                     /label=CRIB\domain
     misc_feature    1123..1878
                     /vntifkey="21"
                     /label=Kinase\domain
BASE COUNT     1112 a       949 c       975 g      1030 t
ORIGIN
        1 gttaacgcta gcatggatct cgggccccaa ataatgattt tattttgact gatagtgacc
       61 tgttcgttgc aacaaattga tgagcaatgc ttttttataa tgccaacttt gtacaaaaaa
      121 gcaggctcaa aaatgtcaac ttcaaaaagt tccaaggtgc gaatacggaa tttcatcggg
      181 cgaatcttct ctcccagcga taaagacaag gatcgagacg atgagatgaa gccatcctcg
      241 tccgcaatgg atattagtca gccatataac acagtgcatc gagtccacgt tggatacgac
      301 ggccagaagt tcagcggact gccgcaacca tggatggata ttcttctccg agacattagc
      361 tatttcagtc ttgccgatca gaagaaggat ccgaacgcgg tggtgactgc gttgaagttc
      421 tacgcacaat caatgaagga gaacgagaag acgaaattca tgacgacgaa tagtgttttc
      481 acgaatagcg atgacgatga tgtggacgtt cagttgaccg gacaagtcac ggaacatttg
      541 aggaatttgc agtgtagtaa tggttccgca acttccccat ctacatcagt gtcagcttca
      601 tcttcttctg ctcgtccact gacaaatgga aataatcatc tttccacggc gtcgtctacc
      661 gacacatctc tctcattatc ggaaaggaat aacgttccgt ctccagctcc agttccatat
      721 agtgaaagtg ctccacaact gaaaacattc accggagaga ctccaaaact gcatccacga
      781 tctccgttcc cgcctcaacc gccagttctt ccgcaacgaa gcaaaaccgc atcggcagtg
      841 gcgacgacga cgacgaatcc gacgacttcg aatggagcac caccaccagt tcctggatcg
      901 aaaggacccc cggtgccacc gaaaccatcg aaggaaaatt cgaatgacaa atcagttgga
      961 gacaagaatg ggaacaccac cacaaacaaa cgaccgtcg aaccacctcc accagaagag
```

```
1021 ccacctgttc gtgttcgagc atctcatcgt gaaaagcttt ctgattccga agtgctcaat
1081 caactccgcg agattgttaa tccaagtaat ccacttggaa agtacgagat gaagaagcaa
1141 atcggtgttg gagcatccgg aactgtattc gttgctaatg tggccggcag cactgatgtg
1201 gtggctgtga agagaatggc tttcaagact cagccgaaga aggagatgtt gctcaccgag
1261 attaaggtta tgaagcagta tcgacacccg aacctcgtca actacattga atcgtatctg
1321 gttgatgctg atgatctttg ggtagtgatg gattatctgg aaggtggaaa cttgacagat
1381 gtcgttgtga agactgagtt ggacgaagga caaattgcag cagttttgca agaatgtctt
1441 aaagcgcttc acttccttca tagacactcc atagtgcacc gagatatcaa gagtgacaac
1501 gtgctgctcg gcatgaacgg agaggttaag ctcaccgata tgggattctg tgctcagatt
1561 cagccgggat cgaaaagaga tactgtcgtc ggaactccat attggatgtc gccggagata
1621 ttgaacaaga agcagtacaa ctataaggtt gacatttggt cgctgggaat tatggctcta
1681 gagatgattg atggagagcc accatatttg agagaaacac ctttgaaggc tatctacttg
1741 attgctcaaa cgggaagcc agagatcaag caacgcgaca gactgtcttc agagttcaac
1801 aatttccttg acaagtgtct tgttgttgat ccggatcaga gagccgatac aacggagctc
1861 ttggcacatc cattcctgaa aaaggcgaag ccactctcaa gcctgattcc atacatcaga
1921 gccgtccgag aaaagtagac ccagctttct tgtacaaagt tggcattata agaaagcatt
1981 gcttatcaat ttgttgcaac gaacaggtca ctatcagtca aaataaaatc attatttgcc
2041 atccagctgc agctctggcc cgtgtctcaa aatctctgat gttacattgc acaagataaa
2101 aatatatcat catgaacaat aaaactgtct gcttacataa acagtaatac aagggggtgtt
2161 atgagccata ttcaacggga acgtcgaggg ccgcgattaa attccaacat ggatgctgat
2221 ttatatgggt ataaatgggc tcgcgataat gtcgggcaat caggtgcgac aatctatcgc
2281 ttgtatggga agcccgatgc gccagagttg tttctgaaac atggcaaagg tagcgttgcc
2341 aatgatgtta cagatgagat ggtcagacta aactggctga cggaatttat gcctcttccg
2401 accatcaagc attttatccg tactcctgat gatgcatggt tactcaccac tgcgatcccc
2461 ggaaaaacag cattccaggt attagaagaa tatcctgatt caggtgaaaa tattgttgat
2521 gcgctggcag tgttcctgcg ccggttgcat tcgattcctg tttgtaattg tcctttaac
2581 agcgatcgcg tatttcgtct cgctcaggcg caatcacgaa tgaataacgg tttggttgat
2641 gcgagtgatt ttgatgacga gcgtaatggc tggcctgttg aacaagtctg gaaagaaatg
2701 cataaacttt tgccattctc accggattca gtcgtcactc atggtgattt ctcacttgat
2761 aaccttattt ttgacgaggg gaaattaata ggttgtattg atgttggacg agtcggaatc
2821 gcagaccgat accaggatct tgccatccta tggaactgcc tcggtgagtt ttctccttca
2881 ttacagaaac ggcttttttca aaaatatggt attgataatc ctgatatgaa taaattgcag
2941 tttcatttga tgctcgatga gttttctaa tcagaattgg ttaattggtt gtaacactgg
3001 cagagcatta cgctgacttg acgggacggc gcaagctcat gaccaaaatc ccttaacgtg
3061 agttttcgtt ccactgagcg tcagaccccg tagaaaagat caaggatctc tcttgagatc
3121 ctttttttct gcgcgtaatc tgctgcttgc aaacaaaaaa accaccgcta ccagcggtgg
3181 tttgtttgcc ggatcaagag ctaccaactc tttttccgaa ggtaactggc ttcagcagag
3241 cgcagatacc aaatactgtc cttctagtgt agccgtagtt aggccaccac ttcaagaact
3301 ctgtagcacc gcctacatac ctcgctctgc taatcctgtt accagtggct gctgccagtg
3361 gcgataagtc gtgtcttacc gggttggact caagacgata gttaccggat aaggcgcagc
3421 ggtcgggctg aacggggggt tcgtgcacac agcccagctt ggagcgaacg acctacaccg
3481 aactgagata cctacagcgt gagctatgag aaagcgccac gcttcccgaa gggagaaagg
3541 cggacaggta tccggtaagc ggcagggtcg gaacaggaga gcgcacgagg gagcttccag
3601 ggggaaacgc ctggtatctt tatagtcctg tcgggtttcg ccacctctga cttgagcgtc
3661 gatttttgtg atgctcgtca ggggggcgga gcctatgaaa aacgccagc aacgcggcct
3721 ttttacggtt cctggccttt tgctggcctt ttgctcacat gttctttcct gcgttatccc
3781 ctgattctgt ggataaccgt attaccgcta gccaggaaga gtttgtagaa acgcaaaaag
3841 gccatccgtc aggatggcct tctgcttagt ttgatgcctg gcagtttatg cgggcgtcc
3901 tgcccgccac cctccgggcc gttgcttcac aacgttcaaa tccgctcccg gcggatttgt
3961 cctactcagg agagcgttca ccgacaaaca acagataaaa cgaaaggccc agtcttccga
4021 ctgagccttt cgttttattt gatgcctggc agttccctac tctcgc
```

Fig. 18A:

```
LOCUS       pKG59\pDON   4207 bp   DNA    circular
SOURCE
  ORGANISM
COMMENT       corresponds to deposited material of DSM 16151
COMMENT       This file is created by Vector NTI
              http://www.informaxinc.com/
COMMENT       VNTDATE|302612506|
COMMENT       VNTDBDATE|302623141|
COMMENT       VNTNAME|pKG59 pDONR pak-3b Ile-Val + 6bp ins|
COMMENT       VNTAUTHORNAME|Kaj Grandien|
COMMENT       VNTAUTHORTEL|+49-89-8995117|
COMMENT       VNTAUTHOREML|kaj.grandien@aventis.com|
FEATURES             Location/Qualifiers
     primer_bind     4204..21
                     /vntifkey="28"
                     /label=kg3
     primer_bind     complement(2203..2226)
                     /vntifkey="28"
                     /label=kg4
     conflict        175..175
                     /vntifkey="83"
                     /label=atc->gtc\(Ile->Val)
                     /note="likely PCR artefact"
     CDS             133..2079
                     /vntifkey="4"
                     /label=pak-3b\CDS
     conflict        1713..1718
                     /vntifkey="83"
                     /label=6\bp\insertion\in-frame
                     /note="splice variant, also in pKG44"
     misc_feature    253..426
                     /vntifkey="21"
                     /label=CRIB\domain
     misc_feature    1258..2019
                     /vntifkey="21"
                     /label=kinase\domain
BASE COUNT      1142 a      987 c     1009 g      1069 t
ORIGIN
        1 gttaacgcta gcatggatct cgggccccaa ataatgattt tattttgact gatagtgacc
       61 tgttcgttgc aacaaattga tgagcaatgc tttttttataa tgccaacttt gtacaaaaaa
      121 gcaggctcaa aaatgtcaac ttcaaaaagt tccaaggtgc gaatacggaa tttcgtcggg
      181 cgaatcttct ctcccagcga taaagacaag gatcgagacg atgagatgaa gccatcctcg
      241 tccgcaatgg atattagtca gccatataac acagtgcatc gagtccacgt tggatacgac
      301 ggccagaagt tcagcggact gccgcaacca tggatggata ttcttctccg agacattagt
      361 cttgccgatc agaagaagga tccgaacgcg gtggtgactg cgttgaagtt ctacgcacaa
      421 tcaatgaagg agaacgagaa gacgaaattc atgacgacga atagtgtttt cacgaatagc
      481 gatgacgatg atgtggacgt tcagttgacc ggacaagtca cggaacattt gaggaatttg
      541 cagtgtagta atggttccgc aacttcccca tctacatcag tgtcagcttc atcttcttct
      601 gctcgtccac tgacaaatgg aaataatcat ctttccacgg cgtcgtctac cgacacatct
      661 ctctcattat cggaaaggaa taacgttccg tctccagctc cagttccata tagtgaaagt
      721 gctccacaac tgaaaacatt caccggagag actccaaaac tgcatccacg atctccgttc
      781 ccgcctcaac cgccagttct tccgcaacga agcaaaaccg catcggcagt ggcgacgacg
      841 acgacgaatc cgacgacttc gaatggagca ccaccaccag ttcctggatc gaaaggaccc
      901 ccggtgccac cgaaaccatc gcatctgaaa atcgcatcgt cgacagtatc ctcgggatgc
      961 tcgtctccac aacagtattc gtctgctcga tccgttggta actcgctctc caacggcagt
```

Fig. 18B: (cont'd from Fig. 18A)

```
1021 gttgtctcca caacatcgtc agatggtgat gtgcaattgt cgaataagga aaattcgaat
1081 gacaaatcag ttggagacaa gaatgggaac accaccacaa acaaaacgac cgtcgaacca
1141 cctccaccag aagagccacc tgttcgtgtt cgagcatctc atcgtgaaaa gctttctgat
1201 tccgaagtgc tcaatcaact ccgcgagatt gttaatccaa gtaatccact tggaaagtac
1261 gagatgaaga agcaaatcgg tgttggagca tccggaactg tattcgttgc taatgtggcc
1321 ggcagcactg atgtggtggc tgtgaagaga atggctttca agactcagcc gaagaaggag
1381 atgttgctca ccgagattaa ggttatgaag cagtatcgac acccgaacct cgtcaactac
1441 attgaatcgt atctggttga tgctgatgat ctttgggtag tgatggatta tctgaaggt
1501 ggaaacttga cagatgtcgt tgtgaagact gagttggacg aaggacaaat tgcagcagtt
1561 ttgcaagaat gtcttaaagc gcttcacttc cttcatagac actccatagt gcaccgagat
1621 atcaagagtg acaacgtgct gctcggcatg aacggagagg ttaagctcac cgatatggga
1681 ttctgtgctc agattcagcc gggatcgaaa agttgtagag atactgtcgt cggaactcca
1741 tattggatgt cgccggagat attgaacaag aagcagtaca actataaggt tgacatttgg
1801 tcgctgggaa ttatggctct agagatgatt gatggagagc caccatattt gagagaaaca
1861 ccttttgaagg ctatctactt gattgctcaa aacgggaagc cagagatcaa gcaacgcgac
1921 agactgtctt cagagttcaa caatttcctt gacaagtgtc ttgttgttga tccggatcag
1981 agagccgata caacggagct cttggcacat ccattcctga aaaaggcgaa gccactctca
2041 agcctgattc catacatcag agccgtccga gaaaagtaga cccagctttc ttgtacaaag
2101 ttggcattat aagaaagcat tgcttatcaa tttgttgcaa cgaacaggtc actatcagtc
2161 aaaataaaat cattatttgc catccagctg cagctctggc ccgtgtctca aaatctctga
2221 tgttacattg cacaagataa aaatatatca tcatgaacaa taaaactgtc tgcttacata
2281 aacagtaata caaggggtgt tatgagccat attcaacggg aaacgtcgag gccgcgatta
2341 aattccaaca tggatgctga tttatatggg tataaatggg ctcgcgataa tgtcgggcaa
2401 tcaggtgcga caatctatcg cttgtatggg aagcccgatc gccagagtt gtttctgaaa
2461 catggcaaag gtagcgttgc caatgatgtt acagatgaga tggtcagact aaactggctg
2521 acggaattta tgcctcttcc gaccatcaag catttttatcc gtactcctga tgatgcatgg
2581 ttactcacca ctgcgatccc cggaaaaaca gcattccagg tattagaaga atatcctgat
2641 tcaggtgaaa atattgttga tgcgctggca gtgttcctgc gccggttgca ttcgattcct
2701 gtttgtaatt gtccttttaa cagcgatcgc gtatttcgtc tcgctcaggc gcaatcacga
2761 atgaataacg tttggttga tgcgagtgat tttgatgacg agcgtaatgg ctggcctgtt
2821 gaacaagtct ggaaagaaat gcataaactt ttgccattct caccggattc agtcgtcact
2881 catggtgatt tctcacttga taaccttatt tttgacgagg ggaaattaat aggttgtatt
2941 gatgttggac gagtcggaat cgcagaccga taccaggatc ttgccatcct atggaactgc
3001 ctcggtgagt tttctccttc attacagaaa cggctttttc aaaaatatgg tattgataat
3061 cctgatatga ataaattgca gtttcatttg atgctcgatg agttttttcta atcagaattg
3121 gttaattggt tgtaacactg gcagagcatt acgctgactt gacgggacgg cgcaagctca
3181 tgaccaaaat cccttaacgt gagttttcgt tccactgagc gtcagacccc gtagaaaaga
3241 tcaaaggatc ttcttgagat cctttttttc tgcgcgtaat ctgctgcttg caaacaaaaa
3301 aaccaccgct accagcggtg gtttgtttgc cggatcaaga gctaccaact cttttttccga
3361 aggtaactgg cttcagcaga gcgcagatac caaatactgt ccttctagtg tagccgtagt
3421 taggccacca cttcaagaac tctgtagcac cgcctacata cctcgctctg ctaatcctgt
3481 taccagtggc tgctgccagt ggcgataagt cgtgtcttac cgggttggac tcaagacgat
3541 agttaccgga taaggcgcag cggtcgggct gaacggggg ttcgtgcaca cagcccagct
3601 tggagcgaac gacctacacc gaactgagat acctacagcg tgagctatga gaaagcgcca
3661 cgcttcccga agggagaaag gcggacaggt atccggtaag cggcagggtc ggaacaggag
3721 agcgcacgag ggagcttcca gggggaaacg cctggtatct ttatagtcct gtcgggtttc
3781 gccacctctg acttgagcgt cgatttttgt gatgctcgtc agggggcgg agcctatgga
3841 aaaacgccag caacgcggcc ttttacggt tcctggcctt ttgctggcct tttgctcaca
3901 tgttctttcc tgcgttatcc cctgattctg tggataaccg tattaccgct agccaggaag
3961 agtttgtaga aacgcaaaaa ggccatccgt caggatggcc ttctgcttag tttgatgcct
4021 ggcagtttat ggcggcgtc ctgccgcca ccctccgggc cgttgcttca caacgttcaa
4081 atccgctccc ggcggatttg tcctactcag gagagcgttc accgacaaac aacagataaa
4141 acgaaaggcc cagtcttccg actgagcctt tcgttttatt tgatgcctgg cagttcccta
4201 ctctcgc
```

Fig. 19:

5-GGGGACAAGTTTGTACAAAAAAGCAGGCT-3

Fig. 20:

5-GGGGACCACTTTGTACAAGAAAGCTGGGT-3

Fig. 21:

5-AAAAAGCAGGCTCAAAAATGTTTCAAAATAGTCCGATGAT-3

Fig. 22:

5-AGAAAGCTGGGTCTACTTTTCTCGGACGGCTCT-3

Fig. 23:

5-AAAAAGCAGGCTGGTTTAATTACCCAAGTTTGAG-3

Fig. 24:

5-AGAAAGCTGGGTCTACTTTTCTCGGACGGCTCT-3

Fig. 25:

5-AAAAAGCAGGCTCAAAAATGTCAACTTCAAAAAGTTCCAAG-3

Fig. 26A:

```
LOCUS       pKG61\dT7-pak-1    4447 bp    DNA      circular
DEFINITION  p#61.
SOURCE
  ORGANISM
COMMENT     This file is created by Vector NTI
            http://www.informaxinc.com/
COMMENT     VNTDATE|233849049|
COMMENT     VNTDBDATE|307043153|
COMMENT     VNTNAME|pKG61 dT7-pak-1|
COMMENT     VNTAUTHORNAME|Kaj Grandien|
COMMENT     VNTAUTHORTEL|+49-069-30518706|
COMMENT     VNTAUTHOREML|kaj.grandien@aventis.com|
COMMENT     VNTAUTHORAD1|Aventis Pharma Deutschland GmbH|
COMMENT     VNTAUTHORAD2|Industriepark Hoechst, G879/R020|
COMMENT     VNTAUTHORAD3|D-65926 Frankfurt/M|
COMMENT     VNTAUTHORAD4|Germany|
FEATURES             Location/Qualifiers
    promoter         19..38
                     /vntifkey="30"
                     /label=T7prom\5'
    promoter         complement(1879..1898)
                     /vntifkey="30"
                     /label=T7prom\3'
    misc_feature     287..469
                     /vntifkey="21"
                     /label=CRIB
    misc_feature     962..1717
                     /vntifkey="21"
                     /label=kinase\domain
    CDS              89..1798
                     /vntifkey="4"
                     /label=pak-1\ORF
BASE COUNT     1212 a     1064 c     1085 g     1086 t
ORIGIN
       1 aacctggctt atcgaaatta atacgactca ctataggagg accggcagat ctgatatcac
      61 aagtttgtac aaaaaagcag gctcaaaaAT GAAAGCTTTC TCATCGTATG ATGAGAAACC
     121 ACCAGCACCA CCAATTCGTT TCAGCAGCTC GGCAACGAGG GAGAATCAGG TCGTCGGATT
     181 GAAGCCATTG CCCAAAGAGC CAGAAGCAAC CAAGAAAAAG AAGACGATGC CTAACCCGTT
     241 CATGAAAAAG AACAAAGACA AAAAGGAAGC GTCAGAAAAA CCAGTGATCT CTCGACCGAG
     301 CAATTTCGAA CACACAATTC ATGTCGGATA TGACCCAAAA ACCGGCGAAT TTACGGGAAT
     361 GCCTGAAGCA TGGGCACGTC TTCTCACAGA CTCACAGATC TCAAAACAAG AGCAGCAACA
     421 GAATCCTCAG GCAGTGTTGG ACGCGCTCAA ATACTACACA CAAGGCGAAA GCAGCGGCCA
     481 GAAGTGGTTG CAGTACGATA TGAATGACGC ACCTTCTCGG ACGCCATCAT ACGGACTGAA
     541 ACCGCAACCA TATAGCACAT CATCCCTGCC GTATCATGGC AATAAAATTC AGGATCCAAG
     601 AAAGATGAAT CCAATGACAA CCAGTACAAG TAGTGCGGGG TATAACAGCA AGCAAGGAGT
     661 TCCTCCGACG ACGTTTAGTG TAAATGAGAA TAGATCGAGT ATGCCACCGA GTTATGCACC
     721 GCCACCGGTC CCCCATGGTG AAACTCCTGC TGATATTGTT CCTCCCGCTA TCCCTGATAG
     781 GCCGGCAAGG ACGTTGAGTA TTTACACAAA ACCGAAAGAG GAGGAAGAAA AAATTCCAGA
     841 CCTTTCAAAA GGACAATTTG GTGTACAGGC CAGAGGTCAA AAAGCTAAGA AAAAGATGAC
     901 TGACGCTGAA GTGCTGACTA AGCTCCGTAC CATTGTGTCT ATCGGAAATC CAGATCGAAA
     961 ATATAGAAAA GTTGATAAAA TCGGCTCAGG TGCATCTGGT TCTGTGTACA CCGCTATTGA
    1021 AATTAGTACC GAAGCGGAGG TGGCTATCAA GCAGATGAAC CTGAAGGATC AACCAAAGAA
    1081 GGAATTGATC ATTAATGAGA TTTTGGTGAT GCGTGAGAAT AAGCATGCAA ATATTGTAAA
    1141 TTATTTGGAT TCGTATTTGG TGTGCGATGA ATTATGGGTA GTGATGGAGT ATCTTGCCGG
    1201 TGGATCATTG ACTGATGTTG TCACGGAGTG CCAGATGGAG GATGGAATTA TTGCAGCTGT
    1261 TTGCAGAGAA GTTCTTCAAG CGCTTGAATT CCTCCACAGC CGCACGTCA TTCACAGAGA
    1321 TATTAAATCT GACAATATTC TTTTGGGAAT GGATGGTTCG GTGAAATTGA CCGACTTTGG
    1381 ATTCTGTGCT CAGCTCTCGC CGGAGCAAAG AAAACGCACG ACAATGGTCG GAACTCCATA
```

Fig. 26B: (cont'd from Fig. 26A)

```
1441 CTGGATGGCG CCGGAAGTGG TGACCCGCAA ACAATACGGA CCCAAGGTTG ATGTGTGGTC
1501 CTTGGGAATC ATGGCGATTG AGATGGTCGA AGGAGAACCG CCATATTTGA ATGAAAATCC
1561 ACTCAGGGCT ATCTATCTCA TTGCTACAAA TGGCAAACCC GACTTCCCTG GAAGAGATTC
1621 CATGACTTTG TTGTTCAAGG ACTTTGTCGA CTCTGCGTTG GAAGTACAAG TTGAAAATCG
1681 ATGGTCGGCA AGCCAACTCC TTACGCATCC ATTCCTCCGA TGCGCCAAAC CGCTTGCTTC
1741 ACTGTACTAC TTAATCGTTG CGGCGAAGAA GAGCATCGCC GAAGCTAGCA ACTCATAAac
1801 ccagctttct tgtacaaagt ggtgatatca agcttatcga taccgtcgac ctcgaggggg
1861 ggcccggtac ccaattcgcc ctatagtgag tcgtattacg cgcgctcact ggccgtcgtt
1921 ttacaacgtc gtgactggga aaaccctggc gttacccaac ttaatcgcct tgcagcacat
1981 ccccctttcg ccagctggcg taatagcgaa gaggcccgca ccgatcgccc ttcccaacag
2041 ttgcgcagcc tgaatggcga atgggacgcg ccctgtagcg gcgcattaag cgcggcgggt
2101 gtggtggtta cgcgcagcgt gaccgctaca cttgccagcg ccctagcgcc cgctcctttc
2161 gctttcttcc cttcctttct cgccacgttc gccggctttc cccgtcaagc tctaaatcgg
2221 gggctccctt tagggttccg atttagtgct ttacggcacc tcgaccccaa aaaacttgat
2281 tagggtgatg gttcacgtag tgggccatcg ccctgataga cggtttttcg ccctttgacg
2341 ttggagtcca cgttctttaa tagtggactc ttgttccaaa ctggaacaac actcaaccct
2401 atctcggtct attcttttga tttataaggg attttgccga tttcggccta ttggttaaaa
2461 aatgagctga tttaacaaaa atttaacgcg aattttaaca aaatattaac gcttacaatt
2521 taggtggcac ttttcgggga aatgtgcgcg aacccctat ttgtttattt ttctaaatac
2581 attcaaatat gtatccgctc atgagacaat aaccctgata aatgcttcaa taatattgaa
2641 aaaggaagag tatgagtatt caacatttcc gtgtcgccct tattccctt tttgcggcat
2701 tttgccttcc tgttttgct cacccagaaa cgctggtgaa agtaaaagat gctgaagatc
2761 agttgggtgc acgagtgggt tacatcgaac tggatctcaa cagcggtaag atccttgaga
2821 gttttcgccc cgaagaacgt tttccaatga tgagcacttt taaagttctg ctatgtggcg
2881 cggtattatc ccgtattgac gccgggcaag agcaactcgg tcgccgcata cactattctc
2941 agaatgactt ggttgagtac tcaccagtca cagaaaagca tcttacggat ggcatgacag
3001 taagagaatt atgcagtgct gccataacca tgagtgataa cactgcggcc aacttacttc
3061 tgacaacgat cggaggaccg aaggagctaa ccgcttttt gcacaacatg gggatcatg
3121 taactcgcct tgatcgttgg gaaccggagc tgaatgaagc cataccaaac gacgagcgtg
3181 acaccacgat gcctgtagca atggcaacaa cgttgcgcaa actattaact ggcgaactac
3241 ttactctagc ttcccggcaa caattaatag actggatgga ggcggataaa gttgcaggac
3301 cacttctgcg ctcggccctt ccggctggct ggtttattgc tgataaatct ggagccggtg
3361 agcgtgggtc tcgcggtatc attgcagcac tggggccaga tggtaagccc tcccgtatcg
3421 tagttatcta cacgacgggg agtcaggcaa ctatggatga acgaaataga cagatcgctg
3481 agataggtgc ctcactgatt aagcattggt aactgtcaga ccaagtttac tcatatatac
3541 tttagattga tttaaaactt catttttaat ttaaaaggat ctaggtgaag atccttttg
3601 ataatctcat gaccaaaatc ccttaacgtg agttttcgtt ccactgagcg tcagaccccg
3661 tagaaaagat caaaggatct tcttgagatc cttttttct gcgcgtaatc tgctgcttgc
3721 aaacaaaaaa accaccgcta ccagcggtgg tttgtttgcc ggatcaagag ctaccaactc
3781 ttttccgaa ggtaactggc ttcagcagag cgcagatacc aaatactgtc cttctagtgt
3841 agccgtagtt aggccaccac ttcaagaact ctgtagcacc gcctacatac ctcgctctgc
3901 taatcctgtt accagtggct gctgccagtg gcgataagtc gtgtcttacc gggttggact
3961 caagacgata gttaccggat aaggcgcagc ggtcgggctg aacggggggt tcgtgcacac
4021 agcccagctt ggagcgaacg acctacaccg aactgagata cctacagcgt gagctatgag
4081 aaagcgccac gcttcccgaa gggagaaagg cggacaggta tccggtaagc ggcagggtcg
4141 gaacaggaga gcgcacgagg gagcttccag ggggaaacgc ctggtatctt tatagtcctg
4201 tcgggtttcg ccacctctga cttgagcgtc gatttttgtg atgctcgtca gggggggcgga
4261 gcctatggaa aaacgccagc aacgcggcct ttttacggtt cctggccttt tgctggcctt
4321 ttgctcacat gttctttcct gcgttatccc ctgattctgt ggataaccgt attaccgcct
4381 ttgagtgagc tgataccgct cgccgcagcc gaacgaccga gcgcagcgag tcagtgagcg
4441 aggaagc
```

Fig. 27A:

```
LOCUS       pKG65\dT7-pak-3 3'end    3533 bp    DNA    circular
DEFINITION  p#65.
SOURCE
  ORGANISM
COMMENT     This file is created by Vector NTI
            http://www.informaxinc.com/
COMMENT     VNTDATE|233848377|
COMMENT     VNTDBDATE|307043047|
COMMENT     VNTNAME|pKG65 dT7-58/26 Pak3 3'end|
COMMENT     VNTAUTHORNAME|Kaj Grandien|
COMMENT     VNTAUTHORTEL|+49-069-30518706|
COMMENT     VNTAUTHOREML|kaj.grandien@aventis.com|
COMMENT     VNTAUTHORAD1|Aventis Pharma Deutschland GmbH|
COMMENT     VNTAUTHORAD2|Industriepark Hoechst, G879/R020|
COMMENT     VNTAUTHORAD3|D-65926 Frankfurt/M|
COMMENT     VNTAUTHORAD4|Germany|
FEATURES             Location/Qualifiers
     promoter        19..38
                     /vntifkey="30"
                     /label=T7prom\5'
     promoter        complement(965..984)
                     /vntifkey="30"
                     /label=T7prom\3'
     misc_feature    84..883
                     /vntifkey="21"
                     /label=3'\end\of\Pak-3
BASE COUNT      902 a     845 c      884 g      902 t
ORIGIN
    1 aacctggctt atcgaaatta atacgactca ctatagggag accggcagat ctgatatcac
   61 aagtttgtac aaaaaagcag gctCAAATCG GTGTTGGAGC ATCCGGAACT GTATTCGTTG
  121 CTAATGTGGC CGGCAGCACT GATGTGGTGG CTGTGAAGAG AATGGCTTTC AAGACTCAGC
  181 CGAAGAAGGA GATGTTGCTC ACCGAGATTA AGGTTATGAA GCAGTATCGA CACCCGAACC
  241 TCGTCAACTA CATTGAATCG TATCTGGTTG ATGCTGATGA TCTTTGGGTA GTGATGGATT
  301 ATCTGGAAGG TGGAAACTTG ACAGATGTCG TTGTGAAGAC TGAGTTGGAC GAAGGACAAA
  361 TTGCAGCAGT TTTGCAAGAA TGTCTTAAAG CGCTTCACTT CCTTCATAGA CACTCCATAG
  421 TGCACCGAGA TATCAAGAGT GACAACGTGC TGCTCGGCAT GAACGGAGAG GTTAAGCTCA
  481 CCGATATGGG ATTCTGTGCT CAGATTCAGC CGGGATCGAA AAGAGATACT GTCGTCGGAA
  541 CTCCATATTG GATGTCGCCG GAGATATTGA ACAAGAAGCA GTACAACTAT AAGGTTGACA
  601 TTTGGTCGCT GGGAATTATG GCTCTAGAGA TGATTGATGG AGAGCCACCA TATTTGAGAG
  661 AAACACCTTT GAAGGCTATC TACTTGATTG CTCAAAACGG GAAGCCAGAG ATCAAGCAAC
  721 GCGACAGACT GTCTTCAGAG TTCAACAATT CCTTGACAA GTGTCTTGTT GTTGATCCGG
  781 ATCAGAGAGC CGATACAACG GAGCTCTTGG CACATCCATT CCTGAAAAAG GCGAAGCCAC
  841 TCTCAAGCCT GATTCCATAC ATCAGAGCCG TCCGAGAAAA GTAgacccag ctttcttgta
  901 caaagtggtg atatcaagct tatcgatacc gtcgacctcg agggggggcc cggtacccaa
  961 ttcgccctat agtgagtcgt attacgcgcg ctcactggcc gtcgttttac aacgtcgtga
 1021 ctgggaaaac cctggcgtta cccaacttaa tcgccttgca gcacatcccc ctttcgccag
 1081 ctggcgtaat agcgaagagg cccgcaccga tcgcccttcc caacagttgc gcagcctgaa
 1141 tggcgaatgg gacgcgccct gtagcggcgc attaagcgcg cgggtgtgg tggttacgcg
 1201 cagcgtgacc gctacacttg ccagcgccct agcgcccgct cctttcgctt tcttcccttc
 1261 ctttctcgcc acgttcgccg gctttccccg tcaagctcta atcgggggct cccctttagg
 1321 gttccgattt agtgctttac ggcacctcga cccaaaaaa cttgattagg gtgatggttc
 1381 acgtagtggg ccatcgccct gatagacggt ttttcgccct tgacgttgg agtccacgtt
 1441 ctttaatagt ggactcttgt tccaaactgg aacaacactc aaccctatct cggtctattc
 1501 ttttgattta agggattt tgccgatttc ggcctattgg ttaaaaatg agctgattta
 1561 acaaaaattt aacgcgaatt ttacaaaat attaacgctt acaatttagg tggcactttt
 1621 cggggaaatg tgcgcggaac cctatttgt ttatttttct aaatacattc aaatatgtat
 1681 ccgctcatga acaataaccc tgataaatg cttcaataat attgaaaaag gaagagtatg
 1741 agtattcaac atttccgtgt cgcccttatt cccttttttg cggcattttg ccttcctgtt
```

Fig. 27B: (cont'd from Fig. 27A)

```
1801 tttgctcacc cagaaacgct ggtgaaagta aaagatgctg aagatcagtt gggtgcacga
1861 gtgggttaca tcgaactgga tctcaacagc ggtaagatcc ttgagagttt tcgccccgaa
1921 gaacgttttc caatgatgag cacttttaaa gttctgctat gtggcgcggt attatcccgt
1981 attgacgccg ggcaagagca actcggtcgc cgcatacact attctcagaa tgacttggtt
2041 gagtactcac cagtcacaga aaagcatctt acggatggca tgacagtaag agaattatgc
2101 agtgctgcca taaccatgag tgataacact gcggccaact tacttctgac aacgatcgga
2161 ggaccgaagg agctaaccgc ttttttgcac aacatggggg atcatgtaac tcgccttgat
2221 cgttgggaac cggagctgaa tgaagccata ccaaacgacg agcgtgacac cacgatgcct
2281 gtagcaatgg caacaacgtt gcgcaaacta ttaactggcg aactacttac tctagcttcc
2341 cggcaacaat taatagactg gatggaggcg gataaagttg caggaccact tctgcgctcg
2401 gcccttccgg ctggctggtt tattgctgat aaatctggag ccggtgagcg tgggtctcgc
2461 ggtatcattg cagcactggg gccagatggt aagccctccc gtatcgtagt tatctacacg
2521 acggggagtc aggcaactat ggatgaacga atagacaga tcgctgagat aggtgcctca
2581 ctgattaagc attggtaact gtcagaccaa gttactcat atatacttta gattgattta
2641 aaacttcatt tttaatttaa aaggatctag gtgaagatcc ttttgataa tctcatgacc
2701 aaaatccctt aacgtgagtt tcgttccac tgagcgtcag accccgtaga aaagatcaaa
2761 ggatcttctt gagatccttt tttctgcgc gtaatctgct gcttgcaaac aaaaaaacca
2821 ccgctaccag cggtggtttg tttgccggat caagagctac caactctttt tccgaaggta
2881 actggcttca gcagagcgca gataccaaat actgtccttc tagtgtagcc gtagttaggc
2941 caccacttca agaactctgt agcaccgcct acatacctcg ctctgctaat cctgttacca
3001 gtggctgctg ccagtggcga taagtcgtgt cttaccgggt tggactcaag acgatagtta
3061 ccggataagg cgcagcggtc gggctgaacg gggggttcgt gcacacagcc cagcttggag
3121 cgaacgacct acaccgaact gagatacca gcgtgagc tatgagaaag cgccacgctt
3181 cccgaaggga gaaaggcgga caggtatccg gtaagcggca gggtcggaac aggagagcgc
3241 acgagggagc ttccaggggg aaacgcctgg tatctttata gtcctgtcgg gtttcgccac
3301 ctctgacttg agcgtcgatt tttgtgatgc tcgtcagggg ggcggagcct atggaaaaac
3361 gccagcaacg cggccttttt acggttcctg gccttttgct ggccttttgc tcacatgttc
3421 tttcctgcgt tatccctga ttctgtggat aaccgtatta ccgcctttga gtgagctgat
3481 accgctcgcc gcagccgaac gaccgagcgc agcgagtcag tgagcgagga agc
```

Fig. 28A:

```
LOCUS        pKG71\dT7-pak-3/pak-1   4323 bp    DNA     circular
DEFINITION   p#71.
SOURCE
  ORGANISM
COMMENT      This file is created by Vector NTI
             http://www.informaxinc.com/
COMMENT      VNTDATE|233850223|
COMMENT      VNTDBDATE|307043348|
COMMENT      VNTNAME|pKG71 dT7-Pak3/Pak1|
COMMENT      VNTAUTHORNAME|Kaj Grandien|
COMMENT      VNTAUTHORTEL|+49-069-30518706|
COMMENT      VNTAUTHOREML|kaj.grandien@aventis.com|
COMMENT      VNTAUTHORAD1|Aventis Pharma Deutschland GmbH|
COMMENT      VNTAUTHORAD2|Industriepark Hoechst, G879/R020|
COMMENT      VNTAUTHORAD3|D-65926 Frankfurt/M|
COMMENT      VNTAUTHORAD4|Germany|
FEATURES             Location/Qualifiers
     promoter        19..38
                     /vntifkey="30"
                     /label=T7prom\5'
     promoter        complement(1755..1774)
                     /vntifkey="30"
                     /label=T7prom\3'
     misc_feature    84..883
                     /vntifkey="21"
                     /label=3'\end\of\Pak-3
     misc_feature    885..1674
                     /vntifkey="21"
                     /label=3'end\of\pak-1
BASE COUNT     1122 a    1007 c    1086 g    1108 t
ORIGIN
    1 aacctggctt atcgaaatta atacgactca ctatagggag accggcagat ctgatatcac
   61 aagtttgtac aaaaaagcag gctCAAATCG GTGTTGGAGC ATCCGGAACT GTATTCGTTG
  121 CTAATGTGGC CGGCAGCACT GATGTGGTGG CTGTGAAGAG AATGGCTTTC AAGACTCAGC
  181 CGAAGAAGGA GATGTTGCTC ACCGAGATTA AGGTTATGAA GCAGTATCGA CACCCGAACC
  241 TCGTCAACTA CATTGAATCG TATCTGGTTG ATGCTGATGA TCTTTGGGTA GTGATGGATT
  301 ATCTGGAAGG TGGAAACTTG ACAGATGTCG TTGTGAAGAC TGAGTTGGAC GAAGGACAAA
  361 TTGCAGCAGT TTTGCAAGAA TGTCTTAAAG CGCTTCACTT CCTTCATAGA CACTCCATAG
  421 TGCACCGAGA TATCAAGAGT GACAACGTGC TGCTCGGCAT GAACGGAGAG GTTAAGCTCA
  481 CCGATATGGG ATTCTGTGCT CAGATTCAGC CGGGATCGAA AAGAGATACT GTCGTCGGAA
  541 CTCCATATTG GATGTCGCCG GAGATATTGA ACAAGAAGCA GTACAACTAT AAGGTTGACA
  601 TTTGGTCGCT GGGAATTATG GCTCTAGAGA TGATTGATGG AGAGCCACCA TATTTGAGAG
  661 AAACACCTTT GAAGGCTATC TACTTGATTG CTCAAAACGG GAAGCCAGAG ATCAAGCAAC
  721 GCGACAGACT GTCTTCAGAG TTCAACAATT TCCTTGACAA GTGTCTTGTT GTTGATCCGG
  781 ATCAGAGAGC CGATACAACG GAGCTCTTGG CACATCCATT CCTGAAAAAG GCGAAGCCAC
  841 TCTCAAGCCT GATTCCATAC ATCAGAGCCG TCCGAGAAAA GTAgcACCGC TATTGAAATT
  901 AGTACCGAAG CGGAGGTGGC TATCAAGCAG ATGAACCTGA AGGATCAACC AAAGAAGGAA
  961 TTGATCATTA ATGAGATTTT GGTGATGCGT GAGAATAAGC ATGCAAATAT TGTAAATTAT
 1021 TTGGATTCGT ATTTGGTGTG CGATGAATTA TGGGTAGTGA TGGAGTATCT TGCCGGTGGA
 1081 TCATTGACTG ATGTTGTCAC GGAGTGCCAG ATGGAGGATG GAATTATTGC AGCTGTTTGC
 1141 AGAGAAGTTC TTCAAGCGCT TGAATTCCTC CACAGCCGCC ACGTCATTCA CAGAGATATT
 1201 AAATCTGACA ATATTCTTTT GGGAATGGAT GGTTCGGTGA AATTGACCGA CTTTGGATTC
 1261 TGTGCTCAGC TCTCGCCGGA GCAAAGAAAA CGCACGACAA TGGTCGGAAC TCCATACTGG
 1321 ATGGCGCCGG AAGTGGTGAC CCGCAAACAA TACGGACCCA AGGTTGATGT GTGGTCCTTG
 1381 GGAATCATGG CGATTGAGAT GGTCGAAGGA GAACCGCCAT ATTTGAATGA AAATCCACTC
 1441 AGGGCTATCT ATCTCATTGC TACAAATGGC AAACCCGACT TCCCTGGAAG AGATTCCATG
 1501 ACTTTGTTGT TCAAGGACTT TGTCGACTCT GCGTTGGAAG TACAAGTTGA AAATCGATGG
 1561 TCGGCAAGCC AACTCCTTAC GCATCCATTC CTCCGATGCG CCAAACCGCT TGCTTCACTG
```

Fig. 28B: (cont'd from Fig. 28A)

```
1621 TACTACTTAA TCGTTGCGGC GAAGAAGAGC ATCGCCGAAG CTAGCAACTC ATAAacccag
1681 ctttcttgta caaagtggtg atatcaagct tatcgatacc gtcgacctcg agggggggcc
1741 cggtacccaa ttcgccctat agtgagtcgt attacgcgcg ctcactggcc gtcgttttac
1801 aacgtcgtga ctgggaaaac cctggcgtta cccaacttaa tcgccttgca gcacatcccc
1861 ctttcgccag ctggcgtaat agcgaagagg cccgcaccga tcgcccttcc caacagttgc
1921 gcagcctgaa tggcgaatgg gacgcgccct gtagcggcgc attaagcgcg gcgggtgtgg
1981 tggttacgcg cagcgtgacc gctacacttg ccagcgccct agcgcccgct cctttcgctt
2041 tcttcccttc ctttctcgcc acgttcgccg gctttccccg tcaagctcta aatcgggggc
2101 tccctttagg gttccgattt agtgctttac ggcacctcga ccccaaaaaa cttgattagg
2161 gtgatggttc acgtagtggg ccatcgccct gatagacggt ttttcgccct ttgacgttgg
2221 agtccacgtt ctttaatagt ggactcttgt tccaaactgg aacaacactc aaccctatct
2281 cggtctattc ttttgattta tagggatttt tgccgatttc ggcctattgg ttaaaaaatg
2341 agctgattta acaaaaattt aacgcgaatt ttaacaaaat attaacgctt acaatttagg
2401 tggcactttt cggggaaatg tgcgcggaac ccctatttgt ttatttttct aaatacattc
2461 aaatatgtat ccgctcatga gacaataacc ctgataaatg cttcaataat attgaaaaag
2521 gaagagtatg agtattcaac atttccgtgt cgcccttatt cccttttttg cggcattttg
2581 ccttcctgtt tttgctcacc cagaaacgct ggtgaaagta aagatgctg aagatcagtt
2641 gggtgcacga gtgggttaca tcgaactgga tctcaacagc ggtaagatcc ttgagagttt
2701 tcgccccgaa gaacgttttc caatgatgag cacttttaaa gttctgctat gtggcgcggt
2761 attatcccgt attgacgccg ggcaagagca actcggtcgc cgcatacact attctcagaa
2821 tgacttggtt gagtactcac cagtcacaga aaagcatctt acggatggca tgacagtaag
2881 agaattatgc agtgctgcca taaccatgag tgataacact gcggccaact tacttctgac
2941 aacgatcgga ggaccgaagg agctaaccgc ttttttgcac aacatggggg atcatgtaac
3001 tcgccttgat cgttgggaac cggagctgaa tgaagccata ccaaacgacg agcgtgacac
3061 cacgatgcct gtagcaatgg caacaacgtt gcgcaaacta ttaactggcg aactacttac
3121 tctagcttcc cggcaacaat taatagactg gatggaggcg gataaagttg caggaccact
3181 tctgcgctcg gcccttccgg ctggctggtt tattgctgat aaatctggag ccggtgagcg
3241 tgggtctcgc ggtatcattg cagcactggg gccagatggt aagccctccc gtatcgtagt
3301 tatctacacg acggggagtc aggcaactat ggatgaacga aatagacaga tcgctgagat
3361 aggtgcctca ctgattaagc attggtaact gtcagaccaa gtttactcat atatacttta
3421 gattgattta aaacttcatt tttaatttaa aaggatctag gtgaagatcc ttttgataa
3481 tctcatgacc aaaatccctt aacgtgagtt ttcgttccac tgagcgtcag acccgtaga
3541 aaagatcaaa ggatcttctt gagatccttt ttttctgcgc gtaatctgct gcttgcaaac
3601 aaaaaaacca ccgctaccag cggtggtttg tttgccggat caagagctac caactctttt
3661 tccgaaggta actggcttca gcagagcgca gataccaaat actgtccttc tagtgtagcc
3721 gtagttaggc caccacttca agaactctgt agcaccgcct acatacctcg ctctgctaat
3781 cctgttacca gtggctgctg ccagtggcga taagtcgtgt cttaccgggt tggactcaag
3841 acgatagtta ccggataagg cgcagcggtc gggctgaacg ggggggttcgt gcacacagcc
3901 cagcttggag cgaacgacct acaccgaact gagataccta cagcgtgagc tatgagaaag
3961 cgccacgctt cccgaaggga gaaaggcgga caggtatccg gtaagcggca gggtcggaac
4021 aggagagcgc acgagggagc ttccaggggg aaacgcctgg tatctttata gtcctgtcgg
4081 gtttcgccac ctctgacttg agcgtcgatt tttgtgatgc tcgtcagggg ggcggagcct
4141 atggaaaaac gccagcaacg cggcctttt acggttcctg gccttttgct ggccttttgc
4201 tcacatgttc tttcctgcgt tatcccctga ttctgtggat aaccgtatta ccgcctttga
4261 gtgagctgat accgctcgcc gcagccgaac gaccgagcgc agcgagtcag tgagcgagga
4321 agc
```

Fig. 29A:

```
LOCUS       pKG63\dT7-pak-3a5' 2865 bp    DNA    circular
SOURCE
  ORGANISM
COMMENT     This file is created by Vector NTI
            http://www.informaxinc.com/
COMMENT     VNTDATE|317129516|
COMMENT     VNTDBDATE|317129641|
COMMENT     VNTNAME|pKG63 dT7-pak-3a5'|
COMMENT     VNTAUTHORNAME|Kaj Grandien|
COMMENT     VNTAUTHORTEL|+49-069-30518706|
COMMENT     VNTAUTHOREML|kaj.grandien@aventis.com|
COMMENT     VNTAUTHORAD1|Aventis Pharma Deutschland GmbH|
COMMENT     VNTAUTHORAD2|Industriepark Hoechst, G879/R020|
COMMENT     VNTAUTHORAD3|D-65926 Frankfurt/M|
COMMENT     VNTAUTHORAD4|Germany|
FEATURES            Location/Qualifiers
     promoter       19..38
                    /vntifkey="30"
                    /label=T7prom\5'
     promoter       complement(297..316)
                    /vntifkey="30"
                    /label=T7prom\3'
     misc_feature   89..216
                    /vntifkey="21"
                    /label=Unique\region\for\pak-3a
BASE COUNT     718 a    714 c    700 g    733 t
ORIGIN
    1 aacctggctt atcgaaatta atacgactca ctatagggag accggcagat ctgatatcac
   61 aagtttgtac aaaaaagcag gctcaaaaAT GTTTCAAAAT AGTCCGATGA TGTACGACTG
  121 GTGGAATGAC ACCACCAAAC CGAAACACCA GCAGCCGACA CTTAACGTGT TGTCACCATG
  181 GGGAGCATAT TTCAATCACA TTGGAAATGA ACTGCTaccc agcttcttg tacaaagtgg
  241 tgatatcaag cttatcgata ccgtcgacct cgaggggggg cccggtaccc aattcgccct
  301 atagtgagtc gtattacgcg cgctcactgg ccgtcgtttt acaacgtcgt gactgggaaa
  361 accctggcgt tacccaactt aatcgccttg cagcacatcc ccctttcgcc agctggcgta
  421 atagcgaaga ggcccgcacc gatcgccctt cccaacagtt gcgcagcctg aatggcgaat
  481 gggacgcgcc ctgtagcggc gcattaagcg cggcgggtgt ggtggttacg cgcagcgtga
  541 ccgctacact tgccagcgcc ctagcgcccg ctcctttcgc tttcttccct tcctttctcg
  601 ccacgttcgc cggctttccc cgtcaagctc taaatcgggg gctcccttta gggttccgat
  661 ttagtgcttt acggcaccct gaccccaaaa aacttgatta gggtgatggt tcacgtagtg
  721 ggccatcgcc ctgatagacg gtttttcgcc ctttgacgtt ggagtccacg ttctttaata
  781 gtggactctt gttccaaact ggaacaacac tcaaccctat ctcggtctat tcttttgatt
  841 tataagggat tttgccgatt tcggcctatt ggttaaaaaa tgagctgatt taacaaaaat
  901 ttaacgcgaa ttttaacaaa atattaacgc ttacaattta ggtggcactt tcggggaaa
  961 tgtgcgcgga accctatttt gtttattttt ctaaatacat tcaaatatgt atccgctcat
 1021 gagacaataa ccctgataaa tgcttcaata atattgaaaa aggaagagta tgagtattca
 1081 acatttccgt gtcgccctta ttccctttt tgcggcattt tgccttcctg ttttgctca
 1141 cccagaaacg ctggtgaaag taaagatgc tgaagatcag ttgggtgcac gagtgggtta
 1201 catcgaactg gatctcaaca gcggtaagat ccttgagagt tttcgccccg aagaacgttt
 1261 tccaatgatg agcactttta aagttctgct atgtggcgcg gtattatccc gtattgacgc
 1321 cgggcaagag caactcggtc gccgcataca ctattctcag aatgacttgg ttgagtactc
 1381 accagtcaca gaaaagcatc ttacggatgg catgacagta agagaattat gcagtgctgc
 1441 cataaccatg agtgataaca ctgcggccaa cttacttctg acaacgatcg gaggaccgaa
 1501 ggagctaacc gcttttttgc acaacatggg gatcatgta actcgccttg atcgttggga
 1561 accggagctg aatgaagcca taccaaacga cgagcgtgac accacgatgc ctgtagcaat
 1621 ggcaacaacg ttgcgcaaac tattaactgg cgaactactt actctagctt cccggcaaca
 1681 attaatagac tggatggagg cggataaagt tgcaggacca cttctgcgct cggcccttcc
 1741 ggctggctgg tttattgctg ataaatctgg agccggtgag cgtgggtctc gcggtatcat
 1801 tgcagcactg gggccagatg gtaagccctc ccgtatcgta gttatctaca cgacggggag
```

Fig. 29B: (cont'd from Fig. 29A)

```
1861 tcaggcaact atggatgaac gaaatagaca gatcgctgag ataggtgcct cactgattaa
1921 gcattggtaa ctgtcagacc aagtttactc atatatactt tagattgatt taaaacttca
1981 tttttaattt aaaaggatct aggtgaagat ccttttttgat aatctcatga ccaaaatccc
2041 ttaacgtgag ttttcgttcc actgagcgtc agaccccgta gaaaagatca aaggatcttc
2101 ttgagatcct ttttttctgc gcgtaatctg ctgcttgcaa acaaaaaaac caccgctacc
2161 agcggtggtt tgtttgccgg atcaagagct accaactctt tttccgaagg taactggctt
2221 cagcagagcg cagataccaa atactgtcct tctagtgtag ccgtagttag gccaccactt
2281 caagaactct gtagcaccgc ctacatacct cgctctgcta atcctgttac cagtggctgc
2341 tgccagtggc gataagtcgt gtcttaccgg gttggactca agacgatagt taccggataa
2401 ggcgcagcgg tcgggctgaa cggggggttc gtgcacacag cccagcttgg agcaacgac
2461 ctacaccgaa ctgagatacc tacagcgtga gctatgagaa agcgccacgc ttcccgaagg
2521 gagaaaggcg gacaggtatc cggtaagcgg cagggtcgga acaggagagc gcacgaggga
2581 gcttccaggg ggaaacgcct ggtatcttta tagtcctgtc gggtttcgcc acctctgact
2641 tgagcgtcga ttttgtgat gctcgtcagg ggggcggagc ctatggaaaa acgccagcaa
2701 cgcggccttt ttacggttcc tggccttttg ctggccttt gctcacatgt tctttcctgc
2761 gttatcccct gattctgtgg ataaccgtat taccgccttt gagtgagctg ataccgctcg
2821 ccgcagccga acgaccgagc gcagcgagtc agtgagcgag gaagc
```

Fig. 30A:

```
LOCUS        pKG64\dT7-pak-3b5'    3525 bp    DNA    circular
SOURCE
  ORGANISM
COMMENT      This file is created by Vector NTI
             http://www.informaxinc.com/
COMMENT      VNTDATE|317130592|
COMMENT      VNTDBDATE|317130593|
COMMENT      VNTNAME|pKG64 dT7-pak-3b5'|
COMMENT      VNTAUTHORNAME|Kaj Grandien|
COMMENT      VNTAUTHORTEL|+49-069-30518706|
COMMENT      VNTAUTHOREML|kaj.grandien@aventis.com|
COMMENT      VNTAUTHORAD1|Aventis Pharma Deutschland GmbH|
COMMENT      VNTAUTHORAD2|Industriepark Hoechst, G879/R020|
COMMENT      VNTAUTHORAD3|D-65926 Frankfurt/M|
COMMENT      VNTAUTHORAD4|Germany|
FEATURES             Location/Qualifiers
     promoter        19..38
                     /vntifkey="30"
                     /label=T7prom\5'
     promoter        complement(957..976)
                     /vntifkey="30"
                     /label=T7prom\3'
     misc_feature    209..382
                     /vntifkey="21"
                     /label=CRIB\domain
     misc_feature    89..876
                     /vntifkey="21"
                     /label=pak-3b\unique\region
BASE COUNT      903 a      896 c      851 g      875 t
ORIGIN
        1 aacctggctt atcgaaatta atacgactca ctataggag accggcagat ctgatatcac
       61 aagtttgtac aaaaaagcag gctcaaaaAT GTCAACTTCA AAAAGTTCCA AGGTGCGAAT
      121 ACGGAATTTC ATCGGGCGAA TCTTCTCTCC CAGCGATAAA GACAAGGATC GAGACGATGA
      181 GATGAAGCCA TCCTCGTCCG CAATGGATAT TAGTCAGCCA TATAACACAG TGCATCGAGT
      241 CCACGTTGGA TACGACGGCC AGAAGTTCAG CGGACTGCCG CAACCATGGA TGGATATTCT
      301 TCTCCGAGAC ATTAGTCTTG CCGATCAGAA GAAGGATCCG AACGCGGTGG TGACTGCGTT
      361 GAAGTTCTAC GCACAATCAA TGAAGGAGAA CGAGAAGACG AAATTCATGA CGACGAATAG
      421 TGTTTTCACG AATAGCGATG ACGATGATGT GGACGTTCAG TTGACCGGAC AAGTCACGGA
      481 ACATTTGAGG AATTTGCAGT GTAGTAATGG TTCCGCAACT TCCCCATCTA CATCAGTGTC
      541 AGCTTCATCT TCTTCTGCTC GTCCACTGAC AAATGGAAAT AATCATCTTT CCACGGCGTC
      601 GTCTACCGAC ACATCTCTCT CATTATCGGA AAGGAATAAC GTTCCGTCTC AGCTCCAGT
      661 TCCATATAGT GAAAGTGCTC CACAACTGAA ACATTCACC GGAGAGACTC CAAAACTGCA
      721 TCCACGATCT CCGTTCCCGC CTCAACCGCC AGTTCTTCCG CAACGAAGCA AAACCGCATC
      781 GGCAGTGGCG ACGACGACGA CGAATCCGAC GACTTCGAAT GGAGCACCAC CACCAGTTCC
      841 TGGATCGAAA GGACCCCCGG TGCCACCGAA ACCATCaccc agctttcttg tacaaagtgg
      901 tgatatcaag cttatcgata ccgtcgacct cgaggggggg cccggtaccc aattcgccct
      961 atagtgagtc gtattacgcg cgctcactgg ccgtcgtttt acaacgtcgt gactgggaaa
     1021 accctggcgt tacccaactt aatcgccttg cagcacatcc cctttcgcc agctggcgta
     1081 atagcgaaga ggcccgcacc gatcgccctt cccaacagtt gcgcagcctg aatggcgaat
     1141 gggacgcgcc ctgtagcggc gcattaagcg cggcgggtgt ggtggttacg cgcagcgtga
     1201 ccgctacact tgccagcgcc ctagcgcccg ctcctttcgc tttcttccct tcctttctcg
     1261 ccacgttcgc cggctttccc cgtcaagctc taaatcgggg gctcccttta gggttccgat
     1321 ttagtgcttt acggcacctc gaccccaaaa aacttgatta gggtgatggt tcacgtagtg
     1381 ggccatcgcc ctgatagacg gttttcgcc ctttgacgtt ggagtccacg ttctttaata
     1441 gtggactctt gttccaaact ggaacaacac tcaaccctat ctcggtctat tcttttgatt
     1501 tataagggat tttgccgatt tcggcctatt ggttaaaaaa tgagctgatt taacaaaaat
     1561 ttaacgcgaa ttttaacaaa atattaacgc ttacaattta ggtggcactt ttcggggaaa
     1621 tgtgcgcgga accctatttt gtttattttt ctaaatacat tcaaatatgt atccgctcat
```

Fig. 30B: (cont'd from Fig. 30A)

```
1681 gagacaataa ccctgataaa tgcttcaata atattgaaaa aggaagagta tgagtattca
1741 acatttccgt gtcgcccttazz ttcccttttt tgcggcattt tgccttcctg tttttgctca
1801 cccagaaacg ctggtgaaag taaaagatgc tgaagatcag ttgggtgcac gagtgggtta
1861 catcgaactg gatctcaaca gcggtaagat ccttgagagt tttcgccccg aagaacgttt
1921 tccaatgatg agcacttta aagttctgct atgtggcgcg gtattatccc gtattgacgc
1981 cgggcaagag caactcggtc gccgcataca ctattctcag aatgacttgg ttgagtactc
2041 accagtcaca gaaaagcatc ttacggatgg catgacagta agagaattat gcagtgctgc
2101 cataaccatg agtgataaca ctgcggccaa cttacttctg acaacgatcg gaggaccgaa
2161 ggagctaacc gcttttttgc acaacatggg ggatcatgta actcgccttg atcgttggga
2221 accggagctg aatgaagcca taccaaacga cgagcgtgac accacgatgc ctgtagcaat
2281 ggcaacaacg ttgcgcaaac tattaactgg cgaactactt actctagctt cccggcaaca
2341 attaatagac tggatggagg cggataaagt tgcaggacca cttctgcgct cggcccttcc
2401 ggctggctgg tttattgctg ataaatctgg agccggtgag cgtgggtctc gcggtatcat
2461 tgcagcactg gggccagatg gtaagccctc ccgtatcgta gttatctaca cgacggggag
2521 tcaggcaact atggatgaac gaaatagaca gatcgctgag ataggtgcct cactgattaa
2581 gcattggtaa ctgtcagacc aagtttactc atatatactt tagattgatt taaaacttca
2641 ttttaatt aaaaggatct aggtgaagat cctttttgat aatctcatga ccaaaatccc
2701 ttaacgtgag ttttcgttcc actgagcgtc agaccccgta gaaaagatca aaggatcttc
2761 ttgagatcct ttttttctgc gcgtaatctg ctgcttgcaa acaaaaaaac caccgctacc
2821 agcggtggtt tgtttgccgg atcaagagct accaactctt tttccgaagg taactggctt
2881 cagcagagcg cagataccaa atactgtcct tctagtgtag ccgtagttag gccaccactt
2941 caagaactct gtagcaccgc ctacatacct cgctctgcta atcctgttac cagtggctgc
3001 tgccagtggc gataagtcgt gtcttaccgg gttggactca agacgatagt taccggataa
3061 ggcgcagcgg tcgggctgaa cggggggttc gtgcacacag cccagcttgg agcgaacgac
3121 ctacaccgaa ctgagatacc tacagcgtga gctatgagaa agcgccacgc ttcccgaagg
3181 gagaaaggcg gacaggtatc cggtaagcgg cagggtcgga acaggagagc gcacgaggga
3241 gcttccaggg ggaaacgcct ggtatcttta tagtcctgtc gggtttcgcc acctctgact
3301 tgagcgtcga ttttgtgat gctcgtcagg ggggcggagc ctatggaaaa acgccagcaa
3361 cgcggccttt ttacggttcc tggccttttg ctggccttt gctcacatgt tctttcctgc
3421 gttatcccct gattctgtgg ataaccgtat taccgccttt gagtgagctg ataccgctcg
3481 ccgcagccga acgaccgagc gcagcgagtc agtgagcgag gaagc
```

Fig. 31A:

```
LOCUS        pKG167\dT7-ced-10    3292 bp    DNA      circular
SOURCE
  ORGANISM
COMMENT      This file is created by Vector NTI
             http://www.informaxinc.com/
COMMENT      VNTDATE|299843316|
COMMENT      VNTDBDATE|317130744|
COMMENT      VNTNAME|pKG167 dT7-ced-10|
COMMENT      VNTAUTHORNAME|Kaj Grandien|
COMMENT      VNTAUTHORTEL|+49-069-30518706|
COMMENT      VNTAUTHOREML|kaj.grandien@aventis.com|
COMMENT      VNTAUTHORAD1|Aventis Pharma Deutschland GmbH|
COMMENT      VNTAUTHORAD2|Industriepark Hoechst, G879/R020|
COMMENT      VNTAUTHORAD3|D-65926 Frankfurt/M|
COMMENT      VNTAUTHORAD4|Germany|
FEATURES             Location/Qualifiers
     promoter        19..38
                     /vntifkey="30"
                     /label=T7prom\5'
     promoter        complement(724..743)
                     /vntifkey="30"
                     /label=T7prom\3'
     misc_feature    136..658
                     /vntifkey="21"
                     /label=ced-10\cDNA\frag\for\RNAi
BASE COUNT       813 a        833 c        825 g        821 t
ORIGIN
        1 aacctggctt atcgaaatta atacgactca ctatagggag accggcagat ctgatatcat
       61 cgatgaattc gagctccacc gcggtggcgg ccgctctaga actagtggat ccccccgggct
      121 gcaggaattc cgcccGTCGG TAAAACGTGT CTCCTGATAT CCTACACCAC AAACGCATTT
      181 CCCGGAGAAT ATATTCCGAC GGTATTCGAC AACTACTCAG CAAATGTGAT GGTCGACGGT
      241 CGGCCGATAA ATCTCGGGCT CTGGGATACA GCTGGACAGG AAGATTACGA TCGACTCCGA
      301 CCACTGTCAT ATCCACAAAC AGACGTGTTT CTCGTATGCT TTGCCCTGAA CAATCCGGCG
      361 AGTTTTGAGA ATGTTCGTGC GAAATGGTAT CCAGAAGTGT CACATCATTG CCCGAATACG
      421 CCGATTATTT TGGTTGGAAC GAAAGCTGAT CTGCGTGAGG ATCGAGATAC TGTTGAACGG
      481 CTCCGCGAAC GCCGGCTCCA ACCAGTGAGC CAAACCCAGG GCTACGTGAT GGCAAAGGAA
      541 ATCAAGGCTG TCAAGTATCT GGAGTGCTCG GCGCTCACGC AACGTGGTCT GAAACAAGTT
      601 TTCGATGAGG CGATCCGAGC CGTGCTCACG CCGCCACAAA GAGCCAAAAA GAGCAAGTgg
      661 gcgaattcga tatcaagctt atcgataccg tcgacctcga ggggggccc ggtacccaat
      721 tcgccctata gtgagtcgta ttacgcgcgc tcactggccg tcgttttaca acgtcgtgac
      781 tgggaaaacc ctggcgttac ccaacttaat cgccttgcag cacatcccc tttcgccagc
      841 tggcgtaata gcgaagaggc ccgcaccgat cgcccttccc aacagttgcg cagcctgaat
      901 ggcgaatggg acgcgcctg tagcggcgca ttaagcgcgg cgggtgtggt ggttacgcgc
      961 agcgtgaccg ctacacttgc cagcgcccta gcgcccgctc ctttcgcttt cttcccttcc
     1021 tttctcgcca cgttcgccgg ctttccccgt caagctctaa atcgggggct ccctttaggg
     1081 ttccgattta gtgctttacg gcacctcgac cccaaaaaac ttgattaggg tgatggttca
     1141 cgtagtgggc catcgccctg atagacggtt tttcgccctt tgacgttgga gtccacgttc
     1201 tttaatagtg gactcttgtt ccaaactgga acaacactca acctatctc ggtctattct
     1261 tttgatttat aagggatttt gccgatttcg gcctattggt taaaaaatga gctgatttaa
     1321 caaaaattta acgcgaattt taacaaaata ttaacgctta catttaggt ggcacttttc
     1381 ggggaaatgt gcgcggaacc cctatttgtt tatttttcta aatacattca aatatgtatc
     1441 cgctcatgag acaataaccc tgataaatgc ttcaataata ttgaaaaagg aagagtatga
     1501 gtattcaaca tttccgtgtc gcccttattc ccttttttgc ggcattttgc cttcctgttt
     1561 ttgctcaccc agaaacgctg gtgaaagtaa aagatgctga agatcagttg ggtgcacgag
     1621 tgggttacat cgaactggat ctcaacagcg gtaagatcct tgagagtttt cgccccgaag
     1681 aacgttttcc aatgatgagc acttttaaag ttctgctatg tggcgcggta ttatcccgta
     1741 ttgacgccgg gcaagagcaa ctcggtcgcc gcatacacta ttctcagaat gacttggttg
     1801 agtactcacc agtcacagaa aagcatctta cggatggcat gacagtaaga gaattatgca
```

Fig. 31B: (cont'd from Fig. 31A)

```
1861 gtgctgccat aaccatgagt gataacactg cggccaactt acttctgaca acgatcggag
1921 gaccgaagga gctaaccgct tttttgcaca acatggggga tcatgtaact cgccttgatc
1981 gttgggaacc ggagctgaat gaagccatac caaacgacga gcgtgacacc acgatgcctg
2041 tagcaatggc aacaacgttg cgcaaactat taactggcga actacttact ctagcttccc
2101 ggcaacaatt aatagactgg atggaggcgg ataaagttgc aggaccactt ctgcgctcgg
2161 cccttccggc tggctggttt attgctgata aatctggagc cggtgagcgt gggtctcgcg
2221 gtatcattgc agcactgggg ccagatggta agccctcccg tatcgtagtt atctacacga
2281 cggggagtca ggcaactatg gatgaacgaa atagacagat cgctgagata ggtgcctcac
2341 tgattaagca ttggtaactg tcagaccaag tttactcata tatactttag attgatttaa
2401 aacttcattt ttaatttaaa aggatctagg tgaagatcct ttttgataat ctcatgacca
2461 aaatccctta acgtgagttt tcgttccact gagcgtcaga ccccgtagaa aagatcaaag
2521 gatcttcttg atcctttt tttctgcgcg taatctgctg cttgcaaaca aaaaaaccac
2581 cgctaccagc ggtggtttgt ttgccggatc aagagctacc aactctttt ccgaaggtaa
2641 ctggcttcag cagagcgcag ataccaaata ctgtccttct agtgtagccg tagttaggcc
2701 accacttcaa gaactctgta gcaccgccta catacctcgc tctgctaatc ctgttaccag
2761 tggctgctgc cagtggcgat aagtcgtgtc ttaccgggtt ggactcaaga cgatagttac
2821 cggataaggc gcagcggtcg ggctgaacgg ggggttcgtg cacacagccc agcttggagc
2881 gaacgaccta caccgaactg agatacctac agcgtgagct atgagaaagc gccacgcttc
2941 ccgaagggag aaaggcggac aggtatccgg taagcggcag ggtcggaaca ggagagcgca
3001 cgagggagct ccaggggga acgcctggt atctttatag tcctgtcggg tttcgccacc
3061 tctgacttga gcgtcgattt ttgtgatgct cgtcagggg gcggagccta tggaaaaacg
3121 ccagcaacgc ggccttttta cggttcctgg ccttttgctg gccttttgct cacatgttct
3181 ttcctgcgtt atccctgat tctgtggata accgtattac cgcctttgag tgagctgata
3241 ccgctcgccg cagccgaacg accgagcgca gcgagtcagt gagcgaggaa gc
```

Fig. 32A:

```
LOCUS       pKG168\dT7-mig-2    3323 bp    DNA    circular
SOURCE
  ORGANISM
COMMENT     This file is created by Vector NTI
            http://www.informaxinc.com/
COMMENT     VNTDATE|299844211|
COMMENT     VNTDBDATE|317130812|
COMMENT     VNTNAME|pKG168 dT7-mig-2|
COMMENT     VNTAUTHORNAME|Kaj Grandien|
COMMENT     VNTAUTHORTEL|+49-069-30518706|
COMMENT     VNTAUTHOREML|kaj.grandien@aventis.com|
COMMENT     VNTAUTHORAD1|Aventis Pharma Deutschland GmbH|
COMMENT     VNTAUTHORAD2|Industriepark Hoechst, G879/R020|
COMMENT     VNTAUTHORAD3|D-65926 Frankfurt/M|
COMMENT     VNTAUTHORAD4|Germany|
FEATURES            Location/Qualifiers
     promoter       19..38
                    /vntifkey="30"
                    /label=T7prom\5'
     promoter       complement(755..774)
                    /vntifkey="30"
                    /label=T7prom\3'
     misc_feature   136..689
                    /vntifkey="21"
                    /label=mig-2\cDNA\frag\for\RNAi
BASE COUNT      826 a      824 c      822 g      851 t
ORIGIN
    1 aacctggctt atcgaaatta atacgactca ctatagggag accggcagat ctgatatcat
   61 cgatgaattc gagctccacc gcggtggcgg ccgctctaga actagtggat ccccccgggct
  121 gcaggaattc cgccctCGAG GCAGATCAAA TGTGTAGTTG TTGGAGACGG AACAGTTGGA
  181 AAAACATGCA TGTTAATATC TTACACAACT GACTCTTTTC CAGTTCAGTA TGTGCCTACA
  241 GTATTTGATA ACTATTCGGC ACAGATGAGT CTTGATGGGA ACGTTGTGAA CTTAGGATTG
  301 TGGGATACTG CTGGACAGGA GGATTATGAT CGTTTACGAC CACTTTCCTA CCCACAGACG
  361 GATGTTTTCA TTCTCTGCTT CTCTGTCGTC TCGCCCGTAT CGTTTGACAA TGTGGCAAGC
  421 AAGTGGATTC CGGAAATACG ACAGCATTGT CCAGATGCGC CTGTCATTCT AGTTGGTACC
  481 AAACTCGATT TGCGCGACGA GGCCGAACCG ATGCGTGCTC TGCAGGCCGA AGGAAAGTCC
  541 CCAATTTCCA AAACGCAAGG CATGAAAATG GCTCAAAAAA TTAAAGCTGT CAAGTATTTG
  601 GAATGCTCTG CATTGACGCA ACAGGGACTC ACACAGGTGT TCGAAGACGC CGTACGGTCC
  661 ATTCTTCATC CGAAACCACA GAAAAGAAg gcgaattcg atatcaagct tatcgatacc
  721 gtcgacctcg agggggggcc cggtacccaa ttcgccctat agtgagtcgt attacgcgcg
  781 ctcactggcc gtcgttttac aacgtcgtga ctgggaaaac cctggcgtta cccaacttaa
  841 tcgccttgca gcacatcccc ctttcgccag ctggcgtaat agcgaagagg cccgcaccga
  901 tcgcccttcc caacagttgc gcagcctgaa tggcgaatgg gacgcgccct gtagcggcgc
  961 attaagcgcg gcgggtgtgg tggttacgcg cagcgtgacc gctacacttg ccagcgccct
 1021 agcgcccgct cctttcgctt tcttcccttc ctttctcgcc acgttcgccg gctttccccg
 1081 tcaagctcta aatcgggggc tccctttagg gttccgattt agtgctttac ggcacctcga
 1141 ccccaaaaaa cttgattagg gtgatggttc acgtagtggg ccatcgccct gatagacggt
 1201 ttttcgccct ttgacgttgg agtccacgtt ctttaatagt ggactcttgt tccaaactgg
 1261 aacaacactc aaccctatct cggtctattc ttttgattta agggattt tgccgatttc
 1321 ggcctattgg ttaaaaaatg agctgattta acaaaaattt aacgcgaatt taacaaaat
 1381 attaacgctt acaatttagg tggcactttt cggggaaatg tgcgcggaac ccctatttgt
 1441 ttatttttct aaatacattc aaatatgtat ccgctcatga caataacc ctgataaatg
 1501 cttcaataat attgaaaaag gaagagtatg agtattcaac atttccgtgt cgcccttatt
 1561 ccctttttg cggcattttg ccttcctgtt tttgctcacc cagaaacgct ggtgaaagta
 1621 aaagatgctg aagatcagtt gggtgcacga gtgggttaca tcgaactgga tctcaacagc
 1681 ggtaagatcc ttgagagttt tcgccccgaa gaacgttttc caatgatgag cacttttaaa
 1741 gttctgctat gtggcgcggt attatcccgt attgacgccg ggcaagagca actcggtcgc
 1801 cgcatacact attctcagaa tgacttggtt gagtactcac cagtcacaga aaagcatctt
```

Fig. 32B: (cont'd from Fig. 32A)

```
1861  acggatggca tgacagtaag agaattatgc agtgctgcca taaccatgag tgataacact
1921  gcggccaact tacttctgac aacgatcgga ggaccgaagg agctaaccgc tttttttgcac
1981  aacatggggg atcatgtaac tcgccttgat cgttgggaac cggagctgaa tgaagccata
2041  ccaaacgacg agcgtgacac cacgatgcct gtagcaatgg caacaacgtt gcgcaaacta
2101  ttaactggcg aactacttac tctagcttcc cggcaacaat taatagactg gatggaggcg
2161  gataaagttg caggaccact tctgcgctcg gcccttccgg ctggctggtt tattgctgat
2221  aaatctggag ccggtgagcg tgggtctcgc ggtatcattg cagcactggg gccagatggt
2281  aagccctccc gtatcgtagt tatctacacg acggggagtc aggcaactat ggatgaacga
2341  aatagacaga tcgctgagat aggtgcctca ctgattaagc attggtaact gtcagaccaa
2401  gtttactcat atatacttta gattgattta aaacttcatt tttaatttaa aaggatctag
2461  gtgaagatcc ttttttgataa tctcatgacc aaaatccctt aacgtgagtt tcgttccac
2521  tgagcgtcag acccgtaga aaagatcaaa ggatcttctt gagatccttt ttttctcgcgc
2581  gtaatctgct gcttgcaaac aaaaaaacca ccgctaccag cggtggtttg tttgccggat
2641  caagagctac caactctttt tccgaaggta actggcttca gcagagcgca gataccaaat
2701  actgtccttc tagtgtagcc gtagttaggc caccacttca agaactctgt agcaccgcct
2761  acataccctcg ctctgctaat cctgttacca gtggctgctg ccagtggcga taagtcgtgt
2821  cttaccgggt tggactcaag acgatagtta ccggataagg cgcagcggtc gggctgaacg
2881  gggggttcgt gcacacagcc cagcttggag cgaacgacct acaccgaact gagataccta
2941  cagcgtgagc tatgagaaag cgccacgctt cccgaaggga gaaaggcgga caggtatccg
3001  gtaagcggca gggtcggaac aggagagcgc acgagggagc ttccaggggg aaacgcctgg
3061  tatctttata gtcctgtcgg gtttcgccac ctctgacttg agcgtcgatt tttgtgatgc
3121  tcgtcagggg gcggagcct atggaaaaac gccagcaacg cggccttttt acggttcctg
3181  gccttttgct ggccttttgc tcacatgttc tttcctgcgt tatcccctga ttctgtggat
3241  aaccgtatta ccgcctttga gtgagctgat accgctcgcc gcagccgaac gaccgagcgc
3301  agcgagtcag tgagcgagga agc
```

Fig. 33:

```
LOCUS           y38f1a.10    1281 bp    DNA
SOURCE
   ORGANISM
COMMENT         This file is created by Vector NTI
                http://www.informaxinc.com/
COMMENT         VNTDATE|317126653|
COMMENT         VNTDBDATE|317126654|
COMMENT         VNTNAME|y38f1a.10|
COMMENT         VNTAUTHORNAME|Kaj Grandien|
COMMENT         VNTAUTHORTEL|069-30518706|
COMMENT         VNTAUTHOREML|kaj.grandien@aventis.com|
COMMENT         VNTAUTHORAD1|Aventis Pharma Deutschland GmbH|
COMMENT         VNTAUTHORAD2|Industriepark Hoechst, G879/R020|
COMMENT         VNTAUTHORAD3|D-65926 Frankfurt/M|
COMMENT         VNTAUTHORAD4|Germany|
COMMENT         VNTEXTCHREPL|Animal/Other Eukaryotic
COMMENT         VNTUDF|Organism|4|C. elegans|
COMMENT         VNTUDF|WWW Source|1|www.wormbase.org|
BASE COUNT       378 a      282 c      314 g       307 t
ORIGIN
        1 atgtttcaaa atagtccgat gatgtacgac tggtggaatg acaccaccaa accgaaacac
       61 cagcagccga cacttaacgt gttgtcacca tggggagcat atttcaatca cattggaaat
      121 gaactgctgc atctgaaaat cgcatcgtcg acagtatcct cgggatgctc gtctccacaa
      181 cagtattcgt ctgctcgatc cgttggtaac tcgctctcca acggcagtgt tgtctccaca
      241 acatcgtcag atggtgatgt gcaattgtcg aataaggaaa attcgaatga caaatcagtt
      301 ggagacaaga atgggaacac caccacaaac aaaacgaccg tcgaaccacc tccaccagaa
      361 gagccacctg ttcgtgttcg agcatctcat cgtgaaaagc tttctgattc cgaagtgctc
      421 aatcaactcc gcgagattgt taatccaagt aatccacttg gaaagtacga gatgaagaag
      481 caaatcggtg ttggagcatc cggaactgta ttcgttgcta atgtggccgg cagcactgat
      541 gtggtggctg tgaagagaat ggctttcaag actcagccga agaaggagat gttgctcacc
      601 gagattaagg ttatgaagca gtatcgacac ccgaacctcg tcaactacat tgaatcgtat
      661 ctggttgatg ctgatgatct ttgggtagtg atggattatc tggaaggtgg aaacttgaca
      721 gatgtcgttg tgaagactga gttggacgaa ggacaaattg cagcagtttt gcaagaatgt
      781 cttaaagcgc ttcacttcct tcatagacac tccatagtgc accgagatat caagagtgac
      841 aacgtgctgc tcggcatgaa cggagaggtt aagctcaccg atatgggatt ctgtgctcag
      901 attcagccgg gatcgaaaag agatactgtc gtcggaactc catattggat gtcgccggag
      961 atattgaaca agaagcagta caactataag gttgacattt ggtcgctggg aattatggct
     1021 ctagagatga ttgatggaga gccaccatat ttgagagaaa ccctttgaa ggctatctac
     1081 ttgattgctc aaaacgggaa gccagagatc aagcaacgcg acagactgtc ttcagagttc
     1141 aacaatttcc ttgacaagtg tcttgttgtt gatccggatc agagagccga tacaacggag
     1201 ctcttggcac atccattcct gaaaaaggcg aagccactct caagcctgat tccatacatc
     1261 agagccgtcc gagaaaagta g
```

Fig. 34:

```
LOCUS       AV196244                 360 bp    mRNA    linear    EST
DEFINITION  AV196244 Yuji Kohara unpublished cDNA:Strain N2 hermaphrodite
            embryo Caenorhabditis elegans cDNA clone yk651h1 5', mRNA
            sequence.
ACCESSION   AV196244
VERSION     AV196244.1  GI:5580015
KEYWORDS    EST.
SOURCE      Caenorhabditis elegans
  ORGANISM  Caenorhabditis elegans
            Eukaryota; Metazoa; Nematoda; Chromadorea; Rhabditida;
            Rhabditoidea; Rhabditidae; Peloderinae; Caenorhabditis.
REFERENCE   1  (bases 1 to 360)
  AUTHORS   Kohara,Y., Shin-i,T., Thierry-Mieg,J., Thierry-Mieg,D.,
            Mitsuki,H.,
            Nishigaki,A., Motohashi,T., Zeng,Q., Watanabe,H., Sugimoto,A.,
            Sano,M., Miyata,A., Mitani,Y., Iida,K., Uesugi,H., Sugiyama,Y.
            and
            Nomoto,H.
  TITLE     Expressed genes in C.elegans
  JOURNAL   Unpublished (1999)
COMMENT     Contact: Yuji Kohara
            Genome Biology Lab.
            National Institute of Genetics
            Yata 1111, Mishima, Shizuoka 411, Japan
            Tel: 81-559-81-6854
            Fax: 81-559-81-6855
            Email: ykohara@lab.nig.ac.jp.
FEATURES             Location/Qualifiers
     source          1..360
                     /organism="Caenorhabditis elegans"
                     /mol_type="mRNA"
                     /strain="N2"
                     /db_xref="taxon:6239"
                     /clone="yk651h1"
                     /sex="hermaphrodite"
                     /dev_stage="embryo"
                     /clone_lib="Yuji Kohara unpublished cDNA:Strain N2
                     hermaphrodite embryo"
ORIGIN
        1 cgacgaaata gtgttttcac gaatagcgat gacgatgatg tggacgttca gttgaccgga
       61 caagtcacgg aacatttgag gaatttgcag tgtagtaatg gttccgcaac ttccccatct
      121 acatcagtgt cagcttcatc ttcttctgct cgtccactga caaatggaaa taatcatctt
      181 tccacggcgt cgtctaccga cacatctctc tcattatcgg aaaggaataa cgttccgtct
      241 ccagctccag ttccatatag tgaaagtgct ccacaactga aaacattcac cggagagact
      301 ccnaaactgc atccacgatc tccgttcccg cctcaaccgc cagttcttcc gcaacgaagc
```

Fig. 35:

```
     LOCUS       AV183453                 300 bp    mRNA    linear
     DEFINITION  AV183453 Yuji Kohara unpublished cDNA:Strain N2 hermaphrodite
                 embryo Caenorhabditis elegans cDNA clone yk651h1 3', mRNA
                 sequence.
     ACCESSION   AV183453
     VERSION     AV183453.1  GI:5563354
     KEYWORDS    EST.
     SOURCE      Caenorhabditis elegans
       ORGANISM  Caenorhabditis elegans
                 Eukaryota; Metazoa; Nematoda; Chromadorea; Rhabditida;
                 Rhabditoidea; Rhabditidae; Peloderinae; Caenorhabditis.
     REFERENCE   1  (bases 1 to 300)
       AUTHORS   Kohara,Y., Shin-i,T., Thierry-Mieg,J., Thierry-Mieg,D.,
     Mitsuki,H.,
                 Nishigaki,A., Motohashi,T., Zeng,Q., Watanabe,H., Sugimoto,A.,
                 Sano,M., Miyata,A., Mitani,Y., Iida,K., Uesugi,H., Sugiyama,Y.
     and
                 Nomoto,H.
       TITLE     Expressed genes in C.elegans
       JOURNAL   Unpublished (1999)
     COMMENT     Contact: Yuji Kohara
                 Genome Biology Lab.
                 National Institute of Genetics
                 Yata 1111, Mishima, Shizuoka 411, Japan
                 Tel: 81-559-81-6854
                 Fax: 81-559-81-6855
                 Email: ykohara@lab.nig.ac.jp.
     FEATURES             Location/Qualifiers
          source          1..300
                          /organism="Caenorhabditis elegans"
                          /mol_type="mRNA"
                          /strain="N2"
                          /db_xref="taxon:6239"
                          /clone="yk651h1"
                          /sex="hermaphrodite"
                          /dev_stage="embryo"
                          /clone_lib="Yuji Kohara unpublished cDNA:Strain N2
                          hermaphrodite embryo"
     ORIGIN
             1 atgtttctgt atattttatg tgaaatgcaa cangaatctt ctagcaaaaa agtacgatgc
            61 tggcaggtag ttgttggggg atggagagaa ggggagaaac aaaacaaaaa tgacaatagg
           121 tgataaaaat nataataatg ttttcgccac agttttcgcg cttaattcac aggaaggttt
           181 tttttttgcat acaataaaat agtgtgaatg ggagagattt ttagagagaa aaaaactaca
           241 aaaaaaacga ggagcaagat ataagggctt gtgtatggta aaacatataa aacgctgtgt
```

Fig. 36:

```
LOCUS           F18A11.4        750 bp      DNA
DEFINITION   possible upstream region of pak-3.
SOURCE
    ORGANISM
COMMENT      This file is created by Vector NTI
             http://www.informaxinc.com/
COMMENT      VNTDBDATE|244402159|
COMMENT      VNTNAME|F18A11.4|
COMMENT      VNTAUTHORNAME|Kaj Grandien|
COMMENT      VNTAUTHORTEL|069-30518706|
COMMENT      VNTAUTHOREML|kaj.grandien@aventis.com|
COMMENT      VNTAUTHORAD1|Aventis Pharma Deutschland GmbH|
COMMENT      VNTAUTHORAD2|Industriepark Hoechst, G879/R020|
COMMENT      VNTAUTHORAD3|D-65926 Frankfurt/M|
COMMENT      VNTAUTHORAD4|Germany|
COMMENT      VNTOAUTHORNAME|UNKNOWN|

BASE COUNT       201 a      196 c      160 g      193 t
ORIGIN
         1 atgaagccat cctcgtccgc aatggatatt agtcagccat ataacacagt gcatcgtctt
        61 gccgatcaga agaaggatcc gaacgcggtg gtgactgcgt tgaagttcta cgcacaatca
       121 atgaaggaga acgagaagac gaaattcatg acgacgaata gtgttttcac gaatagcgat
       181 gacgatgatg tggacgttca gttgaccgga caagtcacgg aacatttgag gaatttgcag
       241 tgtagtaatg gttccgcaac ttccccatct acatcagtgt cagcttcatc ttcttctgct
       301 cgtccactga caaatggaaa taatcatctt tccacggcgt cgtctaccga cacatctctc
       361 tcattatcgg aaaggaataa cgttccgtct ccagctccag ttccatatag tgaaagtgct
       421 ccacaactga aaacattcac cggagagact ccaaaactgc atccacgatc tccgttcccg
       481 cctcaaccgc cagttcttcc gcaacgaagc aaaaccgcat cggcagtggc gacgacgacg
       541 acgaatccga cgacttcgaa tggagcacca ccaccagttc ctggatcgaa aggaccccg
       601 gtgccaccga aaccatcgac ttcagttatc tcttttcgtg agtgttcact gatttgtgtt
       661 ttgatttatg ttgttcgtca aatttgtaga tttgatcttc tcacttccaa gctcggtgca
       721 cattgttcaa actctttgca attctggtag
```

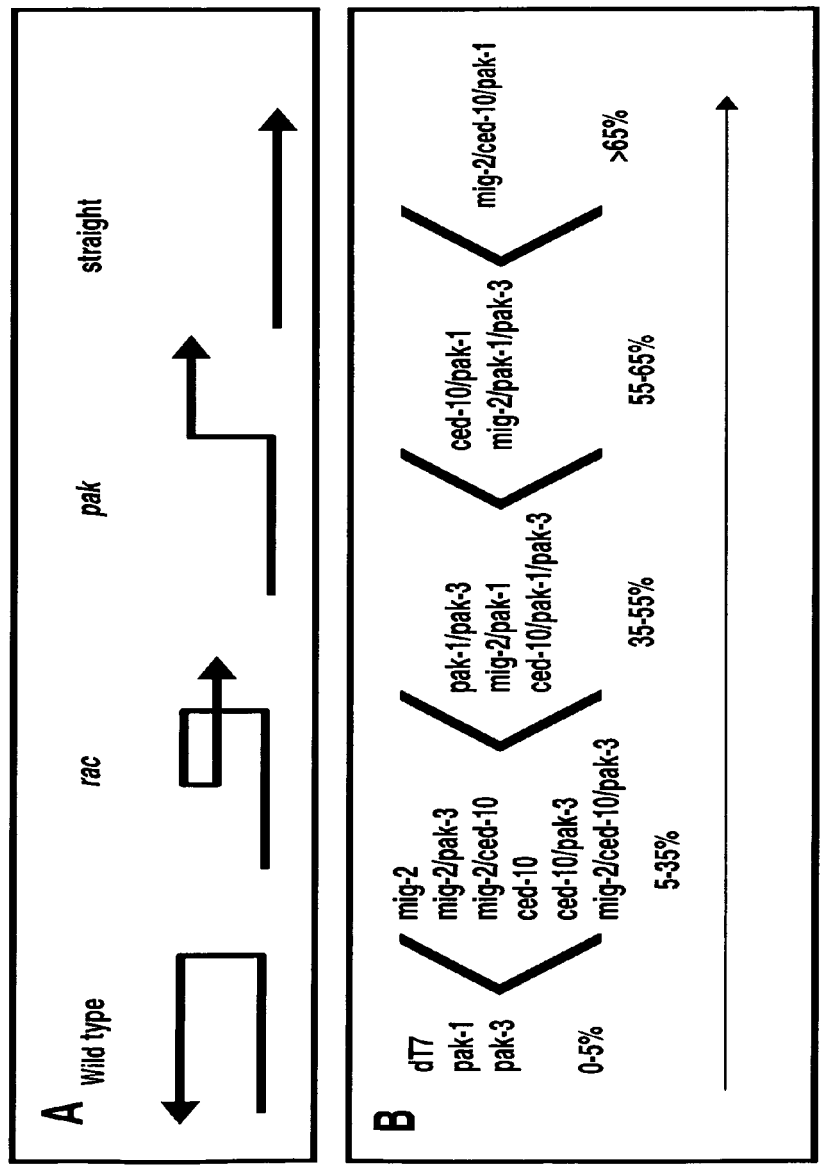
Fig. 37: Gonad pathfinding phenotypes (A) and intensity of gonad defects (B).

US 7,319,024 B1

C. ELEGANS P21-ACTIVATED KINASE (PAK) GENE AND ASSOCIATED LOSS-OF-FUNCTION PHENOTYPES THAT FACILITATE SCREENING FOR SMALL MOLECULE MODULATORS OF PAK ACTIVITY IN THE NEMATODE, CAENORHABDITIS ELEGANS

A novel C. elegans p21-activated kinase (PAK) gene and associated loss-of-function phenotypes that facilitate screening for small molecule modulators of PAK activity in the nematode, Caenorhabditis elegans.

The invention refers to a novel C. elegans p21-activated kinase gene, the pak-3 gene, and associated loss-of-function phenotypes. These phenotypes can be used to elucidate PAK signaling pathways in C. elegans and to screen compounds that modulate PAK signaling.

The p21-activate kinases comprise a group of serine/threonine protein kinases with distinct structural features that have emerged as important regulators of several different cellular and biological processes (reviewed in Bokoch, Annu Rev Biochem 2003. 72:743-81). The PAK family can be subdivided in the PAK 1-3 subclass and the PAK 4-6 subclass (based on the numbering of the human/mammalian PAKs), the former being the focus of interest here. Members of the PAK 1-3 subclass are highly related to the STE20 kinase in yeast, the founding member of this protein class, and homologous have also been identified in other model organisms such as Drosophila and C. elegans.

The two most important structural features of PAKs of the 1-3 class are the highly conserved C-terminal catalytic domain and the N-terminal regulatory domain, respectively. A distinct motif in the regulatory domain of PAK proteins in the CRIB domain (cdc42 and Rac interactive domain), which overlaps with an autoinhibitory domain, keeping the catalytic domain inactive in the absence of stimulatory signals. Other motifs found in PAK proteins are SH3 binding domains and an acidic residue-rich domain between the regulatory domain and the catalytic domain. Additionally a binding site for the Gβγ subunit of heterotrimeric G proteins has been reported to be present in the very C-terminus of PAK.

The most well described activators of PAKs are the Rho class GTPases cdc42 and Rac that upon binding to the CRIB domain block the autoinhibitory domain, leading to activation of the kinase domain. Activation of PAKs can also take place through GTPase independent mechanisms after recruitment of PAKs to the plasma membrane where tyrosine kinase receptor mediated activation occurs. PAKs are known to be activated by phosphorylation, in part through autophosphorylation at Thr423 and Ser144 (numbering according to human PAK1). One kinase that has been shown to phosphorylate Thr423 is PDK1, a 3-phosphinositide dependent kinase.

Many proteins have been reported to be phosphorylated by PAKs, several of those are proteins involved in cell structure and cell motility. It has for example been shown that LIM kinases-1 and -2, serine kinases implicated in actin cytoskeletal dynamics, are phosphorylated by PAKs. Other targets involved in cell motility are myosin light chain kinase and regulatory myosin light chain. In addition PAKs are involved in microtubule dynamics, possibly by phosphorylation of stathmin.

Through their regulatory actions on the actin cytoskeleton, myosin, and microtubules, PAKs are highly involved in cellular processes such as cell motility and cell migration, which on the organism level is manifested as important role(s) for PAKs during e.g. neurogenesis and angiogenesis.

It has also been suggested that PAKs are part of a signaling cascade leading to platelet activation through their regulatory action on actin cytoskeleton dynamics. PAKs are known to have both pro- and antiapoptotic effects, depending on the isoform in question. PAK2 is activated by caspase 3 and is thus part of the apoptotic signaling cascade, whereas it has been reported that PAK1 is activated by certain signaling pathways that promote cell survival, for example by IL-3 signaling.

The important role for PAKs in neurogenesis is exemplified by the hereditary disease nonsyndromic X-linked mental retardation, which is caused by point mutations in PAK3, the brain-specific PAK isoform in humans.

Several studies have suggested that PAKs may play important roles in cancer metastasis. So has it been reported that many breast cancer cell lines express elevated PAK1 and PAK2 activities. It has also been shown that heregulin, a stimulator of cancer cell growth stimulates PAK1 activity. In additional, dominant negative forms of Pak1 can inhibit motility and invasiveness in cancer cell model.

Is has been demonstrated that PAKs can associate with the HIV encoded Nef protein, a protein of central importance in HIV pathogenesis. Together with Nef, PAK appears to promote viral replication an pathogenesis of HIV, and PAK is required for survival of infected cells.

Previous studies have described the existence of one PAK encoding gene in C. elegans, denoted PAK1 (Chen et al 1996 JBC 271, 26362-68, lino & Yamamoto 1998 BBRC 245, 177-84). It was shown by in vitro biochemical assays that PAK1 encodes a bona fide PAK protein demonstrating kinase activity and interaction with CeRac1 (today known as CED-10) and CDC42Ce (CDC-42). Immunoflourescence indicated PAK-1 localization to hypodermal cell boundaries during embryonic body elongation, suggesting a role for pak-1 in embryogenesis. Analysis of transgenic worms expressing pak-1 promoter-reporter gene fusions demonstrated pak-1 expression throughout development, primarily in embryonic tissues, pharyngeal muscles, CAN neurons, motor neurons in the ventral nerve cord, the spermatheca and the distal tip cell (DTC) of the developing gonad. However, no in vivo functional characterization of pak-1 has been reported, even though a knock-out pak-1 strain, RB689, is publicly available. This might suggest that loss-of-function phenotypes of pak-1 are very subtle and hard to detect or that pak-1 is functionally redundant with other protein(s).

C45b11.1 (pak-4)

In addition to the pak-1 gene, one other predicted gene in the C. elegans genome, c45b11.1, appears to encode a PAK protein, which, based on sequence homology, belongs to the PAK 4-6 subclass of PAK proteins. We propose to call this gene pak-4.

Indications of a hitherto unidentified pak gene

Sequence homology searches for genes encoding PAK-like kinase domains identified one open reading frame, y38f1a.10 (SEQ. ID NO. 33), predicted to encode a kinase domain-only protein, without the characteristic regulatory regions of a PAK protein. In the kinase database "kinase.com" located on the world wide web, this ORF is denoted with the name PAK3 with the associated comment that a putative CRIB domain is encoded in a genomic region further upstream. However, no references or experimental data is provided that support this notion.

The invention pertains to an isolated polynucleotide comprising a DNA sequence which is selected from one of the following groups a] a DNA sequence of SEQ ID NO. 1; or
b] a DNA sequence which is complementary to SEQ ID NO. 1; or
c] a DNA sequence which hybridizes to a DNA sequence of SEQ ID NO. 1 or to a DNA sequence which is complementary to SEQ ID NO. 1; or
d] a DNA sequence which is degenerate as a result of the genetic code to the DNA sequence of SEQ ID NO. 1 or to a DNA sequence which is complementary to SEQ ID NO. 1; or
e] a DNA sequence which is encoding a pak-3a polypeptide.

In one embodiment of the invention the isolated polynucleotide consists of a polynucleotide sequence of SEQ ID NO. 1.

In a further embodiment of the invention the pak-3a polypeptide that is encoded by the DNA-sequence is the pak-3a polypeptide of *C. elegans* consisting of an amino acid sequence of SEQ ID NO. 7.

The hybridization can occur under conditions of medium or high stringency. Conditions of medium or high stringent hybridization can be found in textbooks as "Molecular Cloning; edited by Sambrook J. Fritsch E. F., Maniatis T.; Cold Spring Harbor Laboratory Press (ISBN: 0-87969-309-6)"

"Current Protocols in Molecular Biology; edited by Ausubel F. M., Brent R., Kingston R. E., Moore D. D., Seidmann J. G., Smith A., Struhl K., John Wiley & Sons, Inc. (ISBN: 0-471-50338-X-looseleaf)."

Example of hybridization under medium stringency conditions

The DNA or RNA is transferred on to a membrane filter (e.g. nylon, nitrocellulose) via Southern Blot or Northern Blot.

The membrane filter containing the target DNA or RNA (e.g. polynucleotide comprising a sequence of SEQ ID NO. 1) is thoroughly wetted in 6×SSC which is prepared from 20×SSC by dilution with water.

(20×SSC: 0,3 M NaCl, 0,3 M $Na_3$-Citrat.2 $H_2O$).

The membrane filter is then prehybridized by adding 0,2 ml prehybridization solution and incubated at 68° C. for 1-2 hours. The prehybridization solution consists of 6×SSC, 5×Denhardt's reagent, 0,5% SDS and 100 µg/ml denatured, fragmented salmon sperm DNA. 5×Denhardt's reagent is prepared from 100×Denhardt's solution by dilution with water.

(100×Denhardt's solution: 10 g Ficoll 400 and 10 g Polyvinylpyrollidone and 10 g Bovine Serum Albumin in 500 ml water).

To the prehybridization mix 10-20 µg/ml of radiolabeled probe (specific activity for example=$10^9$ cpm/µg) is added.

If the radiolabeled probe is double stranded, it has to be denatured by heating for 5 min. at 100° C. followed by rapid chilling to between 0° C. to 10° C.

The hybridization mix is incubated for 2 to 14 hours at 60° C. After hybridization the membrane filter is first washed in
2×SSC containing 0,5% SDS for 5 minutes at room temperature.
The filter is then washed in
2×SSC containing 0,1% SDS for 15 minutes at room temperature.
The filter is then washed in
0,1% SSC containing 0,5% SDS for 30 minutes at 37° C.
the filter is then washed in
0,1×SSC containing 0,5% SDS for 30 minutes at 42° C.

After this washing steps the filter is exposed e.g. to X-ray film or is analyzed by a phosphoimager (applied Biosystems).

Example of hybridization under high stringency conditions

The medium and high stringency conditions differ in particular with respect to the temperature and composition of the washing steps. Whereas the prehybridization and incubation with the radiolabeled probe is performed under the same conditions as in case of medium stringent hybridization the washing steps under stringent hybridization are as follows:

The membrane filter is first washed in 2×SSC and 0,5% SDS for 5 minutes at room temperature.
The filter is then washed in 2×SSC containing 0,1% SDS for 30 min at 50° C.
The filter is then washed in 0,1×SSC containing 0,1% SDS for 30 min at 60° C.
This last washing step is repeated one more time before the filter is exposed to a X-ray film or analyzed by a phospho imager.

In another embodiment the invention concerns an isolated polynucleotide comprising a DNA sequence that is selected from one of the following groups a] a DNA sequence of SEQ ID No. 2, 3, 4, 5 or 6; or
b] a DNA sequence which is complementary to one of the DNA sequences of SEQ ID NO. 2, 3, 4, 5 or 6; or
c] a DNA sequence which hybridizes to at least one DNA sequence of SEQ ID NO. 2, 3, 4, 5 or 6 or to at least one DNA sequence which is complementary to a DNA sequence of SEQ ID NO. 2, 3, 4, 5 or 6; or
d] a DNA sequence which is degenerate as a result of the genetic code to at least one DNA sequence of SEQ ID NO. 2, 3, 4, 5 or 6; or
e] a DNA sequence which is encoding a pak-3b polypeptide.

In one embodiment of the invention the isolated polynucleotide consists of a polynucleotide sequence of SEQ ID NO. 2, 3, 4, 5 or 6.

In a further embodiment of the invention the pak-3b polypeptide that is encoded by the DNA sequence is the pak-3b polypeptide of *C. elegans* consisting of an amino acid sequence of SEQ ID NO. 8, 9, 10, 11 or 12.

With respect to the hybridization of a polynucleotide to a pak-3b specifying sequence reference is made to the conditions as drafted aforementioned in context of pak-3a. The conditions as specified for pak-3a are just as applicable for pak-3b.

The invention refers in a further embodiment to a recombinant vector sequence comprising a DNA sequence selected from one of the following groups a] a DNA sequence of one of the SEQ ID NO. 13, 14, 15, 16, 17 or 18; or
b] a DNA sequence which hybridizes to one of the SEQ ID NO. 13, 14, 15, 16, 17 or 18.

The conditions for hybridization as specified for pak-3a are applicable for a DNA sequence that hybridizes to one of the SEQ ID NO. 13, 14, 15, 16, 17 or 18 as well.

The invention refers in a further preferred embodiment to a vector sequence that consists of a DNA sequence of one of the SEQ ID NO. 13, 14, 15, 16, 17 or 18.

The invention refers also to a host cell containing a recombinant vector system as specified in SEQ ID NO. 13, 14, 15, 16, 17 or 18.

A host cell may be any cell that is transformable by a vector sequence. Examples of host cells are: *Escherichia coli, Bacillus subtilis, Saccharomyces cerevisiae*, insect cells, mammalian cell lines (NIH 3T3; COS; Hela etc.) and others.

A further embodiment of the invention refers to an isolated protein that is encoded by a polynucleotide sequence of SEQ ID NO. 1. This isolated protein can consist of an amino acids sequence of SEQ ID NO. 7. This isolated protein can exhibit the activity of a pak-3a protein.

A further embodiment of the invention refers to an isolated protein that is encoded by a polynucleotide sequence of SEQ ID NO. 2, 3, 4, 5 or 6. Such an isolated protein can consists of an amino acid sequence of SEQ ID NO. 8, 9, 10, 11 or 12. This isolated protein can exhibit the activity of a pak-3b protein.

The invention refers also to the use of a host cell containing a recombinant vector system of SEQ ID NO. 13, 14, 15, 16, 17 or 18 for manufacturing of a protein having an amino acid sequence of SEQ ID NO. 7 and/or exhibiting the activity of a pak-3a protein or for manufacturing of a protein having an amino acid sequence of SEQ ID NO. 8, 9, 10, 11 or 12 and/or exhibiting the activity of a pak-3b protein.

In a further embodiment the invention refers to the use of a host cell containing a recombinant vector system of SEQ ID NO. 13, 14, 15, 16, 17 or 18 in a screening assay for identifying of a compound which interacts with a pak-3a protein or a pak-3b protein. When a compound interacts with a protein in context of the present invention it shall mean that the compound binds to the protein, or that it stimulates the activity of the protein (activation), or it diminishes the activity of the protein (inhibition), or it maintains the activity of the protein, or it stabilizes the acting of the protein.

The invention concerns further the manufacturing of a protein having an amino acid sequence of SEQ ID NO. 7, 8, 9, 10, 11 or 12 and/or exhibiting the activity of a pak-3a or pak-3b protein by cultivation of host cell which harbors a recombination vector sequence of SEQ ID NO. 13, 14, 15, 16, 17 or 18, after cultivation the separation of the cells from cultivation medium, thereafter the lysis of the cells and the purification of the protein by means of protein purification techniques. A person skilled in the art will get access to all required protocols for performing such a method for manufacturing of the protein starting from cultivation of the cells up to the purification of the protein in a text book such as "Current Protocols in Protein Science; edited by Coligan J. E., Dunn B. M., Ploegh H. L., Speicher D. W., Wingfield P. T.; Wiley, John & Sons, Inc. (ISBN: 0471140988)".

In a further embodiment the invention refers to the use of a protein having an amino acid sequence of SEQ ID NO. 7, 8, 9, 10, 11 or 12 and/or exhibiting the activity of a pak-3a or pak-3b protein to the preparation of an antibody which exhibits binding specificity for such a protein.

In a further embodiment the invention pertains to the use of a protein having an amino acid sequence of SEQ ID NO. 7, 8, 9, 10, 11 or 12 and/or exhibiting the activity of a pak-3a or pak-3b protein the preparation of a medicament for therapy of a disease which is caused by a deficiency, hyperactivation, or malfunction of a mammalian analogous protein of a pak-3a and/or pak-3 protein. Such a mammalian analogous protein may be derived from the human species. It can consist of a kinase protein. The disease involved may be related to a malfunction of the central nervous system, of metabolism, of the cardiovascular system, of the cell division process, or of other cellular or systemic processes.

The invention refers further to the use of a protein having an amino acid sequence of SEQ ID NO. 7, 8, 9, 10, 11 or 12 in a screening process for identifying of a compound that interacts with a pak-3a or a pak-3b protein. Such a screening process can be organized in form of a High-Throughput-Screening (HTS). The HTS is based upon automized screening formats by means of laboratory robot systems.

An embodiment of the invention refers to an assay for identifying of a compound that is interacting with a pak-3a and/or a pak-3b protein wherein
  a] a pak-3a and/or a pak-3b protein is provided,
  b] a chemical compound is provided,
  c] the pak-3a and/or the pak-3b protein and the chemical compound are brought in contact,
  d] the binding of the chemical compound to the pak-3a and/or pak-3b protein is determined and/or the activity of the pak-3a and/or pak-3b protein is determined.

The pak-3a or pak-3b protein can consist of a protein having an amino acid sequence of SEQ ID NO. 7, 8, 9, 10, 11 or 12. A chemical compound can be provided by means of a chemical synthesis performed in a chemist's laboratory or by an industrial process. A chemical compound can be further provided by isolation from a biological organism (e.g. bacterium, fungus, plant, mammal etc.).

The pak-3a or pak-3b protein can be provided in form of a host cell which harbors a recombinant vector of SEQ ID NO. 13, 14, 15, 16, 17 or 18 and expresses a protein having the activity of a pak-3a or pak-3b protein. In one embodiment of the invention such a host cell is brought in contact with the chemical compound. In a further embodiment of the invention the assay is used for identifying a compound that is inactivating, or activating, or binding, or maintaining the activity of a pak-3a and/or pak-3b protein.

The invention concerns further a compound that can be identified by such an assay as well as the use of such a compound as pharmaceutically active ingredient or the use of such a compound for manufacturing of a medicament. Such a compound may consist of a molecular weight of 100 to 50 000 kDa.

The invention pertains in a further embodiment to a strain of *C. elegans* that is exhibiting a loss-of-function phenotype with respect to the pak-3a and/or pak-3b protein. Such a loss-of-function phenotype is detectable by means of southern or northern blots in case the gene and/or the mRNA is not expressed. The loss-of-function phenotype is also detectable by western blots in case the protein is not expressed. The determination of the activity of the pak-3a or pak-3b protein proves the loss-of-function phenotype with respect to the pak-3a and/or pak-3b protein in case the organism is not able to produce functional versions of the proteins, or is degrading the proteins rapidly or contains inhibitors of the proteins.

The loss-of-function phenotype of a *C. elegans* strains with respect to the pak-3a and/or pak-3b protein can be linked to gonad migration, embryonic lethality or sterility.

In one embodiment of the invention the loss-of-function phenotype of the strain of *C. elegans* is caused by a mutation or by a partly or complete deletion of the gene coding sequence of pak-3a and/or pak-3b.

In a further embodiment of the invention the loss-of-function phenotype of the strain of *C. elegans* is causes by an insertion of a polynucleotide sequence into the gene coding sequence of pak-3a and/or pak-3b.

In a further embodiment of the invention the loss-of-function phenotype of the strain of *C. elegans* is caused by a polynucleotide that is selected from the following group:

RNAi; (interference RNA), Ribozyme, antisense RNA, antisense DNA.

The inactivation of specific mRNAs upon exposure to double-stranded RAN (dsRNA) can in *C. elegans* be achieved by several different approaches. Below is a short summary of the main approaches.

By feeding

In RNAi by feeding a cDNA or genomic DNA fragment from the gene of interest is cloned in a plasmid between two opposing T7 RNA polymerase promoter sites. The plasmid is subsequently transformed in to an *E. coli* host strain that contains an inducible T7 RNA polymerase gene and the *E. coli* strain obtained is used as a *C. elegans* food source (Timmons and Fire, 1998, Nature, 395, 854; Timmons et al, 2001, Gene 263, 103-112; Kamath et al, 2002, Genome Biology 2, research0002.1-0002.10research0002.1-0002.10).

The advantage of this approach is that relative large numbers of worms can be treated for RNAi and that over several generations. One disadvantage is that some RNAs might be toxic to the *E. coli*. Normally phenotypes are scored initially in the F1 generation, although some phenotypes occasionally can be observes already in the P0 animals.

By microinjection

The first described approach for RNAi in *C. elegans* was the microinjection of dsRNA into the animal body cavity (Fire et al, 1998, Nature 391, 801-811). For this approach dsRNA is obtained by in vitro transcription of a cDNA or genomic DNA fragment cloned into a vector with T3, T7 or SP6 RNA polymerase promoter sites, or from a hybrid PCR product containing both suitable RNA polymerase promoter site(s) and sequence from the gene of interest. Normally the two RNA strands are transcribed separately and subsequently annealed together. Alternatively both strands can be transcribed in one reaction (if the insert has been cloned in both orientations downstream of the same promoter), meaning that a separate annealing stap can be left out. The in vitro produced dsRNA is subsequently microinjected into the body of *C. elegans* animals.

With this approach the number of animals available for analysis is much lower than the feeding method. However, it has occasionally been claimed that microinjection has a higher success rate.

By soaking

Instead of microinjecting the in vitro transcribed dsRNA tha worms can be incubated ("soaked") in high concentrations of dsRNA (Maeda et al 2001, Current Biology, 11, 171-176).

This approach is less labour intensive than microinjection but is not so commonly used.

By Transgenics

DsRNA can also be produced in situ in the worms by generating transgenic animals expressing either a hairpin RNA molecule that fold on itself to a dsRNA, or by the use of two transgenic constructs expressing the two different RNA strands. Although labour intensive, this approach opens the possibility for stably knocked-down RNAs as well as tissue-specific and inducible RNAi, depending on the promoter chosen for driving the RNA expression (Tavernakis et al, 2000, Nature Genetics, 24, 180-183).

In a further embodiment of the invention the loss-of-function phenotype of the strain of *C. elegans* is caused by an inhibitor of the pak-3a and/or pak-3b protein.

The invention refers also to the use of a strain of *C. elegans* that is exhibiting a loss-of-function phenotype for identifying of a protein of the PAK signaling pathway. Such a protein can be a kinase, a phosphates, a transcription enhancer, a transcription repressor or any other protein which is able to interact with a intercellular signaling cascade.

The invention refers further to the use of a strain that is exhibiting a loss-of-function phenotype for identifying a compound that interacts with a protein of the PAK signaling pathway.

The invention further pertains to a method for generating a *C. elegans* having a phenotype that is characterized by sterility and/or embryonic lethality and/or a defective gonad migration pattern in by a] inactivating the pak-1 gene and/or pak-1 protein in a *C. elegans* and/or inactivating the pak-3 gene and/or pak-3 protein of the same *C. elegans* and b] identifying of a *C. elegans* exhibiting the phenotype of sterility and/or embryonic lethality and/or a defective gonad migration pattern.

In context of this application the term pak-3 shall include pak-3a and pak-3b. When referring to pak-3 the reference shall pertain to pak-3a and/or pak-3b. The inactivating of the pak-1 gene and/or pak-1 protein and pak-3 gene and/or pak-3 protein has to be performed in the same *C. elegans* organisms. The inactivating of both genes could occur simultaneously at the same time or consecutively one after another. In all cases of inactivation of pak-1 and/or pak-1 to obtain the loss of function phenotype it makes no difference whether the chemical inhibition and/or genetic inactivation of pak-3 is performed before or subsequently after the chemical inhibition and/or genetic inactivation of pak-1.

The identifying of a *C. elegans* exhibiting the phenotype of sterility and/or embryonic lethality and/or a defective gonad migration pattern can occur in offsprings of the F1 and/or the F2 and/or a further following generation.

The inactivating of the pak-1 gene and/or the pak-1 protein can be achieved by means of RNA molecules that are suitable for RNA interference with a pak-1 coding polynucleotide. Such RNA molecules can be derived from at least one of the vectors of the following group: pKG61 (SEQ ID NO. 26), pKG71 (SEQ ID NO. 28). For that purpose the according vector is introduced into a bacterial strain as e.g. *E. coli*, the RNA is transcribed from the plasmid promoter and thereafter isolated from the bacteria and purified. The purified RNA is then brought in contact with a cell of *C. elegans*, or a part of an organism of *C. elegans* or a complete organism of *C. elegans*.

A further possibility of inactivating the pak-1 gene and/or the pak-1 protein consists in feeding bacteria to *C. elegans* which bacteria contains RNA molecules which are suitable for RNA interference with a pak-1 coding polynucleotide. Such bacteria for the feeding of the *C. elegans* can harbor at least one plasmid of the following group: pKG61 (SEQ ID NO. 26), pKG71 (SEQ ID NO. 28). The RNA is transcribed from these vectors within the bacteria.

The inactivating of the pak-1 gene and/or the pak-1 protein can be performed by use of a pak-1 knock out strain of *C. elegans*. Such a knock out strain is e.g. *C. elegans* RB 689.

The pak-1 gene and/or pak-1 protein can be inactivated by means of an according antisense RNA, antisense DNA, a Ribozyme, an inhibitor of the pak-1 gene transcription or an inhibitor of the pak-1 protein.

The inactivating of the pak-3 gene and/or pak-3 protein can be achieved by means of RNA molecules that are suitable for RNA interference with a pak-3 coding polynucleotide. Such RNA molecules can be derived from at least one of the vectors of the following group: pKG65 (SEQ ID NO. 27), pKG71 (SEQ ID NO. 28), pKG63 (SEQ ID NO. 29), pKG64 (SEQ ID NO. 30). For that purpose the according vector is introduced into a bacterial stain as e.g. *E. coli*, the RNA transcribed from the plasmid promoter and thereafter isolated from the bacteria and purified. The purified RNA is then brought in contact with a cell of *C. elegans*, or part of an organism of *C. elegans* or a complete organism of *C. elegans*. A further possibility of inactivating the pak-3 gene and/or the pak-3 protein consists in feeding to *C. elegans* which bacteria contain RNA molecules which are suitable for RNA interference with a pak-3 coding polynucleotide. Such bacteria for the feeding of the *C. elegans* can harbor at least one plasmid of the following group: pKG65 (SEQ ID NO. 27), pKG71 (SEQ ID NO. 28), pKG63 (SEQ ID NO. 29), pKG64 (SEQ ID NO. 30). The RNA is transcribed from these vectors within the bacteria. The inactivating of the pak-3 gene and/or pak-3 protein can be performed by use of a pak-3 knock out strain of *C. elegans*. The pak-3 gene and/or pak-3 protein can be inactivated by means of an according antisense RNA, antisense DNA, a Ribozyme, an inhibitor of the pak-3 gene transcription or an inhibitor of the pak-3 protein.

The invention pertains further to a strain of *C. elegans* which is characterized by a phenotype of sterility and/or embryonic lethality and/or a defective gonad migration and which harbors an inquired or missing pak-1 function and an impaired or missing pak-3 function. In context of this application the term function shall refer to the gene and/or the protein. The strain of *C. elegans* of the invention which is characterized by a phenotype of sterility and/or embryonic lethality and/or a defective gonad migration pattern could be obtainable or could be obtained by one or several of the methods for generating a *C. elegans* having said phenotypes. Such a strain can be used amongst other things for characterizing the intercellular signaling cascade linked to pak-1 and/or pak-3. Such a strain can also be used for identifying of a compound that interferes with one or several proteins which are part of the signaling cascade linked to pak-1 and/or pak-3. Such a strain can further be used for identification of a compound that interferes with transcription of one or several proteins that are part of the signaling cascade linked to pak-1 and/or pak-3.

The invention relates also to manufacturing of a RNA molecule wherein at least one of the polynucleotides of pKG61 (SEQ ID NO. 26), pKG65 (SEQ ID NO. 27), pKG71 (SEQ ID NO. 28), pKG63 (SEQ ID NO. 29), pKG64 (SEQ ID NO. 30), pKG167 (SEQ ID NO. 31) or pKG168 (SEQ ID NO. 32) is transformed into a bacterial strain, the RNA is transcribed from the vector and the transcribed RNA is isolated and/or purified. The invention pertains also to RNA molecules that are obtainable or obtained by such a method. These RNA molecules can be used as individual species one by one or in a combined manner for RNA interference with a pak-1 and/or pak-3 protein coding polynucleotide.

DESCRIPTION OF SEQ IDS

SEQ ID NO. 1 is disclosing the polynucleotide sequence of the pak-3 cDNA. The pak-3a gene is consisting of the coding information of a kinase domain.

SEQ ID NO. 2 is disclosing the polynucleotide sequence of the pak-3b cDNA. The pak-3b gene is consisting of the coding information of a kinase domain of the same sequence composition as pak-3a and a additional CRIB domain (cdc42/Rac interactive binding domain) which is 5'-linked to the kinase domain.

SEQ ID NO. 3 is disclosing the polynucleotide sequence of the pak-3b cDNA harboring a silent polymorphism (change from gct to gcc) that would leave the concerned Ala of the corresponding protein unchanged.

SEQ ID NO. 4 is disclosing the polynucleotide sequence of the pak-3b cDNA harboring the silent polymorphism as described in SEQ ID NO. 3 and harboring further a in frame 6 bp insertion within the kinase domain.

SEQ ID NO. 5 is disclosing the polynucleotide sequence of the pak-3b cDNA harboring an in frame 9 bp insert within the CRIB domain and having the corresponding sequence of Exon 7 deleted.

SEQ ID NO. 6 is disclosing the polynucleotide sequence of the pak-3b cDNA harboring a polymorphism (change from atc to gtc) within the CRIB domain which changes an Ile into a Val of the corresponding protein and harboring the in frame insertion of 6 bp of the kinase domain (as is the same as in SEQ ID NO. 4).

SEQ ID NO. 7 is disclosing the amino acid sequence of the corresponding protein of SEQ ID NO. 1 (kinase domain).

SEQ ID NO. 8 is disclosing the amino acid sequence of the corresponding protein of SEQ ID NO. 2 (kinase domain plus CRIB domain).

SEQ ID NO. 9 is disclosing the amino acid sequence of the corresponding protein of SEQ ID NO. 3 (kinase domain plus CRIB domain).

SEQ ID NO. 10 is disclosing the amino acid sequence of the corresponding protein of SEQ ID NO. 4 (kinase domain having a 6 bp insert plus CRIB domain).

SEQ ID NO. 11 is disclosing the amino acid sequence of the corresponding protein of SEQ ID NO. 5 (kinase domain plus CRIB domain having a 9 bp insert and Exon 7 deleted).

SEQ ID NO. 12 is disclosing the amino acid sequence of the corresponding protein of SEQ ID NO. 6 (kinase domain having a 6 bp insert plus CRIB domain in which Ile is changed into a Val).

SEQ ID NO. 13 is disclosing the polynucleotide sequence of vector pKG40, which is encompassing the polynucleotide sequence of SEQ ID NO. 1. A description of the vector is given within the header of FIG. 13.

SEQ ID NO. 14 is disclosing the polynucleotide sequence of vector pKG 123, which is encompassing the polynucleotide sequence of SEQ ID NO. 2. A description of the vector is given within the header of FIG. 14.

SEQ ID NO. 15 is disclosing the polynucleotide sequence of vector pKG 43, which is encompassing the polynucleotide sequence of SEQ ID NO. 3. A description of the vector is given within the header of FIG. 15.

SEQ ID NO. 16 is disclosing the polynucleotide sequence of vector pKG 44, which is encompassing the polynucleotide sequence of SEQ ID NO. 4. A description of the vector is given within the header of FIG. 16.

SEQ ID NO. 17 is disclosing the polynucleotide sequence of vector pKG 58, which is encompassing the polynucleotide sequence of SEQ ID NO. 5. A description of the vector is given within the header of FIG. 17.

SEQ ID NO. 18 is disclosing the polynucleotide sequence of vector pKG 59, which is encompassing the polynucleotide sequence of SEQ ID NO. 6. A description of the vector is given within the header of FIG. 18.

SEQ ID NO. 19 is disclosing the primer sequence kg 1.
SEQ ID NO. 20 is disclosing the primer sequence kg 2.
SEQ ID NO. 21 is disclosing the primer sequence kg 25.
SEQ ID NO. 22 is disclosing the primer sequence kg 26.
SEQ ID NO. 23 is disclosing the primer sequence kg 37.
SEQ ID NO. 24 is disclosing the primer sequence kg 27.
SEQ ID NO. 25 is disclosing the primer sequence kg 50.
SEQ ID NO. 26 is disclosing the polynucleotide sequence of vector pkG61/dT7-pak-1. A description of the vector is given within the header of FIG. 26.
SEQ ID NO. 27 is disclosing the polynucleotide sequence of vector pkG65/dT7-pak-3 . A description of the vector is given within the header of FIG. 27.
SEQ ID NO. 28 is disclosing the polynucleotide sequence of vector pkG 71/dT7-pak-3/pak-1. A description of the vector is given within the header of FIG. 28.
SEQ ID NO. 29 is disclosing the polynucleotide sequence of vector pkG63/dT7-pak-3a. A description of the vector is given within the header of FIG. 29.
SEQ ID NO. 30 is disclosing the polynucleotide sequence of vector pkG64/dT7-pak-3b. A description of the vector is given within the header of FIG. 30.
SEQ ID NO. 31 is disclosing the polynucleotide sequence of vector pkG167/dT7-ced-10. A description of the vector is given within the header of FIG. 31.
SEQ ID NO. 32 is disclosing the polynucleotide sequence of vector pkG168/dT7-mig-2. A description of the vector is given within the header of FIG. 32.
SEQ ID NO. 33 is disclosing the polynucleotide sequence of expressed sequence tag (EST) y38f1a.10 of C. elegans.
SEQ ID NO. 34 is disclosing the polynucleotide sequence of EST yk65141 5' of C. elegans.
SEQ ID NO. 35 is disclosing the polynucleotide sequence of EST yk65141 3' of C. elegans.
SEQ ID NO. 36 is disclosing the polynucleotide sequence of EST F18a 11.4 of C. elegans.

DESCRIPTION OF THE FIGURES

FIG. 1 exhibits SEQ ID NO. 1.
FIG. 2 exhibits SEQ ID NO. 2.
FIG. 3 exhibits SEQ ID NO. 3.
FIG. 4 exhibits SEQ ID NO. 4.
FIG. 5 exhibits SEQ ID NO. 5.
FIG. 6 exhibits SEQ ID NO. 6.
FIG. 7 exhibits SEQ ID NO. 7.
FIG. 8 exhibits SEQ ID NO. 8.
FIG. 9 exhibits SEQ ID NO. 9.
FIG. 10 exhibits SEQ ID NO. 10.
FIG. 11 exhibits SEQ ID NO. 11.
FIG. 12 exhibits SEQ ID NO. 12.
FIG. 13A and B exhibits SEQ ID NO. 13.
FIG. 14A and B exhibits SEQ ID NO. 14.
FIG. 15A and B exhibits SEQ ID NO. 15.
FIG. 16A and B exhibits SEQ ID NO. 16.
FIG. 17A and B exhibits SEQ ID NO. 17.
FIG 18A and B exhibits SEQ ID NO. 18.
FIG. 19 exhibits SEQ ID NO. 19.
FIG. 20 exhibits SEQ ID NO. 20.
FIG. 21 exhibits SEQ ID NO. 21.
FIG. 22 exhibits SEQ ID NO. 22.
FIG. 23 exhibits SEQ ID NO. 23.
FIG. 24 exhibits SEQ ID NO. 24.
FIG. 25 exhibits SEQ ID NO. 25.
FIG. 26A and B exhibits SEQ ID NO. 26.
FIG. 27A and B exhibits SEQ ID NO. 27.
FIG. 28A and B exhibits SEQ ID NO. 28.
FIG. 29A and B exhibits SEQ ID NO. 29.
FIG. 30A and B exhibits SEQ ID NO. 30.
FIG. 31A and B exhibits SEQ ID NO. 31.
FIG. 32A and B exhibits SEQ ID NO. 32.
FIG. 33 exhibits SEQ ID NO. 33.
FIG. 34 exhibits SEQ ID NO. 34.
FIG. 35 exhibits SEQ ID NO. 35.
FIG. 36 exhibits SEQ ID NO. 36.
FIG. 37 Gonad path finding phenotypes (A) and intensing of gonad defects.

| Abbreviations | |
| --- | --- |
| NGM | Nematode growing medium |
| E. coli OP50 | Uracil requiring strain of E. coli; used as a food source for nematodes |
| DMSO | Dimethylsulfoxide. |

Deposit of plasmid DNA

The plasmids of the present invention have been deposited with the DSMZ—Deutsche Sammlung von Mikroorganismen und Zellkulturen GmbH
(German Collection of Microorganisms and Cell Cultures GmbH)
Mascheroder Weg 1 b
D-38124 Braunschweig
according to the following numbers:
  plasmid pKG40=DSM 16147 (see also SEQ ID NO. 13 as well as FIG. 13)
  plasmid pKG43=DSM 16148 (see also SEQ ID NO. 15 as well as FIG. 15)
  plasmid pKG44=DSM 16149 (see also SEQ ID NO. 16 as well as FIG. 16)
  plasmid pKG58=DSM 16150 (see also SEQ ID NO. 17 as well as FIG. 17)
  plasmid pKG59=DSM 16151 (see also SEQ ID NO. 18 as well as FIG. 18)
  plasmid pKG123=DSM 16152 (see also SEQ ID NO. 14 as well as FIG. 14)

EXAMPLES

Strains, general strain culture, molecular & genetic methods
  Nematode culture was done according to Brenner 1974.
  Strains were obtained from the C. elegans Genomics Center (CGC) and the C. elegans knock out consortium.

Cloning of pak-3
  The different isoforms of pak-3 cDNA were cloned by RT-PCR from N2 (C. elegans wild-type) total RNA. All primers contain 5'adaptor sequences to allow Gateway cloning. RT-PCR products with 5' Gateway adaptor sequences were re-amplified using AttB sequence primers

```
                                              (SEQ ID NO. 19)
    kg1; GGGGACAAGTTTGTACAAAAAAGCAGGCT, (SEQ ID NO. 20)
    kg2; GGGGACCACTTTGTACAAGAAAGCTGGGT,
``` and cloned via the BP reaction into the vector pDONR201 as described by the manufacturer (Invitrogen).
  Sequence alignments were done using the Lasergene software package. Blast database searches were conducted using the NCBI Blast tool (internal installation). Sequence motifs were identified using the Workbench Pfam HMM database search tool (GeneData AG).

pKG40 (pak-3a wild-type; DSM 16147) was cloned by the use of gene-specific primers based on the gene prediction for y38f1a.10, (SEQ ID NO. 33). (5': kg25; aaaaagcaggct-caaaaATGTTTCAAAATAGTCCGATGAT (SEQ ID NO. 21; 3': kg26; agaaagctgggtCTACTTTTCTCGGACG-GCTCT, SEQ ID NO. 22). (One pak-3a clone was isolated by the 5' SL1 primer kg37 [see below] in combination with kg26. This clone was found to have an ORF identical to pKG40 and was not kept).

pKG43 (pak-3b SL 1 t1680c; Ala-Ala; DSM 16148) was cloned by a 5' primer corresponding to the SL1 trans-spliced leader sequence (kg37; aaaaagcaggctGGTTTAATTAC-CAAGTTTGAG, SEQ ID NO. 23) in conjunction with the 3' primer kg26 (agaaagctgggtcTACTTTTCTCGGACG-GCTCT, SEQ ID NO. 24).

pKG44 (pak-3b Ins1581 t1686c; DSM 16149), pKG58 (pak-3b Ins228 Deta Exon 7) and pKG59 (pak-3b a43g Ins1581) were all cloned by combining a gene-specific 5' primer, kg50 (aaaaagcaggctcaaaaATGTCAACT-TCAAAAAGTTCCAAG, SEQ ID NO. 25), derived from the sequence information from pKG43, with the 3' primer kg26 (SEQ ID NO. 22).

pKG123 (pak-3b wild-type; DSM 16152) was constructed by replacing an EcoRV-SacI restriction fragment (the C-terminal part of the kinase domain) in pKG44, containing deviations from the wild-type sequence, with the corresponding wild-type fragment from pKG58, thus creating a full-length, wild-type cDNA clone.

RNAi

RNA interference was done using the feeding method as described previously in Fraser et al. 2000 and Kamath et al. 2000. Double RNAi was done either by mixing bacterial cultures before seeding plates or by generation of vector constructs containing two cDNA fragments.

Vectors for RNAi by feeding were generated by cloning full-length or partial cDNAs into derivatives of the double T7 vector pPD129.36 (Timmons & Fire, Nature 395, 854). Either a Gateway-adopted version (pKG14) was used for cloning according to standard Gateway protocols (Invitrogen) or a version with a Srfl site added to the polylinker (pKG90) was used for direct cloning of PCR products as described (Schlotterer, C. and Wolff, C. Trends Genet, 1996. 12, 286-287).

RNAi vectors:

pKG61 (dT7-pak-1); vector; pKG14; insert: bp 1-1710 of pak-1; the RNA is encoded from 89 to 1753 of SEQ ID NO. 26 (entire ORF) (SEQ ID NO. 26)

pKG65 (dT7-pak-3); vector: pKG14; insert: bp 1141-1941 of pak-3b (kinase domain); the RNA is encoded from 84 to 883 of SEQ ID NO. 27; specific for both pak-3a and pak-3b (SEQ ID NO. 27)

pKG71 (dT7-pak-3/-1); vector pKG14; inserts: bp 1141-1941 of pak-3b (kinase domain) and bp 921-1710 of pak-1 (kinase domain); the RNA is encoded from 84 to 884 (pak1) and 885 to 1674 (pak3) of SEQ ID NO. 28; for double RNAi against pak-1/pak-3 (SEQ ID NO. 28)

pKG63 (dT7-pak-3a); vector pKG14; insert: bp 1-128 of pak-3a (N-terminus); the RNA is encoded from 89 to 216 of SEQ ID NO. 29; specific for pak-3a (SEQ ID NO. 29)

pKG64 (dT7-pak-3b); vector pKG14; insert: bp 1-788 of pak-3b (N-terminus); the RNA is encoded from 89 to 876 of SEQ ID NO. 30; specific for pak-3b (SEQ ID NO. 30)

pKG167 (dT7-ced-10); vector pKG90; insert: bp 40-562 of c09g12.8 b (ced-10); the RNA is encoded from 136 to 658 of SEQ ID NO. 31 pKG169 (d7-mig-2); vector pKG90; insert: bp 13-566 of c35c5.4 (mig-2); the RNA is encoded from 137 to 689 of SEQ ID NO. 32.

Assay for phenotypic analysis

Egg lay was scored by placing 5 or 10 [for 1. pak-1 (RNAi); 2. pak-1(ok448); pak-3(RNAi) 3. pak-1(ok448); pak-3b(RNAi)] adult F1 generation worms ($1^{st}$ generation progeny from the P0 parents initially exposed to RNAi treatment) on plates (5 plates per RNAi treatment) for 5 h at 20° C. and subsequence manual counting of the eggs after removal of the adult worms. Embryonic lethality was defined as the number of eggs remaining 24 h after removal of the adult worms relative the total number of eggs laid.

Gonad morphology and distal tip cell (DTC) migration was scored essentially as described previously (Nishiwaki 1999 Genetics 152, 985-997; Su et al 2000, Development 127, 585-594). Briefly, F1 generation late L4 larvae or young adults were observed under Nomarski (DIC) optics using an Axioplan 2 microscope (Sulston and Horwitz 1977, Dev Biol 56, 110-156) and the trajectories of the DTCs were deduced from the shapes of the gonad arms. As a negative control worms were exposed to bacteria expressing the empty T7 vector. The DTC migration phenotypes were group into five different classes (FIG. 1a): I) wild-types, showing the typical C-shaped gonad with normal $1^{st}$ and $2^{nd}$ turns; II) Rac-type, typically observed in ced-10 and mig-2 mutants, with normal $1^{st}$ and $2^{nd}$ turns but with an additional $3^{rd}$ turn leading to that the gonadal tip points away from the midbody region (Reddien and Horwitz 2000, Nature Cell Biol 2, 131-136); III) Pak-type, with a normal $1^{st}$ turn but a $2^{nd}$ turn in the wrong direction away from the midbody region (a similar phenotype has been described previously for the mutant mig-14 [Nishiwaki 1999]); IV) Straight, where the gonad progresses without any turns along the ventral side away from the midbody region; V) Other, mainly a complete lack of gonad outgrowth or ruptured gonads with free-floating germ cells in the body.

Compound testing

For screening of candidate pak-3 inhibitory compounds, synchronized RB689 (pak-1, ok448) L1 larvae were obtained by NaOH/Na-hypochlorite treatment of gravid adults and subsequent incubation of the resulting eggs in M9 buffer O/N at 20° C. with agitation essentially as described (C. elegans, a practical approach, Ed. I. Hope, 1999). About 30 L1 larvae in NGM medium were mixed with 2 OD600 E. coli OP-50, 100 µM test compound, 1% DMSO (from compound stock solution) in a final volume of 50 µl per well in flat-bottomed 96-well plates and incubated at 20° for 3 to 4 days. Preliminary in-well scoring of gonad phenotypes was done using an Axiovert 200 microscope. For final scoring, worms were pipetted out of the wells, mounted and analyzed under Nomarski (DIC) optics. As a negative control worms were incubated with 1% DMSO.

Cloning of pak-3 cDNAs and identification of the pak-3 gene

The initial indication of a hitherto unknown pak gene in C. elegans came from the identification of a predicted open reading frame, y38f1a.10 (SEQ ID NO. 33), encoding a kinase domain with high homology to a pak-type kinase domain. (The kinase domain is also classified as a pak-type kinase domain in the kinase database "kinase.com" located on the world wide web). However, the predicted ORF y38f1a.10 does not encode for a CRIB-domain, the regulatory domain conserved within the PAK gene family. We noticed by sequence comparison that the EST yk651h1 (SEQ ID NO. 34, 35), covering the y38f1a.10 ORF, also contains parts of the predicted ORF f18a11.4 (SEQ ID NO. 36), located upstream of y38f1a.10. This suggested to us that those two predicted ORFs might in fact be one single gene. To test this we performed RT-PCR using a 3' gene-specific primer corresponding to the 3' end of y38f1a.10 and a 5' primer corresponding to the SL1 leader sequence spliced in trans to many C. elegans mRNAs. As it has been reported that the C. elegans pak-1 mRNA is SL1 trans-spliced we suspected that this might be the case also for mRNAs from other C. elegans pak genes.

Sequence analysis of the RT-PCR products obtained revealed two different classes of mRNAs. The first class (isoforms a) corresponds roughly to the predicted ORF y38f1a.10 but with an additional exon upstream of the kinase domain. The second class (isoforms b) spans both ORFs y38f1a.10 and f18a11.4, thus demonstrating that these two ORFs belong to one single gene. However, the mRNAs have a 5' region longer than predicted in f18a11.4 and also longer than the EST yk651h1. Sequence analysis revealed a splicing pattern different from the ORF f18a11.4 and most importantly a domain with homology by a CRIB domain. Blast sequence database searches with cDNA isoforms b yielded a highest similarity score against human and rodent PAK3 and secondly against human and rodent PAK1.

Taken together this demonstrates that the two predicted ORFs y38f1a.10 (SEQ ID NO. 33) and f18a.11.4 (SEQ ID NO. 36) are in fact one gene that codes for two different mRNA splice variants, a short form encoding a protein mainly consisting of a pak-type kinase domain and a 5' longer form encoding a typical PAK protein. Based on sequence similarity and biological function (see below) we propose to call this novel pak gene pak-3 with the short splice variant denoted pak-3a and the long form pak-3b.

RNAi in C. elegans strains N2 (wild type) and RB689 (pak-1)

To assess the biological function of pak-3, RNAi by feeding experiments were performed. However, no obvious phenotypes could be detected when N2 wild-type worms were used for RNAi. Similarly, no phenotypes were observed when pak-1 function was assayed by RNAi, which was corroborated by observation of the pak-1 knock-out strain RB689, appearing completely wild-type in morphology and behavior.

Based on the similarity between pak-1 and pak-3 it was concluded that the lack of phenotypes in the RNAi experiments could be explained by supplementary functions of pak-1 and pak-3. To confirm this double RNAi experiments were conducted in the N2 background as well as pak-3 RNAi in the pak-1 knock-out strain RB689 (ok448). Similar results were obtained in both approaches, showing several drastic phenotypes: sterility, embryonic lethality and defects in the gonad migration pattern. Sterility was not completely penetrate but reproducibly shown to be very strong and readily visible. The result of a representative quantitative experiment is shown in Table I. Compared to the control worms exposed to mock RNAi treatment, the relative number of eggs laid by animals exposed to pak-1; pak-3 double RNAi was only 17%, when double RNAi was performed by mixing pak-1 and pak-3 RNAi bacterial cultures. When double RNAi was done using bacteria expressing a hybrid pak-1/pak-3 double RNA molecule the effect was somewhat stronger, 11%, suggesting that double RNAi by mixing of cultures is only moderately less efficient then the use of a dedicated double RNAi vector.

In pak-1lg (ok448); pak-3 (RNAi) animals sterility was even more penetrant, only 3% compared to pak-11f (ok 448); mock (RNAi). When compared with the results obtained in the N2 background, this indicates that pak-1 RNAi is not as penetrant as the complete knock-out, which can be expected.

Embryonic lethality was initially observed from the presence of small, round eggs that did not hatch upon prolonged incubation. Closer examination of these eggs suggested a high degree of cellular differentiation, for example muscle and pharynx tissue was clearly present. However, the overall morphology of the embryos was distorted, ranging from moderate to very severe with no morphological features conserved. A quantitative analysis (Table I) demonstrated more than 20% embryonic lethality in N2 animals and almost 40% in the RB689 background.

Interestingly, the phenotypes could not be observed in the first generation (P0) of worms exposed to RNAi, sterility and gonad defects were first observed in the F1 generation. Embryonic lethality was first seen in F2 generation embryos, suggesting material rescue in the F1 generation.

The cloning of pak-3 cDNAs had revealed the existence of two different splice variants, pak-3a and pak-3b. The functional importance of the two forms was demonstrated by conducting isoforms-specific RNAi in the RB689 background. Both as assayed from the sterility phenotype and as well as embryonic lethality it appears that the longer isoform pak-3b may play the mayor role with respect to the phenotypes observed (Table I).

A third pak gene is encoded by the predicted gene c45b11.1, which is most similar to the human PAK4. It is known that mammalian PAK4 differ significantly in regulation and function from PAK1 and PAK3. In agreement with this, no additional phenotypes were observed in double RNAi experiments between c45b11.1 and pak-1 or pak-3.

pak-3 and pak-1 are required for DTC pathfinding

In the C. elegans hermaphrodite the shape of the bi-lobed gonad is determined by the paths of cell migration of the gonadal distal tip cells (DTCs). In wild-type animals the two gonadal arms develop from the ventrally located gonadal primordium in the midbody. One DTC migrates anteriorly and the other posteriorly close to the ventral midline. The migration of the DTCs then undergoes two turns, the first turn towards the dorsal side and the second turn towards the midbody. The result of these migrations is the formation of the two symmetrical C-shaped adult gonad arms. As mentioned above we noted deviations from the wild-type gonad shape, indicative of defects in DTC migration, were noted in pak-3(RNAi); pak-1(RNAi) and pak-3(RNAi); RB689 (ok448) animals, but not in single pak-3(RNAi); pak-1 (RNAi) or the RB689 strain itself. Thus, also for this phenotype pak-1 and pak-3 appears to act supplementary. In more than half of the of gonads observed the first turn appeared normal whereas the second turn was in the wrong direction, i.e. instead of turning towards the midbody, the posterior gonad continued posteriorly and the anterior continued anteriorly (FIG. 1). Occasionally gonads without any turns were observed, the gonads continuing along the ventral midline towards the posterior and anterior end of the animal, respectively.

There were also analyzed the pak-3 isoform specific effects on DTC migration by pak-3b and pak-3a RNAi in the RB689 background. The results demonstrate that only the pak-3b isoform is important for DTC information, as for the sterility and embryonic lethality phenotypes (Table II).

Pak-Rac interaction

It has previously been described that two of the three Rac GTPases in *C. elegans*, ced-10 and mig-2, are involved in DTC pathfinding (Reedien & Horwitz, 2000, Lundquist et al 2001). In ced-10 and mig-2 mutants the gonads undergo a third, extra, turn after the second turn, leading to gonad tips pointing away from the midbody. This phenotype is different from what was observed in pak-1; pak-3 mutant animals, in which already the second turn was defective. It is furthermore known from invitro studies and mammalian cell systems (e.g. Bishop & Hall Biochem J, 2000) that Rho GTPases, to which the Rac proteins belong, are upstream regulators of PAKs. Given that the *C. elegans* paks also are important for DTC pathfinding it was deducted that there is an interaction between pak-1 and pak-3 and the two Racs ced-10 and mig-2 in *C. elegans* gonad development. To demonstrate this a set of RNAi experiments was performed in different genetic backgrounds (summarized in Table II). The different experimental combinations consistently showed that mig-2 or ced-10 loss of function did not lead to a stronger phenotype in combination with pak-3 than the separate single loss of function mutants. However, in combination with pak-1 mutants the penetrance and severity of the gonad migration defects increased dramatically. As pak-1 and pak-3 act supplementary, these results suggest that ced-10 and mig-2 act as upstream regulators of pak-3 but not, or only to a minor extent, of pak-1. Interestingly, the ced-10; mig-2; pak-1 triple mutant animals were much stronger affected than pak-1; pak-3 double mutants, suggesting that the two Racs also act through other pathways than pak-3 in parallel. Furthermore it was not only observed that the penetrance of DTC pathfinding defects was higher in ced-10; mig-2; pak-1 animals but also the phenotypic spectrum shifted towards more severe pathfinding and migration defects. High frequencies of gonads were observed without turns and also gonad movement defects. This demonstrates that both Paks and Racs are involved in several stages and aspects of DTC pathfinding but that these functions are not evident in the single or double mutants, probably as an effect of the redundant functions of these genes.

Compound mimicking RNAi phenotype

To investigate if the gonad migration defect phenotype can be used as a reporter for PAK-3 inhibitory small molecules, worms were exposed to a set of potential PAK inhibitors, derived from a chemical compound collection, in a 96-well assay format. Synchronized RB689 (pak-1, ok448) L1 larvae were incubated with test compounds in NGM (media) and *E. coli* OP-50 as food source. As the compounds were added as DMSO solutions, worms exposed to DMSO was used as a control. At late L4 or early young adult stage, gonad phenotypes were scored.

Several of the 14 substances tested showed a partial effect on gonad migration, causing phenotypes similar to those seen in pak-1; pak-3 (RNAi) animals. In particular, one compound tested, A000025706, was shown to reproducibly cause gonad migration defects (Table III). Out of 100 gonads analyzed, 74 were found to have gonad migration defects.

The observation that the types of defects observed differ somewhat from those observed with RNAi is possibly due to phamacological properties of the compound, e.g. uptake and stability. It is also possible that other kinases involved in gonad development and other developmental processes are also inhibited by A000025706. In fact, we observed general growth retardation in worms treated with this compound, suggesting a certain degree of non-specified effects of A000025706. However, as A000025706 has been confirmed as a PAK inhibitor in other assays (data not shown) we believe that most or all of the gonad migration defects observed can be attributed to a specific inhibition of PAK-3.

The observation that PAK inhibitors can be identified in a *C. elegans*-based assay demonstrates the usefulness of the model organism as a tool for phamacological research. The fact that growth retardation was observed also exemplified that potential side effects can be identified in parallel to the specific assay readout, i.e. that *C. elegans*-based assays can be valuable as high-throughput screening systems.

TABLE I

| Strain | RNAi treatment | Genotype | % Eggs laid | % Emb Lethality |
|---|---|---|---|---|
| N2 | ctrl | Wild-type | 100 | 0.2 |
|  | pak-1 | pak-1 (RNAi) | 113 | 2.2 |
|  | pak-3 | pak-3 (RNAi) | 69 | 5.0 |
|  | pak-1/-3 (one vector) | pak-1 (RNAi); pak-3(RNAi); | 11 | 20.8 |
|  | pak-1/pak-3 (mixed vectors) | pak-1(RNAi); pak-3(RNAi | 17 | 15.4 |
| RB689 | ctrl | pak-1(ok448) | 100 | 4.4 |
|  | pak-3 | pak-1(ok448); pak-3(RNAi) | 3 | 38.7 |
|  | pak-3a | pak-1(ok448); pak-3a(RNAi) | 134 | 4.0 |
|  | pak-3b | pak-1(ok448); pak-3b(RNAi | 2 | 22.7 |

TABLE II

| Strain | RNAi construct | Genotype | % wt | % rac | pathfinding defects % pak | % straight | movement defects % other | % affected gonads | n |
|---|---|---|---|---|---|---|---|---|---|
| N2 | ctrl | Wild type | 100.0 | 0.0 | 0.0 | 0.0 | 0.0 | 0.0 | 168 |
|  | pak-1 | pak-1(RNAi) | 100.0 | 0.0 | 0.0 | 0.0 | 0.0 | 0.0 | 154 |
|  | pak-3 | pak-3(RNAi) | 99.3 | 0.0 | 0.0 | 0.7 | 0.0 | 0.7 | 150 |
|  | pak-1/-3(one vector) | pak-1(RNAi); pak-3(RNAi) | 41.7 | 0.0 | 54.3 | 3.5 | 0.4 | 58.3 | 230 |
|  | pak-1/pak-3(mixed vectors) | pak-1(RNAi); pak-3(RNAi) | 44.6 | 0.0 | 52.2 | 3.3 | 0.0 | 55.4 | 92 |
|  | mig-2 | mig-2(RNAi) | 91.2 | 8.1 | 0.7 | 0.0 | 0.0 | 8.8 | 136 |
|  | mig-2/pak-1 | mig-2(RNAi); pak-1(RNAi) | 75.0 | 1.6 | 22.6 | 0.8 | 0.0 | 25.0 | 124 |
|  | mig-2/pak-3 | mig-2(RNAi); pak-3(RNAi) | 88.8 | 7.2 | 2.0 | 2.0 | 0.0 | 11.2 | 152 |

TABLE II-continued

| Strain | RNAi construct | Genotype | % wt | % rac | % pak | % straight | % other | % affected gonads | n |
|---|---|---|---|---|---|---|---|---|---|
| | mig-2/ced-10 | mig-2(RNAi); ced-10(RNAi) | 92.7 | 5.6 | 1.6 | 0.0 | 0.0 | 7.3 | 124 |
| | ced-10 | ced-10(RNAi) | 90.5 | 8.8 | 0.7 | 0.0 | 0.0 | 9.5 | 148 |
| | ced-10/pak-1 | ced-10(RNAi); pak-1(RNAi) | 49.2 | 1.6 | 36.7 | 12.5 | 0.0 | 50.8 | 128 |
| | ced-10/pak-3 | ced-10(RNAi); pak-3(RNAi) | 96.6 | 3.4 | 0.0 | 0.0 | 0.0 | 3.4 | 146 |
| RB689 pak 1(ok448) | ctrl | pak-1(ok448) | 99.5 | 0.0 | 0.5 | 0.0 | 0.0 | 0.5 | 198 |
| | pak-3 | pak-1(ok448); pak-3(RNAi) | 44.1 | 0.0 | 49.6 | 4.7 | 1.7 | 55.9 | 236 |
| | pak-3a | pak-1(ok448); pak-3a(RNAi) | 100.0 | 0.0 | 0.0 | 0.0 | 0.0 | 0.0 | 80 |
| | pak-3b | pak-1(ok448); pak-3b(RNAi) | 31.7 | 0.0 | 54.9 | 2.4 | 11.0 | 68.3 | 82 |
| | mig-2 | pak-1(ok448); mig-2(RNAi) | 55.6 | 0.0 | 33.8 | 10.6 | 0.0 | 44.4 | 160 |
| | mig-2/pak-3 | pak-1(ok448); pak-3(RNAi); mig-2(RNAi) | 57.8 | 0.0 | 24.7 | 16.9 | 0.6 | 42.2 | 154 |
| | mig-2/ced-10 | pak-1(ok448); mig-2(RNAi); ced-10(RNAi) | 29.8 | 0.0 | 13.7 | 55.6 | 0.8 | 70.2 | 124 |
| | ced-10 | pak-1(ok448); ced-10(RNAi) | 37.8 | 1.2 | 32.3 | 28.0 | 0.6 | 62.2 | 164 |
| | ced-10/pak-3 | pak-1(ok448); pak-3(RNAi); | 43.8 | 3.1 | 34.6 | 18.5 | 0.0 | 56.2 | 162 |
| | pak-1 | pak-1(RNAi); mig-2(mu28) | 40.5 | 3.2 | 43.7 | 9.5 | 3.2 | 59.5 | 126 |
| | pak-3 | pak-3(RNAi); mig-2(mu28) | 74.6 | 23.0 | 0.0 | 2.4 | 0.0 | 25.4 | 126 |
| | pak-1/-3 | pak-1(RNAi); pak-3(RNAi); mig-2(mu28) | 5.5 | 0.8 | 43.0 | 48.4 | 2.3 | 94.5 | 128 |
| | mig-2 | mig-2(mu28); mig-2(RNAi) | 65.9 | 34.1 | 0.0 | 0.0 | 0.0 | 34.1 | 88 |
| | ced-10 | mig-2(mu28); ced-10(RNAi) | 59.8 | 14.8 | 13.9 | 7.4 | 4.1 | 40.2 | 122 |
| | ced-10/pak-1 | pak-1(RNAi); mig-2(mu28); ced-10(RNAi) | 14.1 | 4.7 | 20.3 | 50.0 | 10.9 | 85.9 | 128 |
| | ced-10/pak-3 | pak-3(RNAi); mig-2(mu28); ced-10(RNAi) | 74.6 | 14.8 | 4.1 | 2.5 | 4.1 | 25.4 | 122 |
| MT5013 ced-10 (n1993) | ctrl | ced-10(n1993) | 77.3 | 21.4 | 0.0 | 0.6 | 0.6 | 22.7 | 154 |
| | pak-1 | pak-1(RNAi); ced-10(n1993) | 47.4 | 1.3 | 36.4 | 14.3 | 0.6 | 52.6 | 154 |
| | pak-3 | pak-3(RNAi); cad-10(n1993) | 82.5 | 14.3 | 1.3 | 1.3 | 0.6 | 17.5 | 154 |
| | pak-1/-3 | pak-1(RNAi); pak-3(RNAi); ced-10(n1993) | 49.7 | 0.7 | 43.0 | 2.6 | 4.0 | 50.3 | 151 |
| | mig-2 | mig-2(RNAi); ced-10(n1993) | 81.7 | 6.3 | 4.8 | 1.6 | 5.6 | 18.3 | 126 |
| | mig-2/pak-1 | pak-1(RNAi); mig-2(RNAi); ced-10(n1993) | 11.3 | 2.4 | 16.1 | 50.8 | 19.4 | 88.7 | 124 |
| | mig-2/pak-3 | pak-3(RNAi); mig-2(RNAi); ced-10(n1993) | 87.1 | 8.9 | 0.0 | 0.0 | 4.0 | 12.9 | 124 |
| | ced-10 | ced-10(n1993); ced-10(RNAi) | 75.0 | 9.2 | 5.3 | 0.0 | 10.5 | 25.0 | 76 |

TABLE III

| Strain | Cpd | % wt | % pak-like | % Straight | % Movement Def | % affected | n |
|---|---|---|---|---|---|---|---|
| RB689 pak-1(ok448) | ctrl | 99 | 0 | 0 | 1 | 1 | 80 |
| RB689 pak-1(ok448) | 25706 | 26 | 4 | 51 | 19 | 74 | 100 |

The invention claimed is:

1. An isolated polynucleotide comprising a DNA sequence selected from one of the following groups:
   a] a DNA sequence of SEQ ID NO. 1; or
   b] a DNA sequence which is complementary to SEQ ID NO. 1; or
   c] a DNA sequence which is degenerate as a result of the genetic code to the DNA sequence of SEQ ID NO. 1.

2. An isolated polynucleotide comprising a polynucleotide sequence of SEQ ID NO. 1.

3. A recombinant vector sequence comprising SEQ ID NO. 1.

4. An isolated host cell comprising the recombinant vector of claim 3.

5. The isolated host cell of claim 4 which is a cell of *E. coli* or of *Saccharomyces cerevisiae*.

6. A method of manufacturing an RNA molecule wherein the recombinant vector of claim 3 is transformed into a bacterial strain, the RNA is transcribed from the vector and the transcribed RNA is isolated and/or purified.

7. An RNA molecule obtained by the method of claim 6.

* * * * *

SEQUENCE LISTING

<160> NUMBER OF SEQ ID NOS: 36

<210> SEQ ID NO 1
<211> LENGTH: 1281
<212> TYPE: DNA
<213> ORGANISM: Caenorhabditis elegans

<400> SEQUENCE: 1

```
atgtttcaaa atagtccgat gatgtacgac tggtggaatg acaccaccaa accgaaacac     60
cagcagccga cacttaacgt gttgtcacca tggggagcat atttcaatca cattggaaat    120
gaactgctgc atctgaaaat cgcatcgtcg acagtatcct cgggatgctc gtctccacaa    180
cagtattcgt ctgctcgatc cgttggtaac tcgctctcca acggcagtgt tgtctccaca    240
```

-continued

```
acatcgtcag atggtgatgt gcaattgtcg aataaggaaa attcgaatga caaatcagtt      300
ggagacaaga atgggaacac caccacaaac aaaacgaccg tcgaaccacc tccaccagaa      360
gagccacctg ttcgtgttcg agcatctcat cgtgaaaagc tttctgattc cgaagtgctc      420
aatcaactcc gcgagattgt taatccaagt aatccacttg aaagtacga gatgaagaag       480
caaatcggtg ttggagcatc cggaactgta ttcgttgcta atgtggccgg cagcactgat      540
gtggtggctg tgaagagaat ggctttcaag actcagccga agaaggagat gttgctcacc      600
gagattaagg ttatgaagca gtatcgacac ccgaacctcg tcaactacat tgaatcgtat      660
ctggttgatg ctgatgatct tgggtagtg atggattatc tggaaggtgg aaacttgaca       720
gatgtcgttg tgaagactga gttggacgaa ggacaaattg cagcagtttt gcaagaatgt      780
cttaaagcgc ttcacttcct tcatagacac tccatagtgc accgagatat caagagtgac      840
aacgtgctgc tcggcatgaa cggagaggtt aagctcaccg atatgggatt ctgtgctcag      900
attcagccgg gatcgaaaag agatactgtc gtcggaactc catattggat gtcgccggag      960
atattgaaca gaagcagta caactataag gttgacattt ggtcgctggg aattatggct      1020
ctagagatga ttgatggaga gccaccatat ttgagagaaa ccctttgaa ggctatctac      1080
ttgattgctc aaaacgggaa gccagagatc aagcaacgcg acagactgtc ttcagagttc      1140
aacaatttcc ttgacaagtg tcttgttgtt gatccggatc agagagccga tacaacggag     1200
ctcttggcac atccattcct gaaaaaggcg aagccactct caagcctgat tccatacatc     1260
agagccgtcc gagaaaagta g                                               1281
```

<210> SEQ ID NO 2
<211> LENGTH: 1941
<212> TYPE: DNA
<213> ORGANISM: Caenorhabditis elegans

<400> SEQUENCE: 2

```
atgtcaactt caaaaagttc caaggtgcga atacggaatt tcatcgggcg aatcttctct       60
cccagcgata agacaagga tcgagacgat gagatgaagc catcctcgtc cgcaatggat       120
attagtcagc catataacac agtgcatcga gtccacgttg atacgacgg ccagaagttc       180
agcggactgc cgcaaccatg gatggatatt cttctccgag acattagtct tgccgatcag      240
aagaaggatc cgaacgcggt ggtgactgcg ttgaagttct acgcacaatc aatgaaggag      300
aacgagaaga cgaaattcat gacgacgaat agtgttttca cgaatagcga tgacgatgat      360
gtggacgttc agttgaccgg acaagtcacg gaacatttga ggaatttgca gtgtagtaat      420
ggttccgcaa cttccccatc tacatcagtg tcagcttcat cttcttctgc tcgtccactg      480
acaaatggaa ataatcatct ttccacggcg tcgtctaccg acacatctct ctcattatcg      540
gaaaggaata acgttccgtc tccagctcca gttccatata gtgaaagtgc tccacaactg      600
aaaacattca ccggagagac tccaaaactg catccacgat ctccgttccc gcctcaaccg      660
ccagttcttc cgcaacgaag caaaaccgca tcggcagtgg cgacgacgac gacgaatccg      720
acgacttcga atggagcacc accaccagtt cctggatcga aaggaccccc ggtgccaccg      780
aaaccatcgc atctgaaaat cgcatcgtcg acagtatcct cgggatgctc gtctccacaa      840
cagtattcgt ctgctcgatc cgttggtaac tcgctctcca acggcagtgt tgtctccaca      900
acatcgtcag atggtgatgt gcaattgtcg aataaggaaa attcgaatga caaatcagtt      960
ggagacaaga atgggaacac caccacaaac aaaacgaccg tcgaaccacc tccaccagaa     1020
```

```
gagccacctg ttcgtgttcg agcatctcat cgtgaaaagc tttctgattc cgaagtgctc    1080
aatcaactcc gcgagattgt taatccaagt aatccacttg gaaagtacga gatgaagaag    1140
caaatcggtg ttggagcatc cggaactgta ttcgttgcta atgtggccgg cagcactgat    1200
gtggtggctg tgaagagaat ggctttcaag actcagccga agaaggagat gttgctcacc    1260
gagattaagg ttatgaagca gtatcgacac ccgaacctcg tcaactacat tgaatcgtat    1320
ctggttgatg ctgatgatct tgggtagtg atggattatc tggaaggtgg aaacttgaca    1380
gatgtcgttg tgaagactga gttggacgaa ggacaaattg cagcagtttt gcaagaatgt    1440
cttaaagcgc ttcacttcct tcatagacac tccatagtgc accgagatat caagagtgac    1500
aacgtgctgc tcggcatgaa cggagaggtt aagctcaccg atatgggatt ctgtgctcag    1560
attcagccgg gatcgaaaag agatactgtc gtcggaactc catattggat gtcgccggag    1620
atattgaaca gaagcagta caactataag gttgacattt ggtcgctggg aattatggct    1680
ctagagatga ttgatggaga gccaccatat ttgagagaaa cacctttgaa ggctatctac    1740
ttgattgctc aaaacgggaa gccagagatc aagcaacgcg acagactgtc ttcagagttc    1800
aacaatttcc ttgacaagtg tcttgttgtt gatccggatc agagagccga tacaacggag    1860
ctcttggcac atccattcct gaaaaaggcg aagccactct caagcctgat tccatacatc    1920
agagccgtcc gagaaaagta g                                               1941

<210> SEQ ID NO 3
<211> LENGTH: 1941
<212> TYPE: DNA
<213> ORGANISM: Caenorhabditis elegans

<400> SEQUENCE: 3
atgtcaactt caaaaagttc caaggtgcga atacggaatt tcatcgggcg aatcttctct      60
cccagcgata agacaagga tcgagacgat gagatgaagc catcctcgtc cgcaatggat     120
attagtcagc catataacac agtgcatcga gtccacgttg gatacgacgg ccagaagttc     180
agcggactgc cgcaaccatg gatggatatt cttctccgag acattagtct tgccgatcag     240
aagaaggatc cgaacgcggt ggtgactgcg ttgaagttct acgcacaatc aatgaaggag     300
aacgagaaga cgaaattcat gacgacgaat agtgttttca cgaatagcga tgacgatgat     360
gtggacgttc agttgaccgg acaagtcacg gaacatttga ggaatttgca gtgtagtaat     420
ggttccgcaa cttcccccatc tacatcagtg tcagcttcat cttcttctgc tcgtccactg     480
acaaatggaa ataatcatct ttccacgcgc tcgtctaccg acacatctct ctcattatcg     540 gaaggaata acgttccgtc tccagctcca gttccatata gtgaaagtgc tccacaactg     600
aaaacattca ccggagagac tccaaaactg catccacgat ctccgttccc gcctcaaccg     660
ccagttcttc cgcaacgaag caaaaccgca tcggcagtgg cgacgacgac gacgaatccg     720
acgacttcga atggagcacc accaccagtt cctggatcga aaggacccc ggtgccaccg     780 aaaccatcgc atctgaaaat cgcatcgtcg acagtatcct cgggatgctc gtctccacaa     840
cagtattcgt ctgctcgatc cgttggtaac tcgctctcca acggcagtgt tgtctccaca     900
acatcgtcag atggtgatgt gcaattgtcg aataaggaaa attcgaatga caaatcagtt     960
ggagacaaga atgggaacac caccacaaac aaaacgaccg tcgaaccacc tccaccagaa    1020
gagccacctg ttcgtgttcg agcatctcat cgtgaaaagc tttctgattc cgaagtgctc    1080
aatcaactcc gcgagattgt taatccaagt aatccacttg gaaagtacga gatgaagaag    1140
caaatcggtg ttggagcatc cggaactgta ttcgttgcta atgtggccgg cagcactgat    1200
```

-continued

```
gtggtggctg tgaagagaat ggctttcaag actcagccga agaaggagat gttgctcacc    1260
gagattaagg ttatgaagca gtatcgacac ccgaacctcg tcaactacat tgaatcgtat    1320
ctggttgatg ctgatgatct ttgggtagtg atggattatc tggaaggtgg aaacttgaca    1380
gatgtcgttg tgaagactga gttggacgaa ggacaaattg cagcagtttt gcaagaatgt    1440
cttaaagcgc ttcacttcct tcatagacac tccatagtgc accgagatat caagagtgac    1500
aacgtgctgc tcggcatgaa cggagaggtt aagctcaccg atatgggatt ctgtgctcag    1560
attcagccgg gatcgaaaag agatactgtc gtcggaactc atattggat gtcgccggag    1620 atattgaaca agaagcagta caactataag gttgacattt ggtcgctggg aattatggcc    1680
ctagagatga ttgatggaga gccaccatat ttgagagaaa caccctttgaa ggctatctac    1740 ttgattgctc aaaacgggaa gccagagatc aagcaacgcg acagactgtc ttcagagttc    1800
aacaatttcc ttgacaagtg tcttgttgtt gatccggatc agagagccga tacaacggag    1860
ctcttggcac atccattcct gaaaaaggcg aagccactct caagcctgat tccatacatc    1920
agagccgtcc gagaaaagta g                                              1941
```

<210> SEQ ID NO 4
<211> LENGTH: 1947
<212> TYPE: DNA
<213> ORGANISM: Caenorhabditis elegans

<400> SEQUENCE: 4

```
atgtcaactt caaaaagttc caaggtgcga atacggaatt tcatcgggcg aatcttctct     60
cccagcgata agacaagga tcgagacgat gagatgaagc catcctcgtc cgcaatggat    120
attagtcagc catataacac agtgcatcga gtccacgttg atacgacgg ccagaagttc    180 agcggactgc cgcaaccatg gatggatatt cttctccgag acattagtct tgccgatcag    240
aagaaggatc cgaacgcggt ggtgactgcg ttgaagttct acgcacaatc aatgaaggag    300
aacgagaaga cgaaattcat gacgacgaat agtgtttttca cgaatagcga tgacgatgat    360
gtggacgttc agttgaccgg acaagtcacg gaacatttga ggaatttgca gtgtagtaat    420
ggttccgcaa cttccccatc tacatcagtg tcagcttcat cttcttctgc tcgtccactg    480
acaaatggaa ataatcatct ttccacggcg tcgtctaccg acacatctct ctcattatcg    540
gaaaggaata acgttccgtc tccagctcca gttccatata gtgaaagtgc tccacaactg    600
aaaacattca ccggagagac tccaaaactg catccacgat ctccgttccc gcctcaaccg    660
ccagttcttc cgcaacgaag caaaaccgca tcggcagtgg cgacgacgac gacgaatccg    720
acgacttcga atggagcacc accaccagtt cctggatcga aaggacccccc ggtgccaccg    780 aaaccatcgc atctgaaaat cgcatcgtcg acagtatcct cgggatgctc gtctccacaa    840
cagtattcgt ctgctcgatc cgttggtaac tcgctctcca acggcagtgt tgtctccaca    900
acatcgtcag atggtgatgt gcaattgtcg aataaggaaa attcgaatga caaatcagtt    960
ggagacaaga atgggaacac caccacaaac aaaacgaccg tcgaaccacc tccaccagaa    1020
gagccacctg ttcgtgttcg agcatctcat cgtgaaaagc tttctgattc cgaagtgctc    1080
aatcaactcc gcgagattgt taatccaagt aatccacttg gaaagtacga gatgaagaag    1140
caaatcggtg ttggagcatc cggaactgta ttcgttgcta atgtggccgg cagcactgat    1200
gtggtggctg tgaagagaat ggctttcaag actcagccga agaaggagat gttgctcacc    1260
gagattaagg ttatgaagca gtatcgacac ccgaacctcg tcaactacat tgaatcgtat    1320
```

-continued

```
ctggttgatg ctgatgatct ttgggtagtg atggattatc tggaaggtgg aaacttgaca    1380
gatgtcgttg tgaagactga gttggacgaa ggacaaattg cagcagtttt gcaagaatgt    1440
cttaaagcgc ttcacttcct tcatagacac tccatagtgc accgagatat caagagtgac    1500
aacgtgctgc tcggcatgaa cggagaggtt aagctcaccg atatgggatt ctgtgctcag    1560
attcagccgg gatcgaaaag ttgtagagat actgtcgtcg gaactccata ttggatgtcg    1620
ccggagatat tgaacaagaa gcagtacaac tataaggttg acatttggtc gctgggaatt    1680
atggccctag atgattgatg tggagagcca ccatatttga gagaaacacc tttgaaggct    1740
atctacttga ttgctcaaaa cgggaagcca gagatcaagc aacgcgacag actgtcttca    1800
gagttcaaca atttccttga caagtgtctt gttgttgatc cggatcagag agccgataca    1860
acggagctct tggcacatcc attcctgaaa aggcgaagc cactctcaag cctgattcca    1920
tacatcagag ccgtccgaga aaagtag                                        1947

<210> SEQ ID NO 5
<211> LENGTH: 1806
<212> TYPE: DNA
<213> ORGANISM: Caenorhabditis elegans

<400> SEQUENCE: 5
atgtcaactt caaaaagttc caaggtgcga atacggaatt tcatcgggcg aatcttctct     60
cccagcgata agacaagga tcgagacgat gagatgaagc catcctcgtc cgcaatggat    120
attagtcagc catataacac agtgcatcga gtccacgttg atacgacgg ccagaagttc    180
agcggactgc cgcaaccatg gatggatatt cttctccgag acattagcta tttcagtctt    240
gccgatcaga gaaggatcc gaacgcggtg gtgactgcgt tgaagttcta cgcacaatca    300
atgaaggaga acgagaagac gaaattcatg acgacgaata gtgttttcac gaatagcgat    360
gacgatgatg tggacgttca gttgaccgga caagtcacgg aacatttgag gaatttgcag    420
tgtagtaatg gttccgcaac ttccccatct acatcagtgt cagcttcatc ttcttctgct    480
cgtccactga caaatggaaa taatcatctt tccacggcgt cgtctaccga cacatctctc    540
tcattatcgg aaaggaataa cgttccgtct ccagctccag ttccatatag tgaaagtgct    600
ccacaactga aaacattcac cggagagact ccaaaactgc atccacgatc tccgttcccg    660
cctcaaccgc cagttcttcc gcaacgaagc aaaaccgcat cggcagtggc gacgacgacg    720
acgaatccga cgacttcgaa tggagcacca ccaccagttc ctggatcgaa aggacccccg    780
gtgccaccga accatcgaa ggaaaattcg aatgacaaat cagttggaga caagaatggg    840
aacaccacca caaacaaaac gaccgtcgaa ccacctccac cagaagagcc acctgttcgt    900
gttcgagcat ctcatcgtga aaagctttct gattccgaag tgctcaatca actccgcgag    960
attgttaatc caagtaatcc acttggaaag tacgagatga agaagcaaat cggtgttgga   1020
gcatccggaa ctgtattcgt tgctaatgtg ccggcagca ctgatgtggt ggctgtgaag   1080
agaatggctt tcaagactca gccgaagaag gagatgttgc tcaccgagat taaggttatg   1140
aagcagtatc gacacccgaa cctcgtcaac tacattgaat cgtatctggt tgatgctgat   1200
gatcttggg tagtgatgga ttatctggaa ggtggaaact tgacagatgt cgttgtgaag   1260
actgagttgg acgaaggaca aattgcagca gttttgcaag aatgtcttaa agcgcttcac   1320
ttccttcata gacactccat agtgcaccga gatatcaaga gtgacaacgt gctgctcggc   1380
atgaacggag aggttaagct caccgatatg ggattctgtg ctcagattca gccgggatcg   1440
aaaagagata ctgtcgtcgg aactccatat tggatgtcgc cggagatatt gaacaagaag   1500
```

-continued

```
cagtacaact ataaggttga catttggtcg ctgggaatta tggctctaga gatgattgat    1560
ggagagccac catatttgag agaaacacct ttgaaggcta tctacttgat tgctcaaaac    1620
gggaagccag agatcaagca acgcgacaga ctgtcttcag agttcaacaa tttccttgac    1680
aagtgtcttg ttgttgatcc ggatcagaga gccgatacaa cggagctctt ggcacatcca    1740
ttcctgaaaa aggcgaagcc actctcaagc ctgattccat acatcagagc cgtccgagaa    1800
aagtag                                                               1806
```

<210> SEQ ID NO 6
<211> LENGTH: 1947
<212> TYPE: DNA
<213> ORGANISM: Caenorhabditis elegans

<400> SEQUENCE: 6

```
atgtcaactt caaaaagttc caaggtgcga atacggaatt tcgtcgggcg aatcttctct      60
cccagcgata agacaagga tcgagacgat gagatgaagc catcctcgtc cgcaatggat     120
attagtcagc catataacac agtgcatcga gtccacgttg atacgacgg ccagaagttc     180 agcggactgc cgcaaccatg gatggatatt cttctccgag acattagtct tgccgatcag     240
aagaaggatc cgaacgcggt ggtgactgcg ttgaagttct acgcacaatc aatgaaggag     300
aacgagaaga cgaaattcat gacgacgaat agtgttttca cgaatagcga tgacgatgat     360
gtggacgttc agttgaccgg acaagtcacg gaacatttga ggaatttgca gtgtagtaat     420
ggttccgcaa cttccccatc tacatcagtg tcagcttcat cttcttctgc tcgtccactg     480
acaaatggaa ataatcatct ttccacggcg tcgtctaccg acacatctct ctcattatcg     540
gaaaggaata acgttccgtc tccagctcca gttccatata gtgaaagtgc tccacaactg     600
aaaacattca ccggagagac tccaaaactg catccacgat ctccgttccc gcctcaaccg     660
ccagttcttc cgcaacgaag caaaaccgca tcggcagtgg cgacgacgac gacgaatccg     720
acgacttcga atggagcacc accaccagtt cctggatcga aggaccccc ggtgccaccg     780 aaaccatcgc atctgaaaat cgcatcgtcg acagtatcct cgggatgctc gtctccacaa     840
cagtattcgt ctgctcgatc cgttggtaac tcgctctcca acggcagtgt tgtctccaca     900
acatcgtcag atggtgatgt gcaattgtcg aataaggaaa attcgaatga caaatcagtt     960
ggagacaaga tgggaacac caccacaaac aaaacgaccg tcgaaccacc tccaccagaa    1020
gagccacctg ttcgtgttcg agcatctcat cgtgaaaagc tttctgattc cgaagtgctc    1080
aatcaactcc gcgagattgt taatccaagt aatccacttg gaaagtacga gatgaagaag    1140
caaatcggtg ttggagcatc cggaactgta ttcgttgcta atgtggccgg cagcactgat    1200
gtggtggctg tgaagagaat ggctttcaag actcagccga agaaggagat gttgctcacc    1260
gagattaagg ttatgaagca gtatcgacac ccgaacctcg tcaactacat tgaatcgtat    1320
ctggttgatg ctgatgatct tgggtagtg atggattatc tggaaggtgg aaacttgaca    1380
gatgtcgttg tgaagactga gttggacgaa ggacaaattg cagcagtttt gcaagaatgt    1440
cttaaagcgc ttcacttcct tcatagacac tccatagtgc accgagatat caagagtgac    1500
aacgtgctgc tcggcatgaa cggagaggtt aagctcaccg atatgggatt ctgtgctcag    1560
attcagccgg gatcgaaaag ttgtagagat actgtcgtcg gaactccata ttggatgtcg    1620
ccggagatat tgaacaagaa gcagtacaac tataaggttg acatttggtc gctgggaatt    1680
atggctctag agatgattga tggagagcca ccatatttga gagaaacacc tttgaaggct    1740
```

```
atctacttga ttgctcaaaa cgggaagcca gagatcaagc aacgcgacag actgtcttca    1800
gagttcaaca atttccttga caagtgtctt gttgttgatc cggatcagag agccgataca    1860
acggagctct tggcacatcc attcctgaaa aaggcgaagc cactctcaag cctgattcca    1920
tacatcagag ccgtccgaga aaagtag                                         1947
```

<210> SEQ ID NO 7
<211> LENGTH: 426
<212> TYPE: PRT
<213> ORGANISM: Caenorhabditis elegans

<400> SEQUENCE: 7

```
Met Phe Gln Asn Ser Pro Met Met Tyr Asp Trp Trp Asn Asp Thr Thr
 1               5                  10                  15

Lys Pro Lys His Gln Gln Pro Thr Leu Asn Val Leu Ser Pro Trp Gly
            20                  25                  30

Ala Tyr Phe Asn His Ile Gly Asn Glu Leu Leu His Leu Lys Ile Ala
        35                  40                  45

Ser Ser Thr Val Ser Ser Gly Cys Ser Ser Pro Gln Gln Tyr Ser Ser
    50                  55                  60

Ala Arg Ser Val Gly Asn Ser Leu Ser Asn Gly Ser Val Val Ser Thr
65                  70                  75                  80

Thr Ser Ser Asp Gly Asp Val Gln Leu Ser Asn Lys Glu Asn Ser Asn
                85                  90                  95

Asp Lys Ser Val Gly Asp Lys Asn Gly Asn Thr Thr Thr Asn Lys Thr
            100                 105                 110

Thr Val Glu Pro Pro Pro Glu Glu Pro Pro Val Arg Val Arg Ala
        115                 120                 125

Ser His Arg Glu Lys Leu Ser Asp Ser Glu Val Leu Asn Gln Leu Arg
    130                 135                 140

Glu Ile Val Asn Pro Ser Asn Pro Leu Gly Lys Tyr Glu Met Lys Lys
145                 150                 155                 160

Gln Ile Gly Val Gly Ala Ser Gly Thr Val Phe Val Ala Asn Val Ala
                165                 170                 175

Gly Ser Thr Asp Val Val Ala Val Lys Arg Met Ala Phe Lys Thr Gln
            180                 185                 190

Pro Lys Lys Glu Met Leu Leu Thr Glu Ile Lys Val Met Lys Gln Tyr
        195                 200                 205

Arg His Pro Asn Leu Val Asn Tyr Ile Glu Ser Tyr Leu Val Asp Ala
    210                 215                 220

Asp Asp Leu Trp Val Val Met Asp Tyr Leu Glu Gly Gly Asn Leu Thr
225                 230                 235                 240

Asp Val Val Val Lys Thr Glu Leu Asp Glu Gly Gln Ile Ala Ala Val
                245                 250                 255

Leu Gln Glu Cys Leu Lys Ala Leu His Phe Leu His Arg His Ser Ile
            260                 265                 270

Val His Arg Asp Ile Lys Ser Asp Asn Val Leu Leu Gly Met Asn Gly
        275                 280                 285

Glu Val Lys Leu Thr Asp Met Gly Phe Cys Ala Gln Ile Gln Pro Gly
    290                 295                 300

Ser Lys Arg Asp Thr Val Val Gly Thr Pro Tyr Trp Met Ser Pro Glu
305                 310                 315                 320

Ile Leu Asn Lys Lys Gln Tyr Asn Tyr Lys Val Asp Ile Trp Ser Leu
                325                 330                 335
```

-continued

```
Gly Ile Met Ala Leu Glu Met Ile Asp Gly Glu Pro Pro Tyr Leu Arg
            340                 345                 350

Glu Thr Pro Leu Lys Ala Ile Tyr Leu Ile Ala Gln Asn Gly Lys Pro
            355                 360                 365

Glu Ile Lys Gln Arg Asp Arg Leu Ser Ser Glu Phe Asn Asn Phe Leu
            370                 375                 380

Asp Lys Cys Leu Val Val Asp Pro Asp Gln Arg Ala Asp Thr Thr Glu
385                 390                 395                 400

Leu Leu Ala His Pro Phe Leu Lys Lys Ala Lys Pro Leu Ser Ser Leu
                405                 410                 415

Ile Pro Tyr Ile Arg Ala Val Arg Glu Lys
            420                 425
```

<210> SEQ ID NO 8
<211> LENGTH: 646
<212> TYPE: PRT
<213> ORGANISM: Caenorhabditis elegans

<400> SEQUENCE: 8

```
Met Ser Thr Ser Lys Ser Ser Lys Val Arg Ile Arg Asn Phe Ile Gly
1               5                   10                  15

Arg Ile Phe Ser Pro Ser Asp Lys Asp Lys Asp Arg Asp Asp Glu Met
            20                  25                  30

Lys Pro Ser Ser Ser Ala Met Asp Ile Ser Gln Pro Tyr Asn Thr Val
            35                  40                  45

His Arg Val His Val Gly Tyr Asp Gly Gln Lys Phe Ser Gly Leu Pro
        50                  55                  60

Gln Pro Trp Met Asp Ile Leu Leu Arg Asp Ile Ser Leu Ala Asp Gln
65                  70                  75                  80

Lys Lys Asp Pro Asn Ala Val Val Thr Ala Leu Lys Phe Tyr Ala Gln
                85                  90                  95

Ser Met Lys Glu Asn Glu Lys Thr Lys Phe Met Thr Thr Asn Ser Val
            100                 105                 110

Phe Thr Asn Ser Asp Asp Asp Val Asp Val Gln Leu Thr Gly Gln
        115                 120                 125

Val Thr Glu His Leu Arg Asn Leu Gln Cys Ser Asn Gly Ser Ala Thr
    130                 135                 140

Ser Pro Ser Thr Ser Val Ser Ala Ser Ser Ser Ala Arg Pro Leu
145                 150                 155                 160

Thr Asn Gly Asn Asn His Leu Ser Thr Ala Ser Ser Thr Asp Thr Ser
                165                 170                 175

Leu Ser Leu Ser Glu Arg Asn Asn Val Pro Ser Pro Ala Pro Val Pro
            180                 185                 190

Tyr Ser Glu Ser Ala Pro Gln Leu Lys Thr Phe Thr Gly Glu Thr Pro
        195                 200                 205

Lys Leu His Pro Arg Ser Pro Phe Pro Pro Gln Pro Pro Val Leu Pro
    210                 215                 220

Gln Arg Ser Lys Thr Ala Ser Ala Val Ala Thr Thr Thr Asn Pro
225                 230                 235                 240

Thr Thr Ser Asn Gly Ala Pro Pro Val Pro Gly Ser Lys Gly Pro
                245                 250                 255

Pro Val Pro Pro Lys Pro Ser His Leu Lys Ile Ala Ser Ser Thr Val
            260                 265                 270

Ser Ser Gly Cys Ser Ser Pro Gln Gln Tyr Ser Ser Ala Arg Ser Val
        275                 280                 285
```

Gly Asn Ser Leu Ser Asn Gly Ser Val Val Ser Thr Thr Ser Ser Asp
        290                 295                 300

Gly Asp Val Gln Leu Ser Asn Lys Glu Asn Ser Asn Asp Lys Ser Val
305                 310                 315                 320

Gly Asp Lys Asn Gly Asn Thr Thr Thr Asn Lys Thr Val Glu Pro
            325                 330                 335

Pro Pro Pro Glu Glu Pro Pro Val Arg Val Arg Ala Ser His Arg Glu
            340                 345                 350

Lys Leu Ser Asp Ser Glu Val Leu Asn Gln Leu Arg Glu Ile Val Asn
            355                 360                 365

Pro Ser Asn Pro Leu Gly Lys Tyr Glu Met Lys Lys Gln Ile Gly Val
        370                 375                 380

Gly Ala Ser Gly Thr Val Phe Val Ala Asn Val Ala Gly Ser Thr Asp
385                 390                 395                 400

Val Val Ala Val Lys Arg Met Ala Phe Lys Thr Gln Pro Lys Lys Glu
                405                 410                 415

Met Leu Leu Thr Glu Ile Lys Val Met Lys Gln Tyr Arg His Pro Asn
            420                 425                 430

Leu Val Asn Tyr Ile Glu Ser Tyr Leu Val Asp Ala Asp Leu Trp
        435                 440                 445

Val Val Met Asp Tyr Leu Glu Gly Gly Asn Leu Thr Asp Val Val Val
    450                 455                 460

Lys Thr Glu Leu Asp Glu Gly Gln Ile Ala Ala Val Leu Gln Glu Cys
465                 470                 475                 480

Leu Lys Ala Leu His Phe Leu His Arg His Ser Ile Val His Arg Asp
                485                 490                 495

Ile Lys Ser Asp Asn Val Leu Leu Gly Met Asn Gly Glu Val Lys Leu
            500                 505                 510

Thr Asp Met Gly Phe Cys Ala Gln Ile Gln Pro Gly Ser Lys Arg Asp
        515                 520                 525

Thr Val Val Gly Thr Pro Tyr Trp Met Ser Pro Glu Ile Leu Asn Lys
    530                 535                 540

Lys Gln Tyr Asn Tyr Lys Val Asp Ile Trp Ser Leu Gly Ile Met Ala
545                 550                 555                 560

Leu Glu Met Ile Asp Gly Glu Pro Pro Tyr Leu Arg Glu Thr Pro Leu
                565                 570                 575

Lys Ala Ile Tyr Leu Ile Ala Gln Asn Gly Lys Pro Glu Ile Lys Gln
            580                 585                 590

Arg Asp Arg Leu Ser Ser Glu Phe Asn Asn Phe Leu Asp Lys Cys Leu
        595                 600                 605

Val Val Asp Pro Asp Gln Arg Ala Asp Thr Thr Glu Leu Leu Ala His
    610                 615                 620

Pro Phe Leu Lys Lys Ala Lys Pro Leu Ser Ser Leu Ile Pro Tyr Ile
625                 630                 635                 640

Arg Ala Val Arg Glu Lys
                645

<210> SEQ ID NO 9
<211> LENGTH: 646
<212> TYPE: PRT
<213> ORGANISM: Caenorhabditis elegans
<220> FEATURE:
<223> OTHER INFORMATION: Description of Artificial Sequence:Vector

<400> SEQUENCE: 9

-continued

```
Met Ser Thr Ser Lys Ser Ser Lys Val Arg Ile Arg Asn Phe Ile Gly
 1               5                  10                  15

Arg Ile Phe Ser Pro Ser Asp Lys Asp Lys Asp Arg Asp Asp Glu Met
            20                  25                  30

Lys Pro Ser Ser Ser Ala Met Asp Ile Ser Gln Pro Tyr Asn Thr Val
            35                  40                  45

His Arg Val His Val Gly Tyr Asp Gly Gln Lys Phe Ser Gly Leu Pro
        50                  55                  60

Gln Pro Trp Met Asp Ile Leu Leu Arg Asp Ile Ser Leu Ala Asp Gln
65                  70                  75                  80

Lys Lys Asp Pro Asn Ala Val Val Thr Ala Leu Lys Phe Tyr Ala Gln
                85                  90                  95

Ser Met Lys Glu Asn Glu Lys Thr Lys Phe Met Thr Thr Asn Ser Val
            100                 105                 110

Phe Thr Asn Ser Asp Asp Asp Val Asp Val Gln Leu Thr Gly Gln
            115                 120                 125

Val Thr Glu His Leu Arg Asn Leu Gln Cys Ser Asn Gly Ser Ala Thr
130                 135                 140

Ser Pro Ser Thr Ser Val Ser Ala Ser Ser Ser Ala Arg Pro Leu
145                 150                 155                 160

Thr Asn Gly Asn Asn His Leu Ser Thr Ala Ser Ser Thr Asp Thr Ser
                165                 170                 175

Leu Ser Leu Ser Glu Arg Asn Asn Val Pro Ser Pro Ala Pro Val Pro
            180                 185                 190

Tyr Ser Glu Ser Ala Pro Gln Leu Lys Thr Phe Thr Gly Glu Thr Pro
        195                 200                 205

Lys Leu His Pro Arg Ser Pro Phe Pro Pro Gln Pro Pro Val Leu Pro
        210                 215                 220

Gln Arg Ser Lys Thr Ala Ser Ala Val Ala Thr Thr Thr Thr Asn Pro
225                 230                 235                 240

Thr Thr Ser Asn Gly Ala Pro Pro Val Pro Gly Ser Lys Gly Pro
                245                 250                 255

Pro Val Pro Pro Lys Pro Ser His Leu Lys Ile Ala Ser Ser Thr Val
            260                 265                 270

Ser Ser Gly Cys Ser Ser Pro Gln Gln Tyr Ser Ser Ala Arg Ser Val
            275                 280                 285

Gly Asn Ser Leu Ser Asn Gly Ser Val Val Ser Thr Thr Ser Ser Asp
            290                 295                 300

Gly Asp Val Gln Leu Ser Asn Lys Glu Asn Ser Asn Asp Lys Ser Val
305                 310                 315                 320

Gly Asp Lys Asn Gly Asn Thr Thr Thr Asn Lys Thr Thr Val Glu Pro
                325                 330                 335

Pro Pro Pro Glu Glu Pro Pro Val Arg Val Arg Ala Ser His Arg Glu
            340                 345                 350

Lys Leu Ser Asp Ser Glu Val Leu Asn Gln Leu Arg Glu Ile Val Asn
            355                 360                 365

Pro Ser Asn Pro Leu Gly Lys Tyr Glu Met Lys Lys Gln Ile Gly Val
            370                 375                 380

Gly Ala Ser Gly Thr Val Phe Val Ala Asn Val Ala Gly Ser Thr Asp
385                 390                 395                 400

Val Val Ala Val Lys Arg Met Ala Phe Lys Thr Gln Pro Lys Lys Glu
                405                 410                 415
```

-continued

```
Met Leu Leu Thr Glu Ile Lys Val Met Lys Gln Tyr Arg His Pro Asn
            420                 425                 430

Leu Val Asn Tyr Ile Glu Ser Tyr Leu Val Asp Ala Asp Asp Leu Trp
        435                 440                 445

Val Val Met Asp Tyr Leu Glu Gly Gly Asn Leu Thr Asp Val Val
450                 455                 460

Lys Thr Glu Leu Asp Glu Gly Gln Ile Ala Ala Val Leu Gln Glu Cys
465                 470                 475                 480

Leu Lys Ala Leu His Phe Leu His Arg His Ser Ile Val His Arg Asp
                485                 490                 495

Ile Lys Ser Asp Asn Val Leu Leu Gly Met Asn Gly Glu Val Lys Leu
            500                 505                 510

Thr Asp Met Gly Phe Cys Ala Gln Ile Gln Pro Gly Ser Lys Arg Asp
            515                 520                 525

Thr Val Val Gly Thr Pro Tyr Trp Met Ser Pro Glu Ile Leu Asn Lys
        530                 535                 540

Lys Gln Tyr Asn Tyr Lys Val Asp Ile Trp Ser Leu Gly Ile Met Ala
545                 550                 555                 560

Leu Glu Met Ile Asp Gly Glu Pro Pro Tyr Leu Arg Glu Thr Pro Leu
                565                 570                 575

Lys Ala Ile Tyr Leu Ile Ala Gln Asn Gly Lys Pro Glu Ile Lys Gln
            580                 585                 590

Arg Asp Arg Leu Ser Ser Glu Phe Asn Asn Phe Leu Asp Lys Cys Leu
            595                 600                 605

Val Val Asp Pro Asp Gln Arg Ala Asp Thr Thr Glu Leu Leu Ala His
        610                 615                 620

Pro Phe Leu Lys Lys Ala Lys Pro Leu Ser Ser Leu Ile Pro Tyr Ile
625                 630                 635                 640

Arg Ala Val Arg Glu Lys
                645

<210> SEQ ID NO 10
<211> LENGTH: 648
<212> TYPE: PRT
<213> ORGANISM: Caenorhabditis elegans

<400> SEQUENCE: 10

Met Ser Thr Ser Lys Ser Ser Lys Val Arg Ile Arg Asn Phe Ile Gly
1               5                   10                  15

Arg Ile Phe Ser Pro Ser Asp Lys Asp Lys Asp Arg Asp Asp Glu Met
            20                  25                  30

Lys Pro Ser Ser Ala Met Asp Ile Ser Gln Pro Tyr Asn Thr Val
        35                  40                  45

His Arg Val His Val Gly Tyr Asp Gly Gln Lys Phe Ser Gly Leu Pro
    50                  55                  60

Gln Pro Trp Met Asp Ile Leu Leu Arg Asp Ile Ser Leu Ala Asp Gln
65                  70                  75                  80

Lys Lys Asp Pro Asn Ala Val Val Thr Ala Leu Lys Phe Tyr Ala Gln
                85                  90                  95

Ser Met Lys Glu Asn Glu Lys Thr Lys Phe Met Thr Thr Asn Ser Val
            100                 105                 110

Phe Thr Asn Ser Asp Asp Asp Val Asp Val Gln Leu Thr Gly Gln
        115                 120                 125

Val Thr Glu His Leu Arg Asn Leu Gln Cys Ser Asn Gly Ser Ala Thr
    130                 135                 140
```

-continued

```
Ser Pro Ser Thr Ser Val Ser Ala Ser Ser Ser Ala Arg Pro Leu
145                 150                 155                 160

Thr Asn Gly Asn Asn His Leu Ser Thr Ala Ser Ser Thr Asp Thr Ser
                165                 170                 175

Leu Ser Leu Ser Glu Arg Asn Asn Val Pro Ser Pro Ala Pro Val Pro
            180                 185                 190

Tyr Ser Glu Ser Ala Pro Gln Leu Lys Thr Phe Thr Gly Glu Thr Pro
        195                 200                 205

Lys Leu His Pro Arg Ser Pro Phe Pro Pro Gln Pro Pro Val Leu Pro
    210                 215                 220

Gln Arg Ser Lys Thr Ala Ser Ala Val Ala Thr Thr Thr Asn Pro
225                 230                 235                 240

Thr Thr Ser Asn Gly Ala Pro Pro Val Pro Gly Ser Lys Gly Pro
                245                 250                 255

Pro Val Pro Pro Lys Pro Ser His Leu Lys Ile Ala Ser Ser Thr Val
            260                 265                 270

Ser Ser Gly Cys Ser Ser Pro Gln Gln Tyr Ser Ser Ala Arg Ser Val
        275                 280                 285

Gly Asn Ser Leu Ser Asn Gly Ser Val Val Ser Thr Thr Ser Ser Asp
290                 295                 300

Gly Asp Val Gln Leu Ser Asn Lys Glu Ser Asn Asp Lys Ser Val
305                 310                 315                 320

Gly Asp Lys Asn Gly Asn Thr Thr Thr Asn Lys Thr Thr Val Glu Pro
                325                 330                 335

Pro Pro Pro Glu Glu Pro Pro Val Arg Val Arg Ala Ser His Arg Glu
            340                 345                 350

Lys Leu Ser Asp Ser Glu Val Leu Asn Gln Leu Arg Glu Ile Val Asn
        355                 360                 365

Pro Ser Asn Pro Leu Gly Lys Tyr Glu Met Lys Lys Gln Ile Gly Val
    370                 375                 380

Gly Ala Ser Gly Thr Val Phe Val Ala Asn Val Ala Gly Ser Thr Asp
385                 390                 395                 400

Val Val Ala Val Lys Arg Met Ala Phe Lys Thr Gln Pro Lys Lys Glu
                405                 410                 415

Met Leu Leu Thr Glu Ile Lys Val Met Lys Gln Tyr Arg His Pro Asn
            420                 425                 430

Leu Val Asn Tyr Ile Glu Ser Tyr Leu Val Asp Ala Asp Leu Trp
        435                 440                 445

Val Val Met Asp Tyr Leu Glu Gly Gly Asn Leu Thr Asp Val Val Val
    450                 455                 460

Lys Thr Glu Leu Asp Glu Gly Gln Ile Ala Ala Val Leu Gln Glu Cys
465                 470                 475                 480

Leu Lys Ala Leu His Phe Leu His Arg His Ser Ile Val His Arg Asp
                485                 490                 495

Ile Lys Ser Asp Asn Val Leu Leu Gly Met Asn Gly Glu Val Lys Leu
            500                 505                 510

Thr Asp Met Gly Phe Cys Ala Gln Ile Gln Pro Gly Ser Lys Ser Cys
        515                 520                 525

Arg Asp Thr Val Val Gly Thr Pro Tyr Trp Met Ser Pro Glu Ile Leu
    530                 535                 540

Asn Lys Lys Gln Tyr Asn Tyr Lys Val Asp Ile Trp Ser Leu Gly Ile
545                 550                 555                 560
```

```
Met Ala Leu Glu Met Ile Asp Gly Glu Pro Pro Tyr Leu Arg Glu Thr
                565                 570                 575

Pro Leu Lys Ala Ile Tyr Leu Ile Ala Gln Asn Gly Lys Pro Glu Ile
            580                 585                 590

Lys Gln Arg Asp Arg Leu Ser Ser Glu Phe Asn Asn Phe Leu Asp Lys
        595                 600                 605

Cys Leu Val Val Asp Pro Asp Gln Arg Ala Asp Thr Thr Glu Leu Leu
    610                 615                 620

Ala His Pro Phe Leu Lys Lys Ala Lys Pro Leu Ser Ser Leu Ile Pro
625                 630                 635                 640

Tyr Ile Arg Ala Val Arg Glu Lys
                645

<210> SEQ ID NO 11
<211> LENGTH: 601
<212> TYPE: PRT
<213> ORGANISM: Caenorhabditis elegans

<400> SEQUENCE: 11

Met Ser Thr Ser Lys Ser Ser Lys Val Arg Ile Arg Asn Phe Ile Gly
  1               5                  10                  15

Arg Ile Phe Ser Pro Ser Asp Lys Asp Lys Asp Arg Asp Asp Glu Met
             20                  25                  30

Lys Pro Ser Ser Ser Ala Met Asp Ile Ser Gln Pro Tyr Asn Thr Val
         35                  40                  45

His Arg Val His Val Gly Tyr Asp Gly Gln Lys Phe Ser Gly Leu Pro
     50                  55                  60

Gln Pro Trp Met Asp Ile Leu Leu Arg Asp Ile Ser Tyr Phe Ser Leu
 65                  70                  75                  80

Ala Asp Gln Lys Lys Asp Pro Asn Ala Val Val Thr Ala Leu Lys Phe
                 85                  90                  95

Tyr Ala Gln Ser Met Lys Glu Asn Glu Lys Thr Lys Phe Met Thr Thr
            100                 105                 110

Asn Ser Val Phe Thr Asn Ser Asp Asp Asp Val Asp Val Gln Leu
        115                 120                 125

Thr Gly Gln Val Thr Glu His Leu Arg Asn Leu Gln Cys Ser Asn Gly
    130                 135                 140

Ser Ala Thr Ser Pro Ser Thr Ser Val Ser Ala Ser Ser Ser Ser Ala
145                 150                 155                 160

Arg Pro Leu Thr Asn Gly Asn Asn His Leu Ser Thr Ala Ser Ser Thr
                165                 170                 175

Asp Thr Ser Leu Ser Leu Ser Glu Arg Asn Asn Val Pro Ser Pro Ala
            180                 185                 190

Pro Val Pro Tyr Ser Glu Ser Ala Pro Gln Leu Lys Thr Phe Thr Gly
        195                 200                 205

Glu Thr Pro Lys Leu His Pro Arg Ser Pro Phe Pro Pro Gln Pro Pro
    210                 215                 220

Val Leu Pro Gln Arg Ser Lys Thr Ala Ser Ala Val Ala Thr Thr Thr
225                 230                 235                 240

Thr Asn Pro Thr Thr Ser Asn Gly Ala Pro Pro Val Pro Gly Ser
                245                 250                 255

Lys Gly Pro Pro Val Pro Pro Lys Pro Ser Lys Glu Asn Ser Asn Asp
            260                 265                 270

Lys Ser Val Gly Asp Lys Asn Gly Asn Thr Thr Thr Asn Lys Thr Thr
        275                 280                 285
```

```
Val Glu Pro Pro Pro Glu Pro Pro Val Arg Val Arg Ala Ser
    290             295             300

His Arg Glu Lys Leu Ser Asp Ser Glu Val Leu Asn Gln Leu Arg Glu
305                 310                 315                 320

Ile Val Asn Pro Ser Asn Pro Leu Gly Lys Tyr Glu Met Lys Lys Gln
                325                 330                 335

Ile Gly Val Gly Ala Ser Gly Thr Val Phe Val Ala Asn Val Ala Gly
            340                 345                 350

Ser Thr Asp Val Val Ala Val Lys Arg Met Ala Phe Lys Thr Gln Pro
        355                 360                 365

Lys Lys Glu Met Leu Leu Thr Glu Ile Lys Val Met Lys Gln Tyr Arg
    370                 375                 380

His Pro Asn Leu Val Asn Tyr Ile Glu Ser Tyr Leu Val Asp Ala Asp
385                 390                 395                 400

Asp Leu Trp Val Val Met Asp Tyr Leu Glu Gly Gly Asn Leu Thr Asp
                405                 410                 415

Val Val Val Lys Thr Glu Leu Asp Glu Gly Gln Ile Ala Ala Val Leu
            420                 425                 430

Gln Glu Cys Leu Lys Ala Leu His Phe Leu His Arg His Ser Ile Val
        435                 440                 445

His Arg Asp Ile Lys Ser Asp Asn Val Leu Leu Gly Met Asn Gly Glu
    450                 455                 460

Val Lys Leu Thr Asp Met Gly Phe Cys Ala Gln Ile Gln Pro Gly Ser
465                 470                 475                 480

Lys Arg Asp Thr Val Val Gly Thr Pro Tyr Trp Met Ser Pro Glu Ile
                485                 490                 495

Leu Asn Lys Lys Gln Tyr Asn Tyr Lys Val Asp Ile Trp Ser Leu Gly
            500                 505                 510

Ile Met Ala Leu Glu Met Ile Asp Gly Glu Pro Pro Tyr Leu Arg Glu
        515                 520                 525

Thr Pro Leu Lys Ala Ile Tyr Leu Ile Ala Gln Asn Gly Lys Pro Glu
    530                 535                 540

Ile Lys Gln Arg Asp Arg Leu Ser Ser Glu Phe Asn Asn Phe Leu Asp
545                 550                 555                 560

Lys Cys Leu Val Val Asp Pro Asp Gln Arg Ala Asp Thr Thr Glu Leu
                565                 570                 575

Leu Ala His Pro Phe Leu Lys Lys Ala Lys Pro Leu Ser Ser Leu Ile
            580                 585                 590

Pro Tyr Ile Arg Ala Val Arg Glu Lys
        595                 600

<210> SEQ ID NO 12
<211> LENGTH: 648
<212> TYPE: PRT
<213> ORGANISM: Caenorhabditis elegans

<400> SEQUENCE: 12

Met Ser Thr Ser Lys Ser Ser Lys Val Arg Ile Arg Asn Phe Val Gly
1               5                   10                  15

Arg Ile Phe Ser Pro Ser Asp Lys Asp Lys Arg Asp Asp Glu Met
            20                  25                  30

Lys Pro Ser Ser Ser Ala Met Asp Ile Ser Gln Pro Tyr Asn Thr Val
        35                  40                  45

His Arg Val His Val Gly Tyr Asp Gly Gln Lys Phe Ser Gly Leu Pro
```

```
                50                  55                  60
Gln Pro Trp Met Asp Ile Leu Leu Arg Asp Ile Ser Leu Ala Asp Gln
 65                  70                  75                  80

Lys Lys Asp Pro Asn Ala Val Val Thr Ala Leu Lys Phe Tyr Ala Gln
                 85                  90                  95

Ser Met Lys Glu Asn Glu Lys Thr Lys Phe Met Thr Thr Asn Ser Val
            100                 105                 110

Phe Thr Asn Ser Asp Asp Asp Val Asp Val Gln Leu Thr Gly Gln
            115                 120                 125

Val Thr Glu His Leu Arg Asn Leu Gln Cys Ser Asn Gly Ser Ala Thr
130                 135                 140

Ser Pro Ser Thr Ser Val Ser Ala Ser Ser Ser Ala Arg Pro Leu
145                 150                 155                 160

Thr Asn Gly Asn Asn His Leu Ser Thr Ala Ser Ser Thr Asp Thr Ser
                165                 170                 175

Leu Ser Leu Ser Glu Arg Asn Asn Val Pro Ser Pro Ala Pro Val Pro
            180                 185                 190

Tyr Ser Glu Ser Ala Pro Gln Leu Lys Thr Phe Thr Gly Glu Thr Pro
            195                 200                 205

Lys Leu His Pro Arg Ser Pro Phe Pro Pro Gln Pro Pro Val Leu Pro
210                 215                 220

Gln Arg Ser Lys Thr Ala Ser Ala Val Ala Thr Thr Thr Asn Pro
225                 230                 235                 240

Thr Thr Ser Asn Gly Ala Pro Pro Val Pro Gly Ser Lys Gly Pro
                245                 250                 255

Pro Val Pro Pro Lys Pro Ser His Leu Lys Ile Ala Ser Ser Thr Val
            260                 265                 270

Ser Ser Gly Cys Ser Ser Pro Gln Gln Tyr Ser Ser Ala Arg Ser Val
            275                 280                 285

Gly Asn Ser Leu Ser Asn Gly Ser Val Val Ser Thr Thr Ser Ser Asp
            290                 295                 300

Gly Asp Val Gln Leu Ser Asn Lys Glu Asn Ser Asn Asp Lys Ser Val
305                 310                 315                 320

Gly Asp Lys Asn Gly Asn Thr Thr Asn Lys Thr Thr Val Glu Pro
                325                 330                 335

Pro Pro Pro Glu Glu Pro Pro Val Arg Val Arg Ala Ser His Arg Glu
            340                 345                 350

Lys Leu Ser Asp Ser Glu Val Leu Asn Gln Leu Arg Glu Ile Val Asn
            355                 360                 365

Pro Ser Asn Pro Leu Gly Lys Tyr Glu Met Lys Lys Gln Ile Gly Val
370                 375                 380

Gly Ala Ser Gly Thr Val Phe Val Ala Asn Val Ala Gly Ser Thr Asp
385                 390                 395                 400

Val Val Ala Val Lys Arg Met Ala Phe Lys Thr Gln Pro Lys Lys Glu
                405                 410                 415

Met Leu Leu Thr Glu Ile Lys Val Met Lys Gln Tyr Arg His Pro Asn
            420                 425                 430

Leu Val Asn Tyr Ile Glu Ser Tyr Leu Val Asp Ala Asp Leu Trp
            435                 440                 445

Val Val Met Asp Tyr Leu Glu Gly Gly Asn Leu Thr Asp Val Val Val
            450                 455                 460

Lys Thr Glu Leu Asp Glu Gly Gln Ile Ala Ala Val Leu Gln Glu Cys
465                 470                 475                 480
```

Leu Lys Ala Leu His Phe Leu His Arg His Ser Ile Val His Arg Asp
              485                 490                 495

Ile Lys Ser Asp Asn Val Leu Leu Gly Met Asn Gly Glu Val Lys Leu
        500                 505                 510

Thr Asp Met Gly Phe Cys Ala Gln Ile Gln Pro Gly Ser Lys Ser Cys
    515                 520                 525

Arg Asp Thr Val Val Gly Thr Pro Tyr Trp Met Ser Pro Glu Ile Leu
530                 535                 540

Asn Lys Lys Gln Tyr Asn Tyr Lys Val Asp Ile Trp Ser Leu Gly Ile
545                 550                 555                 560

Met Ala Leu Glu Met Ile Asp Gly Glu Pro Pro Tyr Leu Arg Glu Thr
                565                 570                 575

Pro Leu Lys Ala Ile Tyr Leu Ile Ala Gln Asn Gly Lys Pro Glu Ile
            580                 585                 590

Lys Gln Arg Asp Arg Leu Ser Ser Glu Phe Asn Asn Phe Leu Asp Lys
        595                 600                 605

Cys Leu Val Val Asp Pro Asp Gln Arg Ala Asp Thr Thr Glu Leu Leu
    610                 615                 620

Ala His Pro Phe Leu Lys Lys Ala Lys Pro Leu Ser Ser Leu Ile Pro
625                 630                 635                 640

Tyr Ile Arg Ala Val Arg Glu Lys
                645

<210> SEQ ID NO 13
<211> LENGTH: 3541
<212> TYPE: DNA
<213> ORGANISM: Artificial Sequence
<220> FEATURE:
<223> OTHER INFORMATION: Description of Artificial Sequence:Vector

<400> SEQUENCE: 13
gttaacgcta gcatggatct cgggccccaa ataatgattt tattttgact gatagtgacc    60
tgttcgttgc aacaaattga tgagcaatgc ttttttataa tgccaacttt gtacaaaaaa   120
gcaggctcaa aaatgtttca aaatagtccg atgatgtacg actggtggaa tgacaccacc   180
aaaccgaaac accagcagcc gacacttaac gtgttgtcac catggggagc atatttcaat   240
cacattggaa atgaactgct gcatctgaaa atcgcatcgt cgacagtatc ctcgggatgc   300
tcgtctccac aacagtattc gtctgctcga tccgttggta actcgctctc aacggcagt   360 gttgtctcca caacatcgtc agatggtgat gtgcaattgt cgaataagga aaattcgaat   420
gacaaatcag ttggagacaa gaatgggaac accaccacaa acaaaacgac cgtcgaacca   480
cctccaccag aagagccacc tgttcgtgtt cgagcatctc atcgtgaaaa gctttctgat   540
tccgaagtgc tcaatcaact ccgcgagatt gttaatccaa gtaatccact tggaaagtac   600
gagatgaaga agcaaatcgg tgttggagca tccggaactg tattcgttgc taatgtggcc   660
ggcagcactg atgtggtggc tgtgaagaga atggctttca agactcagcc gaagaaggag   720
atgttgctca ccgagattaa ggttatgaag cagtatcgac acccgaacct cgtcaactac   780
attgaatcgt atctggttga tgctgatgat ctttgggtag tgatggatta tctggaaggt   840
ggaaacttga cagatgtcgt tgtgaagact gagttggacg aaggacaaat tgcagcagtt   900
ttgcaagaat gtcttaaagc gcttcacttc cttcatagac actccatagt gcaccgagat   960
atcaagagtg acaacgtgct gctcggcatg aacggagagg ttaagctcac cgatatggga  1020
ttctgtgctc agattcagcc gggatcgaaa agagatactg tcgtcggaac tccatattgg  1080

```
atgtcgccgg agatattgaa caagaagcag tacaactata aggttgacat ttggtcgctg    1140
ggaattatgg ctctagagat gattgatgga gagccaccat atttgagaga aacacctttg    1200
aaggctatct acttgattgc tcaaaacggg aagccagaga tcaagcaacg cgacagactg    1260
tcttcagagt tcaacaattt ccttgacaag tgtcttgttg ttgatccgga tcagagagcc    1320
gatacaacgg agctcttggc acatccattc ctgaaaaagg cgaagccact ctcaagcctg    1380
attccataca tcagagccgt ccgagaaaag tagacccagc tttcttgtac aaagttggca    1440
ttataagaaa gcattgctta tcaatttgtt gcaacgaaca ggtcactatc agtcaaaata    1500
aaatcattat ttgccatcca gctgcagctc tggcccgtgt ctcaaaatct ctgatgttac    1560
attgcacaag ataaaaatat atcatcatga acaataaaac tgtctgctta cataaacagt    1620
aatacaaggg gtgttatgag ccatattcaa cgggaaacgt cgaggccgcg attaaattcc    1680
aacatggatg ctgatttata tgggtataaa tgggctcgcg ataatgtcgg gcaatcaggt    1740
gcgacaatct atcgcttgta tgggaagccc gatgcgccag agttgtttct gaaacatggc    1800
aaaggtagcg ttgccaatga tgttacagat gagatggtca gactaaactg gctgacggaa    1860
tttatgcctc ttccgaccat caagcatttt atccgtactc ctgatgatgc atggttactc    1920
accactgcga tccccggaaa aacagcattc caggtattag aagaatatcc tgattcaggt    1980
gaaaatattg ttgatgcgct ggcagtgttc ctgcgccggt tgcattcgat tcctgtttgt    2040
aattgtcctt ttaacagcga tcgcgtattt cgtctcgctc aggcgcaatc acgaatgaat    2100
aacggtttgg ttgatgcgag tgattttgat gacgagcgta atggctggcc tgttgaacaa    2160
gtctggaaag aaatgcataa acttttgcca ttctcaccgg attcagtcgt cactcatggt    2220
gatttctcac ttgataacct tattttgac gaggggaaat taataggttg tattgatgtt    2280
ggacgagtcg gaatcgcaga ccgataccag gatcttgcca tcctatggaa ctgcctcggt    2340
gagttttctc cttcattaca gaaacggctt tttcaaaaat atggtattga taatcctgat    2400
atgaataaat tgcagtttca tttgatgctc gatgagtttt tctaatcaga attggttaat    2460
tggttgtaac actggcagag cattacgctg acttgacggg acggcgcaag ctcatgacca    2520
aaatccctta acgtgagttt tcgttccact gagcgtcaga ccccgtagaa aagatcaaag    2580
gatcttcttg agatcctttt tttctgcgcg taatctgctg cttgcaaaca aaaaaaccac    2640
cgctaccagc ggtggtttgt ttgccggatc aagagctacc aactctttt ccgaaggtaa    2700 ctggcttcag cagagcgcag ataccaaata ctgtccttct agtgtagccg tagttaggcc    2760
accacttcaa gaactctgta gcaccgccta catacctcgc tctgctaatc ctgttaccag    2820
tggctgctgc cagtggcgat aagtcgtgtc ttaccgggtt ggactcaaga cgatagttac    2880
cggataaggc gcagcggtcg ggctgaacgg ggggttcgtg cacacagccc agcttggagc    2940
gaacgaccta caccgaactg agatacctac agcgtgagct atgagaaagc gccacgcttc    3000
ccgaagggag aaaggcggac aggtatccgg taagcggcag ggtcggaaca ggagagcgca    3060
cgagggagct tccaggggga aacgcctggt atctttatag tcctgtcggg tttcgccacc    3120
tctgacttga gcgtcgattt ttgtgatgct cgtcaggggg cggagcctat ggaaaaacg    3180 ccagcaacgc ggccttttta cggttcctgg ccttttgctg gccttttgct cacatgttct    3240
ttcctgcgtt atcccctgat tctgtggata accgtattac cgctagccag gaagagtttg    3300
tagaaacgca aaaaggccat ccgtcaggat ggccttctgc ttagtttgat gcctggcagt    3360
ttatggcggg cgtcctgccc gccacccctc gggccgttgc ttcacaacgt tcaaatccgc    3420
```

-continued

| | |
|---|---|
| tcccggcgga tttgtcctac tcaggagagc gttcaccgac aaacaacaga taaaacgaaa | 3480 |
| ggcccagtct tccgactgag cctttcgttt tatttgatgc ctggcagttc cctactctcg | 3540 |
| c | 3541 |

<210> SEQ ID NO 14
<211> LENGTH: 4201
<212> TYPE: DNA
<213> ORGANISM: Artificial Sequence
<220> FEATURE:
<223> OTHER INFORMATION: Description of Artificial Sequence:Vector

<400> SEQUENCE: 14

| | |
|---|---|
| gttaacgcta gcatggatct cgggcgccaa ataatgattt tattttgact gatagtgacc | 60 |
| tgttcgttgc aacaaattga tgagcaatgc ttttttataa tgccaacttt gtacaaaaaa | 120 |
| gcaggctcaa aaatgtcaac ttcaaaaagt tccaaggtgc gaatacggaa tttcatcggg | 180 |
| cgaatcttct ctcccagcga taaagacaag gatcgagacg atgagatgaa gccatcctcg | 240 |
| tccgcaatgg atattagtca gccatataac acagtgcatc gagtccacgt tggatacgac | 300 |
| ggccagaagt tcagcggact gccgcaacca tggatggata ttcttctccg agacattagt | 360 |
| cttgccgatc agaagaagga tccgaacgcg gtggtgactg cgttgaagtt ctacgcacaa | 420 |
| tcaatgaagg agaacgagaa gacgaaattc atgacgacga atagtgtttt cacgaatagc | 480 |
| gatgacgatg atgtggacgt tcagttgacc ggacaagtca cggaacattt gaggaatttg | 540 |
| cagtgtagta atggttccgc aacttcccca tctacatcag tgtcagcttc atcttcttct | 600 |
| gctcgtccac tgacaaatgg aaataatcat cttttcacgg cgtcgtctac cgacacatct | 660 |
| ctctcattat cggaaaggaa taacgttccg tctccagctc cagttccata tagtgaaagt | 720 |
| gctccacaac tgaaaacatt caccggagag actccaaaac tgcatccacg atctccgttc | 780 |
| ccgcctcaac cgccagttct tccgcaacga agcaaaaccg catcggcagt ggcgacgacg | 840 |
| acgacgaatc cgacgacttc gaatggagca ccaccaccag ttcctggatc gaaaggaccc | 900 |
| ccggtgccac cgaaaccatc gcatctgaaa atcgcatcgt cgacagtatc ctcgggatgc | 960 |
| tcgtctccac aacagtattc gtctgctcga tccgttggta actcgctctc caacggcagt | 1020 |
| gttgtctcca caacatcgtc agatggtgat gtgcaattgt cgaataagga aaattcgaat | 1080 |
| gacaaatcag ttggagacaa gaatgggaac accaccacaa acaaaacgac cgtcgaacca | 1140 |
| cctccaccag aagagccacc tgttcgtgtt cgagcatctc atcgtgaaaa gctttctgat | 1200 |
| tccgaagtgc tcaatcaact ccgcgagatt gttaatccaa gtaatccact tggaaagtac | 1260 |
| gagatgaaga agcaaatcgg tgttggagca tccggaactg tattcgttgc taatgtggcc | 1320 |
| ggcagcactg atgtggtggc tgtgaagaga atggctttca agactcagcc gaagaaggag | 1380 |
| atgttgctca ccgagattaa ggttatgaag cagtatcgac acccgaacct cgtcaactac | 1440 |
| attgaatcgt atcggttga tgctgatgat ctttgggtag tgatggatta tctggaaggt | 1500 |
| ggaaacttga cagatgtcgt tgtgaagact gagttggacg aaggacaaat tgcagcagtt | 1560 |
| ttgcaagaat gtcttaaagc gcttcacttc cttcatagac actccatagt gcaccgagat | 1620 |
| atcaagagtg acaacgtgct gctcggcatg aacggagagg ttaagctcac cgatatggga | 1680 |
| ttctgtgctc agattcagcc gggatcgaaa agagatactg tcgtcggaac tccatattgg | 1740 |
| atgtcgccgg agatattgaa caagaagcag tacaactata aggttgacat ttggtcgctg | 1800 |
| ggaattatgg ctctagagat gattgatgga gagccaccat atttgagaga acacctttg | 1860 |
| aaggctatct acttgattgc tcaaaacggg aagccagaga tcaagcaacg cgacagactg | 1920 |

```
tcttcagagt tcaacaattt ccttgacaag tgtcttgttg ttgatccgga tcagagagcc   1980
gatacaacgg agctcttggc acatccattc ctgaaaaagg cgaagccact ctcaagcctg   2040
attccataca tcagagccgt ccgagaaaag tagacccagc tttcttgtac aaagttggca   2100
ttataagaaa gcattgctta tcaatttgtt gcaacgaaca ggtcactatc agtcaaaata   2160
aaatcattat ttgccatcca gctgcagctc tggcccgtgt ctcaaaatct ctgatgttac   2220
attgcacaag ataaaaatat atcatcatga acaataaaac tgtctgctta cataaacagt   2280
aatacaaggg gtgttatgag ccatattcaa cgggaaacgt cgaggccgcg attaaattcc   2340
aacatggatg ctgatttata tgggtataaa tgggctcgcg ataatgtcgg gcaatcaggt   2400
gcgacaatct atcgcttgta tgggaagccc gatgcgccag agttgtttct gaaacatggc   2460
aaaggtagcg ttgccaatga tgttacagat gagatggtca gactaaactg gctgacggaa   2520
tttatgcctc ttccgaccat caagcatttt atccgtactc ctgatgatgc atggttactc   2580
accactgcga tccccggaaa aacagcattc caggtattag aagaatatcc tgattcaggt   2640
gaaaatattg ttgatgcgct ggcagtgttc ctgcgccggt tgcattcgat tcctgttttgt   2700
aattgtcctt ttaacagcga tcgcgtattt cgtctcgctc aggcgcaatc acgaatgaat   2760
aacggtttgg ttgatgcgag tgattttgat gacgagcgta atggctggcc tgttgaacaa   2820
gtctggaaag aaatgcataa acttttgcca ttctcaccgg attcagtcgt cactcatggt   2880
gatttctcac ttgataacct tatttttgac gaggggaaat taataggttg tattgatgtt   2940
ggacgagtcg gaatcgcaga ccgataccag gatcttgcca tcctatggaa ctgcctcggt   3000
gagttttctc cttcattaca gaaacggctt tttcaaaaat atggtattga taatcctgat   3060
atgaataaat tgcagtttca tttgatgctc gatgagtttt tctaatcaga attggttaat   3120
tggttgtaac actggcagag cattacgctg acttgacggg acggcgcaag ctcatgacca   3180
aaatccctta acgtgagttt tcgttccact gagcgtcaga ccccgtagaa aagatcaaag   3240
gatcttcttg agatcctttt tttctgcgcg taatctgctg cttgcaaaca aaaaaaccac   3300
cgctaccagc ggtggtttgt ttgccggatc aagagctacc aactcttttt ccgaaggtaa   3360
ctggcttcag cagagcgcag ataccaaata ctgtccttct agtgtagccg tagttaggcc   3420
accacttcaa gaactctgta gcaccgccta catacctcgc tctgctaatc ctgttaccag   3480
tggctgctgc cagtggcgat aagtcgtgtc ttaccgggtt ggactcaaga cgatagttac   3540
cggataaggc gcagcggtcg ggctgaacgg ggggttcgtg cacacagccc agcttggagc   3600
gaacgaccta caccgaactg agatacctac agcgtgagct atgagaaagc gccacgcttc   3660
ccgaagggag aaaggcggac aggtatccgg taagcggcag ggtcggaaca ggagagcgca   3720
cgagggagct ccaggggga acgcctggt atctttatag tcctgtcggg tttcgccacc   3780
tctgacttga gcgtcgattt ttgtgatgct cgtcaggggg gcggagccta tggaaaaacg   3840
ccagcaacgc ggccttttta cggttcctgg ccttttgctg gccttttgct cacatgttct   3900
ttcctgcgtt atcccctgat tctgtggata accgtattac cgctagccag gaagagtttg   3960
tagaaacgca aaaaggccat ccgtcaggat ggccttctgc ttagtttgat gcctggcagt   4020
ttatggcggg cgtcctgccc gccacccctcc gggccgttgc ttcacaacgt tcaaatccgc   4080
tcccggcgga tttgtcctac tcaggagagc gttcaccgac aaacaacaga taaaacgaaa   4140
ggcccagtct tccgactgag cctttcgttt tatttgatgc ctggcagttc cctactctcg   4200
c                                                                   4201
```

-continued

<210> SEQ ID NO 15
<211> LENGTH: 4278
<212> TYPE: DNA
<213> ORGANISM: Artificial Sequence
<220> FEATURE:
<223> OTHER INFORMATION: Description of Artificial Sequence:Vector

<400> SEQUENCE: 15

| | | | | | |
|---|---|---|---|---|---|
| gttaacgcta | gcatggatct | cgggccccaa | ataatgattt | tattttgact | gatagtgacc | 60 |
| tgttcgttgc | aacaaattga | tgagcaatgc | tttttttataa | tgccaacttt | gtacaaaaaa | 120 |
| gcaggctggt | ttaattaccc | aagtttgaga | tttaccttaa | catcgggtct | gacaaccgtg | 180 |
| tcgcttacga | cgcattctaa | tcattaacca | tgtcaacttc | aaaaagttcc | aaggtgcgaa | 240 |
| tacggaattt | catcgggcga | atcttctctc | ccagcgataa | agacaaggat | cgagacgatg | 300 |
| agatgaagcc | atcctcgtcc | gcaatggata | ttagtcagcc | atataacaca | gtgcatcgag | 360 |
| tccacgttgg | atacgacggc | cagaagttca | gcggactgcc | gcaaccatgg | atggatattc | 420 |
| ttctccgaga | cattagtctt | gccgatcaga | agaaggatcc | gaacgcggtg | gtgactgcgt | 480 |
| tgaagttcta | cgcacaatca | atgaaggaga | acgagaagac | gaaattcatg | acgacgaata | 540 |
| gtgttttcac | gaatagcgat | gacgatgatg | tggacgttca | gttgaccgga | caagtcacgg | 600 |
| aacatttgag | gaatttgcag | tgtagtaatg | gttccgcaac | ttccccatct | acatcagtgt | 660 |
| cagcttcatc | ttcttctgct | cgtccactga | caaatggaaa | taatcatctt | tccacggcgt | 720 |
| cgtctaccga | cacatctctc | tcattatcgg | aaaggaataa | cgttccgtct | ccagctccag | 780 |
| ttccatatag | tgaaagtgct | ccacaactga | aaacattcac | cggagagact | ccaaaactgc | 840 |
| atccacgatc | tccgttcccg | cctcaaccgc | cagttcttcc | gcaacgaagc | aaaaccgcat | 900 |
| cggcagtggc | gacgacgacg | acgaatccga | cgacttcgaa | tggagcacca | ccaccagttc | 960 |
| ctggatcgaa | aggaccccg | gtgccaccga | accatcgca | tctgaaaatc | gcatcgtcga | 1020 |
| cagtatcctc | gggatgctcg | tctccacaac | agtattcgtc | tgctcgatcc | gttggtaact | 1080 |
| cgctctccaa | cggcagtgtt | gtctccacaa | catcgtcaga | tggtgatgtg | caattgtcga | 1140 |
| ataaggaaaa | ttcgaatgac | aaatcagttg | gagacaagaa | tgggaacacc | accacaaaca | 1200 |
| aaacgaccgt | cgaaccacct | ccaccagaag | agccacctgt | tcgtgttcga | gcatctcatc | 1260 |
| gtgaaaagct | ttctgattcc | gaagtgctca | atcaactccg | cgagattgtt | aatccaagta | 1320 |
| atccacttgg | aaagtacgag | atgaagaagc | aaatcggtgt | tggagcatcc | ggaactgtat | 1380 |
| tcgttgctaa | tgtgccggc | agcactgatg | tggtggctgt | gaagagaatg | gctttcaaga | 1440 |
| ctcagccgaa | gaaggagatg | ttgctcaccg | agattaaggt | tatgaagcag | tatcgacacc | 1500 |
| cgaacctcgt | caactacatt | gatcgtatc | tggttgatgc | tgatgatctt | tgggtagtga | 1560 |
| tggattatct | ggaaggtgga | aacttgacag | atgtcgttgt | gaagactgag | ttggacgaag | 1620 |
| gacaaattgc | agcagttttg | caagaatgtc | ttaaagcgct | tcacttcctt | catagacact | 1680 |
| ccatagtgca | ccgagatatc | aagagtgaca | acgtgctgct | cggcatgaac | ggagaggtta | 1740 |
| agctcaccga | tatgggattc | tgtgctcaga | ttcagccggg | atcgaaaaga | gatactgtcg | 1800 |
| tcggaactcc | atattggatg | tcgccggaga | tattgaacaa | gaagcagtac | aactataagg | 1860 |
| ttgacatttg | gtcgctggga | attatggccc | tagagatgat | tgatgagag | ccaccatatt | 1920 |
| tgagagaaac | acctttgaag | gctatctact | tgattgctca | aacgggaag | ccagagatca | 1980 |
| agcaacgcga | cagactgtct | tcagagttca | acaatttcct | tgacaagtgt | cttgttgttg | 2040 |
| atccggatca | gagagccgat | acaacggagc | tcttggcaca | tccattcctg | aaaaggcga | 2100 |

-continued

```
agccactctc aagcctgatt ccatacatca gagccgtccg agaaaagtag acccagcttt    2160
cttgtacaaa gttggcatta taagaaagca ttgcttatca atttgttgca acgaacaggt    2220
cactatcagt caaataaaaa tcattatttg ccatccagct gcagctctgg cccgtgtctc    2280
aaaatctctg atgttacatt gcacaagata aaaatatatc atcatgaaca ataaaactgt    2340
ctgcttacat aaacagtaat acaaggggtg ttatgagcca tattcaacgg gaaacgtcga    2400
ggccgcgatt aaattccaac atggatgctg atttatatgg gtataaatgg gctcgcgata    2460
atgtcgggca atcaggtgcg acaatctatc gcttgtatgg gaagcccgat gcgccagagt    2520
tgtttctgaa acatggcaaa ggtagcgttg ccaatgatgt tacagatgag atggtcagac    2580
taaactggct gacggaattt atgcctcttc cgaccatcaa gcattttatc cgtactcctg    2640
atgatgcatg gttactcacc actgcgatcc ccggaaaaac agcattccag gtattagaag    2700
aatatcctga ttcaggtgaa atattgttga tgcgctggc agtgttcctg cgccggttgc    2760
attcgattcc tgtttgtaat tgtcctttta acagcgatcg cgtatttcgt ctcgctcagg    2820
cgcaatcacg aatgaataac ggtttggttg atgcgagtga ttttgatgac gagcgtaatg    2880
gctggcctgt tgaacaagtc tggaaagaaa tgcataaact tttgccattc tcaccggatt    2940
cagtcgtcac tcatggtgat ttctcacttg ataaccttat ttttgacgag gggaaattaa    3000
taggttgtat tgatgttgga cgagtcggaa tcgcagaccg ataccaggat cttgccatcc    3060
tatggaactg cctcggtgag ttttctcctt cattacagaa acggcttttt caaaaatatg    3120
gtattgataa tcctgatatg aataaattgc agtttcattt gatgctcgat gagttttttct    3180 aatcagaatt ggttaattgg ttgtaacact ggcagagcat tacgctgact tgacgggacg    3240
gcgcaagctc atgaccaaaa tcccttaacg tgagttttcg ttccactgag cgtcagaccc    3300
cgtagaaaag atcaaaggat cttcttgaga tcctttttttt ctgcgcgtaa tctgctgctt    3360
gcaaacaaaa aaaccaccgc taccagcggt ggtttgtttg ccggatcaag agctaccaac    3420 tcttttttccg aaggtaactg gcttcagcag agcgcagata ccaaatactg tccttctagt    3480
gtagccgtag ttaggccacc acttcaagaa ctctgtagca ccgcctacat acctcgctct    3540
gctaatcctg ttaccagtgg ctgctgccag tggcgataag tcgtgtctta ccgggttgga    3600
ctcaagacga tagttaccgg ataaggcgca gcggtcgggc tgaacggggg gttcgtgcac    3660
acagcccagc ttggagcgaa cgacctacac cgaactgaga tacctacagc gtgagctatg    3720
agaaagcgcc acgcttcccg aagggagaaa ggcggacagg tatccggtaa gcggcagggt    3780
cggaacagga gagcgcacga gggagcttcc agggggaaac gcctggtatc tttatagtcc    3840
tgtcgggttt cgccacctct gacttgagcg tcgatttttg tgatgctcgt caggggggcg    3900
gagcctatgg aaaaacgcca gcaacgcggc ctttttacgg ttcctggcct tttgctggcc    3960
ttttgctcac atgttctttc ctgcgttatc ccctgattct gtggataacc gtattaccgc    4020
tagccaggaa gagtttgtag aaacgcaaaa aggccatccg tcaggatggc cttctgctta    4080
gtttgatgcc tggcagttta tggcgggcgt cctgcccgcc accctccggg ccgttgcttc    4140
acaacgttca aatccgctcc cggcggattt gtcctactca ggagagcgtt caccgacaaa    4200
caacagataa aacgaaaggc ccagtcttcc gactgagcct tcgtttttat ttgatgcctg    4260
gcagttccct actctcgc                                                 4278
```

<210> SEQ ID NO 16
<211> LENGTH: 4207
<212> TYPE: DNA

<213> ORGANISM: Artificial Sequence
<220> FEATURE:
<223> OTHER INFORMATION: Description of Artificial Sequence:Vector

<400> SEQUENCE: 16

| | | | | | |
|---|---|---|---|---|---|
| gttaacgcta | gcatggatct | cgggccccaa | ataatgattt | tattttgact | gatagtgacc | 60 |
| tgttcgttgc | aacaaattga | tgagcaatgc | tttttataa | tgccaacttt | gtacaaaaaa | 120 |
| gcaggctcaa | aaatgtcaac | ttcaaaaagt | tccaaggtgc | gaatacggaa | tttcatcggg | 180 |
| cgaatcttct | ctcccagcga | taaagacaag | gatcgagacg | atgagatgaa | gccatcctcg | 240 |
| tccgcaatgg | atattagtca | gccatataac | acagtgcatc | gagtccacgt | tggatacgac | 300 |
| ggccagaagt | tcagcggact | gccgcaacca | tggatggata | ttcttctccg | agacattagt | 360 |
| cttgccgatc | agaagaagga | tccgaacgcg | gtggtgactg | cgttgaagtt | ctacgcacaa | 420 |
| tcaatgaagg | agaacgagaa | gacgaaattc | atgacgacga | atagtgtttt | cacgaatagc | 480 |
| gatgacgatg | atgtggacgt | tcagttgacc | ggacaagtca | cggaacattt | gaggaatttg | 540 |
| cagtgtagta | atggttccgc | aacttcccca | tctacatcag | tgtcagcttc | atcttcttct | 600 |
| gctcgtccac | tgacaaatgg | aaataatcat | cttttccacgg | cgtcgtctac | cgacacatct | 660 |
| ctctcattat | cggaaaggaa | taacgttccg | tctccagctc | cagttccata | tagtgaaagt | 720 |
| gctccacaac | tgaaaacatt | caccggagag | actccaaaac | tgcatccacg | atctccgttc | 780 |
| ccgcctcaac | cgccagttct | tccgcaacga | agcaaaaccg | catcggcagt | ggcgacgacg | 840 |
| acgacgaatc | cgacgacttc | gaatggagca | ccaccaccag | ttcctggatc | gaaaggaccc | 900 |
| ccggtgccac | cgaaaccatc | gcatctgaaa | atcgcatcgt | cgacagtatc | ctcgggatgc | 960 |
| tcgtctccac | aacagtattc | gtctgctcga | tccgttggta | actcgctctc | caacggcagt | 1020 |
| gttgtctcca | caacatcgtc | agatggtgat | gtgcaattgt | cgaataagga | aaattcgaat | 1080 |
| gacaaatcag | ttggagacaa | gaatgggaac | accaccacaa | acaaaacgac | cgtcgaacca | 1140 |
| cctccaccag | aagagccacc | tgttcgtgtt | cgagcatctc | atcgtgaaaa | gctttctgat | 1200 |
| tccgaagtgc | tcaatcaact | ccgcgagatt | gttaatccaa | gtaatccact | tggaaagtac | 1260 |
| gagatgaaga | agcaaatcgg | tgttggagca | tccggaactg | tattcgttgc | taatgtggcc | 1320 |
| ggcagcactg | atgtggtggc | tgtgaagaga | atggctttca | agactcagcc | gaagaaggag | 1380 |
| atgttgctca | ccgagattaa | ggttatgaag | cagtatcgac | acccgaacct | cgtcaactac | 1440 |
| attgaatcgt | atctggttga | tgctgatgat | ctttgggtag | tgatggatta | tctgaaggt | 1500 |
| ggaaacttga | cagatgtcgt | tgtgaagact | gagttggacg | aaggacaaat | tgcagcagtt | 1560 |
| ttgcaagaat | gtcttaaagc | gcttcacttc | cttcatagac | actccatagt | gcaccgagat | 1620 |
| atcaagagtg | acaacgtgct | gctcggcatg | aacggagagg | ttaagctcac | cgatatggga | 1680 |
| ttctgtgctc | agattcagcc | gggatcgaaa | agttgtagag | atactgtcgt | cggaactcca | 1740 |
| tattggatgt | cgccggagat | attgaacaag | aagcagtaca | actataaggt | tgacatttgg | 1800 |
| tcgctgggaa | ttatggcct | agagatgatt | gatggagagc | caccatattt | gagagaaaca | 1860 |
| cctttgaagg | ctatctactt | gattgctcaa | acgggaagc | cagagatcaa | gcaacgcgac | 1920 |
| agactgtctt | cagagttcaa | caatttcctt | gacaagtgtc | ttgttgttga | tccggatcag | 1980 |
| agagccgata | caacgagct | cttggcacat | ccattcctga | aaaaggcgaa | gccactctca | 2040 |
| agcctgattc | catacatcag | agccgtccga | gaaaagtaga | cccagctttc | ttgtacaaag | 2100 |
| ttggcattat | aagaaagcat | tgcttatcaa | tttgttgcaa | cgaacaggtc | actatcagtc | 2160 |
| aaaataaaat | cattatttgc | catccagctg | cagctctggc | ccgtgtctca | aaatctctga | 2220 |

```
tgttacattg cacaagataa aaatatatca tcatgaacaa taaaactgtc tgcttacata   2280
aacagtaata caagggtgt tatgagccat attcaacggg aaacgtcgag gccgcgatta   2340
aattccaaca tggatgctga tttatatggg tataaatggg ctcgcgataa tgtcgggcaa   2400
tcaggtgcga caatctatcg cttgtatggg aagcccgatg cgccagagtt gtttctgaaa   2460
catggcaaag gtagcgttgc caatgatgtt acagatgaga tggtcagact aaactggctg   2520
acggaattta tgcctcttcc gaccatcaag cattttatcc gtactcctga tgatgcatgg   2580
ttactcacca ctgcgatccc cggaaaaaca gcattccagg tattagaaga atatcctgat   2640
tcaggtgaaa atattgttga tgcgctggca gtgttcctgc gccggttgca ttcgattcct   2700
gtttgtaatt gtcctttaa cagcgatcgc gtatttcgtc tcgctcaggc gcaatcacga   2760
atgaataacg gtttggttga tgcgagtgat tttgatgacg agcgtaatgg ctggcctgtt   2820
gaacaagtct ggaaagaaat gcataaactt ttgccattct caccggattc agtcgtcact   2880
catggtgatt tctcacttga taaccttatt tttgacgagg ggaaattaat aggttgtatt   2940
gatgttggac gagtcggaat cgcagaccga taccaggatc ttgccatcct atggaactgc   3000
ctcggtgagt tttctccttc attacagaaa cggctttttc aaaaatatgg tattgataat   3060
cctgatatga ataaattgca gtttcatttg atgctcgatg agtttttcta atcagaattg   3120
gttaattggt tgtaacactg gcagagcatt acgctgactt gacgggacgg cgcaagctca   3180
tgaccaaaat cccttaacgt gagttttcgt tccactgagc gtcagacccc gtagaaaaga   3240
tcaaaggatc ttcttgagat cctttttttc tgcgcgtaat ctgctgcttg caaacaaaaa   3300
aaccaccgct accagcggtg gtttgtttgc cggatcaaga gctaccaact cttttttccga   3360 aggtaactgg cttcagcaga gcgcagatac caaatactgt ccttctagtg tagccgtagt   3420
taggccacca cttcaagaac tctgtagcac cgcctacata cctcgctctg ctaatcctgt   3480
taccagtggc tgctgccagt ggcgataagt cgtgtcttac cgggttggac tcaagacgat   3540
agttaccgga taaggcgcag cggtcgggct gaacgggggg ttcgtgcaca cagcccagct   3600
tggagcgaac gacctacacc gaactgagat acctacagcg tgagctatga aaagcgcca   3660 cgcttcccga agggagaaag gcggacaggt atccggtaag cggcagggtc ggaacaggag   3720
agcgcacgag ggagcttcca gggggaaacg cctggtatct ttatagtcct gtcgggtttc   3780
gccacctctg acttgagcgt cgatttttgt gatgctcgtc agggggggcgg agcctatgga   3840 aaaacgccag caacgcggcc tttttacggt tcctggcctt ttgctggcct tttgctcaca   3900
tgttctttcc tgcgttatcc cctgattctg tggataaccg tattaccgct agccaggaag   3960
agtttgtaga aacgcaaaaa ggccatccgt caggatggcc ttctgcttag tttgatgcct   4020
ggcagtttat ggcgggcgtc ctgcccgcca ccctccgggc cgttgcttca caacgttcaa   4080
atccgctccc ggcggatttg tcctactcag gagagcgttc accgacaaac aacagataaa   4140
acgaaaggcc cagtcttccg actgagcctt tcgttttatt tgatgcctgg cagttcccta   4200
ctctcgc                                                            4207
```

<210> SEQ ID NO 17
<211> LENGTH: 4066
<212> TYPE: DNA
<213> ORGANISM: Artificial Sequence
<220> FEATURE:
<223> OTHER INFORMATION: Description of Artificial Sequence:Vector

<400> SEQUENCE: 17

-continued

| | |
|---|---|
| gttaacgcta gcatggatct cgggccccaa ataatgattt tattttgact gatagtgacc | 60 |
| tgttcgttgc aacaaattga tgagcaatgc ttttttataa tgccaacttt gtacaaaaaa | 120 |
| gcaggctcaa aaatgtcaac ttcaaaaagt tccaaggtgc gaatacgaa tttcatcggg | 180 |
| cgaatcttct ctcccagcga taaagacaag gatcgagacg atgagatgaa gccatcctcg | 240 |
| tccgcaatgg atattagtca gccatataac acagtgcatc gagtccacgt tggatacgac | 300 |
| ggccagaagt tcagcggact gccgcaacca tggatggata ttcttctccg agacattagc | 360 |
| tatttcagtc ttgccgatca gaagaaggat ccgaacgcgg tggtgactgc gttgaagttc | 420 |
| tacgcacaat caatgaagga gaacgagaag acgaaattca tgacgacgaa tagtgttttc | 480 |
| acgaatagcg atgacgatga tgtggacgtt cagttgaccg gacaagtcac ggaacatttg | 540 |
| aggaatttgc agtgtagtaa tggttccgca acttccccat ctacatcagt gtcagcttca | 600 |
| tcttcttctg ctcgtccact gacaaatgga ataatcatc tttccacggc gtcgtctacc | 660 |
| gacacatctc tctcattatc ggaaaggaat aacgttccgt ctccagctcc agttccatat | 720 |
| agtgaaagtg ctccacaact gaaaacattc accggagaga ctccaaaact gcatccacga | 780 |
| tctccgttcc cgcctcaacc gccagttctt ccgcaacgaa gcaaaaccgc atcggcagtg | 840 |
| gcgacgacga cgacgaatcc gacgacttcg aatggagcac caccaccagt tcctggatcg | 900 |
| aaaggacccc cggtgccacc gaaaccatcg aaggaaaatt cgaatgacaa atcagttgga | 960 |
| gacaagaatg ggaacaccac cacaaacaaa cgaccgtcg aaccacctcc accagaagag | 1020 |
| ccacctgttc gtgttcgagc atctcatcgt gaaaagcttt ctgattccga agtgctcaat | 1080 |
| caactccgcg agattgttaa tccaagtaat ccacttggaa agtacgagat gaagaagcaa | 1140 |
| atcggtgttg gagcatccgg aactgtattc gttgctaatg tggccggcag cactgatgtg | 1200 |
| gtggctgtga agagaatggc tttcaagact cagccgaaga aggagatgtt gctcaccgag | 1260 |
| attaaggtta tgaagcagta tcgacacccg aacctcgtca actacattga atcgtatctg | 1320 |
| gttgatgctg atgatctttg ggtagtgatg gattatctgg aaggtggaaa cttgacagat | 1380 |
| gtcgttgtga agactgagtt ggacgaagga caaattgcag cagttttgca agaatgtctt | 1440 |
| aaagcgcttc acttccttca tagacactcc atagtgcacc gagatatcaa gagtgacaac | 1500 |
| gtgctgctcg gcatgaacgg agaggttaag ctcaccgata tgggattctg tgctcagatt | 1560 |
| cagccgggat cgaaaagaga tactgtcgtc ggaactccat attggatgtc gccggagata | 1620 |
| ttgaacaaga agcagtacaa ctataaggtt gacatttggt cgctgggaat tatggctcta | 1680 |
| gagatgattg atggagagcc accatatttg agagaaacac ctttgaaggc tatctacttg | 1740 |
| attgctcaaa acgggaagcc agagatcaag caacgcgaca gactgtcttc agagttcaac | 1800 |
| aatttccttg acaagtgtct tgttgttgat ccggatcaga gagccgatac aacgagctc | 1860 |
| ttggcacatc cattcctgaa aaaggcgaag ccactctcaa gcctgattcc atacatcaga | 1920 |
| gccgtccgag aaaagtagac ccagctttct tgtacaaagt tggcattata agaaagcatt | 1980 |
| gcttatcaat ttgttgcaac gaacaggtca ctatcagtca aaataaaatc attatttgcc | 2040 |
| atccagctgc agctctggcc cgtgtctcaa aatctctgat gttacattgc acaagataaa | 2100 |
| aatatatcat catgaacaat aaaactgtct gcttacataa acagtaatac aagggtgtt | 2160 |
| atgagccata ttcaacggga acgtcgagg ccgcgattaa attccaacat ggatgctgat | 2220 |
| ttatatgggt ataaatgggc tcgcgataat gtcgggcaat caggtgcgac aatctatcgc | 2280 |
| ttgtatggga agcccgatgc gccagagttg tttctgaaac atggcaaagg tagcgttgcc | 2340 |
| aatgatgtta cagatgagat ggtcagacta aactggctga cggaatttat gcctcttccg | 2400 |

-continued

```
accatcaagc attttatccg tactcctgat gatgcatggt tactcaccac tgcgatcccc      2460
ggaaaaacag cattccaggt attagaagaa tatcctgatt caggtgaaaa tattgttgat      2520
gcgctggcag tgttcctgcg ccggttgcat tcgattcctg tttgtaattg tccttttaac      2580
agcgatcgcg tatttcgtct cgctcaggcg caatcacgaa tgaataacgg tttggttgat      2640
gcgagtgatt ttgatgacga gcgtaatggc tggcctgttg aacaagtctg aaagaaatg       2700 cataaacttt tgccattctc accggattca gtcgtcactc atggtgattt ctcacttgat      2760
aaccttattt tgacgaggg gaaattaata ggttgtattg atgttggacg agtcggaatc       2820
gcagaccgat accaggatct tgccatccta tggaactgcc tcggtgagtt ttctccttca      2880
ttacagaaac ggcttttca aaaatatggt attgataatc ctgatatgaa taaattgcag       2940
tttcatttga tgctcgatga gttttctaa tcagaattgg ttaattggtt gtaacactgg       3000
cagagcatta cgctgacttg acgggacggc gcaagctcat gaccaaaatc ccttaacgtg      3060
agttttcgtt ccactgagcg tcagaccccg tagaaaagat caaggatctc tcttgagatc      3120 cttttttct gcgcgtaatc tgctgcttgc aaacaaaaaa accaccgcta ccagcggtgg       3180
tttgtttgcc ggatcaagag ctaccaactc ttttccgaa ggtaactggc ttcagcagag       3240
cgcagatacc aaatactgtc cttctagtgt agccgtagtt aggccaccac ttcaagaact      3300
ctgtagcacc gcctacatac ctcgctctgc taatcctgtt accagtggct gctgccagtg      3360
gcgataagtc gtgtcttacc gggttggact caagacgata gttaccggat aaggcgcagc      3420
ggtcgggctg aacggggggt tcgtgcacac agcccagctt ggagcgaacg acctacaccg      3480
aactgagata cctacagcgt gagctatgag aaagcgccac gcttcccgaa gggagaaagg      3540
cggacaggta tccggtaagc ggcagggtcg aacaggaga gcgcacgagg gagcttccag       3600
ggggaaacgc ctggtatctt tatagtcctg tcgggtttcg ccacctctga cttgagcgtc      3660
gatttttgtg atgctcgtca gggggggcgga gcctatggaa aaacgccagc aacgcggcct     3720
ttttacggtt cctggccttt tgctggcctt ttgctcacat gttctttcct gcgttatccc      3780
ctgattctgt ggataaccgt attaccgcta gccaggaaga gtttgtagaa acgcaaaaag      3840
gccatccgtc aggatggcct tctgcttagt ttgatgcctg gcagtttatg gcgggcgtcc      3900
tgcccgccac cctccgggcc gttgcttcac aacgttcaaa tccgctcccg gcggatttgt      3960
cctactcagg agagcgttca ccgacaaaca acagataaaa cgaaaggccc agtcttccga      4020
ctgagccttt cgttttattt gatgcctggc agttccctac tctcgc                    4066
```

<210> SEQ ID NO 18
<211> LENGTH: 4207
<212> TYPE: DNA
<213> ORGANISM: Artificial Sequence
<220> FEATURE:
<223> OTHER INFORMATION: Description of Artificial Sequence:Vector

<400> SEQUENCE: 18

```
gttaacgcta gcatggatct cgggcccccaa ataatgattt tattttgact gatagtgacc      60
tgttcgttgc aacaaattga tgagcaatgc ttttttataa tgccaacttt gtacaaaaaa      120
gcaggctcaa aaatgtcaac ttcaaaaagt tccaaggtgc gaatacgaaa tttcgtcggg      180
cgaatcttct ctcccagcga taaagacaag gatcgagacg atgagatgaa gccatcctcg      240
tccgcaatgg atattagtca gccatataac acagtgcatc gagtccacgt tggatacgac      300
ggccagaagt tcagcggact gccgcaacca tggatggata ttcttctccg agacattagt      360
```

-continued

```
cttgccgatc agaagaagga tccgaacgcg gtggtgactg cgttgaagtt ctacgcacaa      420
tcaatgaagg agaacgagaa gacgaaattc atgacgacga atagtgtttt cacgaatagc      480
gatgacgatg atgtggacgt tcagttgacc ggacaagtca cggaacattt gaggaatttg      540
cagtgtagta atggttccgc aacttcccca tctacatcag tgtcagcttc atcttcttct      600
gctcgtccac tgacaaatgg aaataatcat cttcccacgg cgtcgtctac cgacacatct      660
ctctcattat cggaaaggaa taacgttccg tctccagctc cagttccata tagtgaaagt      720
gctccacaac tgaaaacatt caccggagag actccaaaac tgcatccacg atctccgttc      780
ccgcctcaac cgccagttct tccgcaacga agcaaaaccg catcggcagt ggcgacgacg      840
acgacgaatc cgacgacttc gaatggagca ccaccaccag ttcctggatc gaaaggaccc      900
ccggtgccac cgaaaccatc gcatctgaaa atcgcatcgt cgacagtatc ctcgggatgc      960
tcgtctccac aacagtattc gtctgctcga tccgttggta actcgctctc caacggcagt     1020
gttgtctcca acatcgtc agatggtgat gtgcaattgt cgaataagga aaattcgaat     1080
gacaaatcag ttggagacaa gaatgggaac accaccacaa acaaaacgac cgtcgaacca     1140
cctccaccag aagagccacc tgttcgtgtt cgagcatctc atcgtgaaaa gctttctgat     1200
tccgaagtgc tcaatcaact ccgcgagatt gttaatccaa gtaatccact tggaaagtac     1260
gagatgaaga agcaaatcgg tgttggagca tccggaactg tattcgttgc taatgtggcc     1320
ggcagcactg atgtggtggc tgtgaagaga atggctttca agactcagcc gaagaaggag     1380
atgttgctca ccgagattaa ggttatgaag cagtatcgac acccgaacct cgtcaactac     1440
attgaatcgt atctggttga tgctgatgat ctttgggtag tgatggatta tctggaaggt     1500
ggaaacttga cagatgtcgt tgtgaagact gagttggacg aaggacaaat tgcagcagtt     1560
ttgcaagaat gtcttaaagc gcttcacttc cttcatagac actccatagt gcaccgagat     1620
atcaagagtg acaacgtgct gctcggcatg aacggagagg ttaagctcac cgatatggga     1680
ttctgtgctc agattcagcc gggatcgaaa agttgtagag atactgtcgt cggaactcca     1740
tattggatgt cgccggagat attgaacaag aagcagtaca actataaggt tgacatttgg     1800
tcgctgggaa ttatggctct agagatgatt gatggagagc caccatattt gagagaaaca     1860
cctttgaagg ctatctactt gattgctcaa acgggaagc cagagatcaa gcaacgcgac     1920
agactgtctt cagagttcaa caatttcctt gacaagtgtc ttgttgttga tccggatcag     1980
agagccgata caacggagct cttggcacat ccattcctga aaaaggcgaa gccactctca     2040
agcctgattc catacatcag agccgtccga gaaaagtaga cccagctttc ttgtacaaag     2100
ttggcattat aagaaagcat tgcttatcaa tttgttgcaa cgaacaggtc actatcagtc     2160
aaaataaaat cattatttgc catccagctg cagctctggc ccgtgtctca aaatctctga     2220
tgttacattg cacaagataa aaatatatca tcatgaacaa taaaactgtc tgcttacata     2280
aacagtaata caagggggtgt tatgagccat attcaacggg aaacgtcgag gccgcgatta     2340
aattccaaca tggatgctga tttatatggg tataaatggg ctcgcgataa tgtcgggcaa     2400
tcaggtgcga caatctatcg cttgtatggg aagcccgatg cgccagagtt gtttctgaaa     2460
catggcaaag gtagcgttgc caatgatgtt acagatgaga tggtcagact aaactggctg     2520
acggaattta tgcctcttcc gaccatcaag cattttatcc gtactcctga tgatgcatgg     2580
ttactcacca ctgcgatccc cggaaaaaca gcattccagg tattagaaga atatcctgat     2640
tcaggtgaaa atattgttga tgcgctggca gtgttcctgc gccggttgca ttcgattcct     2700
gtttgtaatt gtccttttaa cagcgatcgc gtatttcgtc tcgctcaggc gcaatcacga     2760
```

```
atgaataacg gtttggttga tgcgagtgat tttgatgacg agcgtaatgg ctggcctgtt    2820
gaacaagtct ggaaagaaat gcataaactt ttgccattct caccggattc agtcgtcact    2880
catggtgatt tctcacttga taaccttatt tttgacgagg ggaaattaat aggttgtatt    2940
gatgttggac gagtcggaat cgcagaccga taccaggatc ttgccatcct atggaactgc    3000
ctcggtgagt tttctccttc attacagaaa cggcttttc aaaaatatgg tattgataat     3060
cctgatatga ataaattgca gtttcatttg atgctcgatg agttttcta atcagaattg     3120 gttaattggt tgtaacactg gcagagcatt acgctgactt gacgggacgg cgcaagctca    3180
tgaccaaaat cccttaacgt gagttttcgt tccactgagc gtcagacccc gtagaaaaga    3240
tcaaaggatc ttcttgagat ccttttttc tgcgcgtaat ctgctgcttg caaacaaaaa     3300
aaccaccgct accagcggtg gtttgtttgc cggatcaaga ctaccaact cttttttccga    3360 aggtaactgg cttcagcaga gcgcagatac caaatactgt ccttctagtg tagccgtagt    3420
taggccacca cttcaagaac tctgtagcac cgcctacata cctcgctctg ctaatcctgt    3480
taccagtggc tgctgccagt ggcgataagt cgtgtcttac cgggttggac tcaagacgat    3540
agttaccgga taaggcgcag cggtcgggct gaacggggg ttcgtgcaca cagcccagct     3600
tggagcgaac gacctacacc gaactgagat acctacagcg tgagctatga aaagcgcca     3660 cgcttcccga agggagaaag gcggacaggt atccggtaag cggcagggtc ggaacaggag    3720
agcgcacgag ggagcttcca gggggaaacg cctggtatct ttatagtcct gtcgggtttc    3780
gccacctctg acttgagcgt cgatttttgt gatgctcgtc agggggggcgg agcctatgga   3840 aaaacgccag caacgcggcc tttttacggt tcctggcctt ttgctggcct tttgctcaca    3900
tgttctttcc tgcgttatcc cctgattctg tggataaccg tattaccgct agccaggaag    3960
agtttgtaga aacgcaaaaa ggccatccgt caggatggcc ttctgcttag tttgatgcct    4020
ggcagtttat gcgggcgtc ctgcccgcca ccctccgggc cgttgcttca caacgttcaa     4080
atccgctccc ggcggatttg tcctactcag gagagcgttc accgacaaac aacagataaa    4140
acgaaaggcc cagtcttccg actgagcctt tcgttttatt tgatgcctgg cagttcccta    4200
ctctcgc                                                              4207
```

<210> SEQ ID NO 19
<211> LENGTH: 29
<212> TYPE: DNA
<213> ORGANISM: Primer

<400> SEQUENCE: 19
ggggacaagt ttgtacaaaa aagcaggct                                        29

<210> SEQ ID NO 20
<211> LENGTH: 29
<212> TYPE: DNA
<213> ORGANISM: Primer

<400> SEQUENCE: 20
ggggaccact ttgtacaaga aagctgggt                                        29

<210> SEQ ID NO 21
<211> LENGTH: 40
<212> TYPE: DNA
<213> ORGANISM: Primer

<400> SEQUENCE: 21

-continued aaaaagcagg ctcaaaaatg tttcaaaata gtccgatgat 40

<210> SEQ ID NO 22
<211> LENGTH: 33
<212> TYPE: DNA
<213> ORGANISM: Primer

<400> SEQUENCE: 22
agaaagctgg gtctactttt ctcggacggc tct 33

<210> SEQ ID NO 23
<211> LENGTH: 34
<212> TYPE: DNA
<213> ORGANISM: Primer

<400> SEQUENCE: 23
aaaaagcagg ctggtttaat tacccaagtt tgag 34

<210> SEQ ID NO 24
<211> LENGTH: 33
<212> TYPE: DNA
<213> ORGANISM: Primer

<400> SEQUENCE: 24
agaaagctgg gtctactttt ctcggacggc tct 33

<210> SEQ ID NO 25
<211> LENGTH: 41
<212> TYPE: DNA
<213> ORGANISM: Primer

<400> SEQUENCE: 25
aaaaagcagg ctcaaaaatg tcaacttcaa aaagttccaa g 41

<210> SEQ ID NO 26
<211> LENGTH: 4447
<212> TYPE: DNA
<213> ORGANISM: Artificial Sequence
<220> FEATURE:
<223> OTHER INFORMATION: Description of Artificial Sequence:Vector

<400> SEQUENCE: 26
aacctggctt atcgaaatta atacgactca ctatagggag accggcagat ctgatatcac 60
aagtttgtac aaaaaagcag gctcaaaaat gaaagctttc tcatcgtatg atgagaaacc 120
accagcacca ccaattcgtt tcagcagctc ggcaacgagg gagaatcagg tcgtcggatt 180
gaagccattg cccaaagagc cagaagcaac caagaaaaag aagacgatgc ctaacccgtt 240
catgaaaaag aacaaagaca aaaaggaagc gtcagaaaaa ccagtgatct ctcgaccgag 300
caatttcgaa cacacaattc atgtcggata tgacccaaaa accggcgaat ttacgggaat 360
gcctgaagca tgggcacgtc ttctcacaga ctcacagatc tcaaaacaag agcagcaaca 420
gaatcctcag gcagtgttgg acgcgctcaa atactacaca caaggcgaaa gcagcggcca 480
gaagtggttg cagtacgata tgaatgacgc accttctcgg acgccatcat acggactgaa 540
accgcaacca tatagcacat catccctgcc gtatcatggc aataaaattc aggatccaag 600
aaagatgaat ccaatgacaa ccagtacaag tagtgcgggg tataacagca agcaggagt 660 tcctccgacg acgtttagtg taaatgagaa tagatcgagt atgccaccga gttatgcacc 720
gccaccggtc ccccatggtg aaactcctgc tgatattgtt cctcccgcta tccctgatag 780
gccggcaagg acgttgagta tttacacaaa accgaaagag gaggaagaaa aaattccaga 840

```
cctttcaaaa ggacaatttg gtgtacaggc cagaggtcaa aaagctaaga aaaagatgac    900
tgacgctgaa gtgctgacta agctccgtac cattgtgtct atcggaaatc cagatcgaaa    960
atatagaaaa gttgataaaa tcggctcagg tgcatctggt tctgtgtaca ccgctattga   1020
aattagtacc gaagcggagg tggctatcaa gcagatgaac ctgaaggatc aaccaaagaa   1080
ggaattgatc attaatgaga ttttggtgat gcgtgagaat aagcatgcaa atattgtaaa   1140
ttatttggat tcgtatttgg tgtgcgatga attatgggta gtgatggagt atcttgccgg   1200
tggatcattg actgatgttg tcacggagtg ccagatggag gatggaatta ttgcagctgt   1260
ttgcagagaa gttcttcaag cgcttgaatt cctccacagc cgccacgtca ttcacagaga   1320
tattaaatct gacaatattc ttttgggaat ggatggttcg gtgaaattga ccgactttgg   1380
attctgtgct cagctctcgc cggagcaaag aaaacgcacg acaatggtcg gaactccata   1440
ctggatggcg ccggaagtgg tgacccgcaa acaatacgga cccaaggttg atgtgtggtc   1500
cttgggaatc atggcgattg agatggtcga aggagaaccg ccatatttga atgaaaatcc   1560
actcagggct atctatctca ttgctacaaa tggcaaaccc gacttccctg aagagattc    1620 catgactttg ttgttcaagg actttgtcga ctctgcgttg gaagtacaag ttgaaaatcg   1680
atggtcggca agccaactcc ttacgcatcc attcctccga tgcgccaaac cgcttgcttc   1740
actgtactac ttaatcgttg cggcgaagaa gagcatcgcc gaagctagca actcataaac   1800
ccagctttct tgtacaaagt ggtgatatca gcttatcga taccgtcgac ctcgaggggg   1860
ggcccggtac ccaattcgcc ctatagtgag tcgtattacg cgcgctcact ggccgtcgtt   1920
ttacaacgtc gtgactggga aaaccctggc gttacccaac ttaatcgcct tgcagcacat   1980
ccccctttcg ccagctggcg taatagcgaa gaggcccgca ccgatcgccc ttcccaacag   2040
ttgcgcagcc tgaatggcga atgggacgcg ccctgtagcg gcgcattaag cgcggcgggt   2100
gtggtggtta cgcgcagcgt gaccgctaca cttgccagcg ccctagcgcc cgctcctttc   2160
gctttcttcc cttcctttct cgccacgttc gccggctttc ccgtcaagc tctaaatcgg   2220 gggctccctt tagggttccg atttagtgct ttacggcacc tcgaccccaa aaaacttgat   2280
tagggtgatg gttcacgtag tgggccatcg ccctgataga cggtttttcg ccctttgacg   2340
ttggagtcca cgttctttaa tagtggactc ttgttccaaa ctggaacaac actcaaccct   2400
atctcggtct attcttttga tttataaggg attttgccga tttcggccta ttggttaaaa   2460
aatgagctga tttaacaaaa atttaacgcg aattttaaca aaatattaac gcttacaatt   2520
taggtggcac ttttcgggga aatgtgcgcg gaacccctat ttgtttattt ttctaaatac   2580
attcaaatat gtatccgctc atgagacaat aaccctgata aatgcttcaa taatattgaa   2640
aaaggaagag tatgagtatt caacatttcc gtgtcgccct tattcccttt tttgcggcat   2700
tttgccttcc tgttttttgct cacccagaaa cgctggtgaa agtaaaagat gctgaagatc   2760
agttgggtgc acgagtgggt tacatcgaac tggatctcaa cagcggtaag atccttgaga   2820
gttttcgccc cgaagaacgt tttccaatga tgagcacttt taaagttctg ctatgtggcg   2880
cggtattatc ccgtattgac gccgggcaag agcaactcgg tcgccgcata cactattctc   2940
agaatgactt ggttgagtac tcaccagtca cagaaaagca tcttacggat ggcatgacag   3000
taagagaatt atgcagtgct gccataacca tgagtgataa cactgcggcc aacttacttc   3060
tgacaacgat cggaggaccg aaggagctaa ccgcttttt gcacaacatg gggatcatg    3120 taactcgcct tgatcgttgg gaaccggagc tgaatgaagc cataccaaac gacgagcgtg   3180
```

```
acaccacgat gcctgtagca atggcaacaa cgttgcgcaa actattaact ggcgaactac    3240
ttactctagc ttcccggcaa caattaatag actggatgga ggcggataaa gttgcaggac    3300
cacttctgcg ctcggccctt ccggctggct ggtttattgc tgataaatct ggagccggtg    3360
agcgtgggtc tcgcggtatc attgcagcac tggggccaga tggtaagccc tcccgtatcg    3420
tagttatcta cacgacgggg agtcaggcaa ctatggatga acgaaataga cagatcgctg    3480
agataggtgc ctcactgatt aagcattggt aactgtcaga ccaagtttac tcatatatac    3540
tttagattga tttaaaactt cattttaat ttaaaaggat ctaggtgaag atcctttttg     3600
ataatctcat gaccaaaatc ccttaacgtg agttttcgtt ccactgagcg tcagaccccg    3660
tagaaaagat caaaggatct tcttgagatc ctttttttct gcgcgtaatc tgctgcttgc    3720
aaacaaaaaa accaccgcta ccagcggtgg tttgtttgcc ggatcaagag ctaccaactc    3780 ttttccgaa ggtaactggc ttcagcagag cgcagatacc aaatactgtc cttctagtgt     3840
agccgtagtt aggccaccac ttcaagaact ctgtagcacc gcctacatac ctcgctctgc    3900
taatcctgtt accagtggct gctgccagtg gcgataagtc gtgtcttacc gggttggact    3960
caagacgata gttaccggat aaggcgcagc ggtcgggctg aacggggggt tcgtgcacac    4020
agcccagctt ggagcgaacg acctacaccg aactgagata cctacagcgt gagctatgag    4080
aaagcgccac gcttcccgaa gggagaaagg cggacaggta tccggtaagc ggcagggtcg    4140
gaacaggaga gcgcacgagg gagcttccag ggggaaacgc ctggtatctt tatagtcctg    4200
tcgggtttcg ccacctctga cttgagcgtc gatttttgtg atgctcgtca ggggggcgga    4260
gcctatggaa aaacgccagc aacgcggcct ttttacggtt cctggccttt tgctggcctt    4320
ttgctcacat gttctttcct gcgttatccc ctgattctgt ggataaccgt attaccgcct    4380
ttgagtgagc tgataccgct cgccgcagcc gaacgaccga gcgcagcgag tcagtgagcg    4440
aggaagc                                                              4447
```

<210> SEQ ID NO 27
<211> LENGTH: 3533
<212> TYPE: DNA
<213> ORGANISM: Artificial Sequence
<220> FEATURE:
<223> OTHER INFORMATION: Description of Artificial Sequence:Vector

<400> SEQUENCE: 27

```
aacctggctt atcgaaatta atacgactca ctatagggag accggcagat ctgatatcac      60
aagtttgtac aaaaaagcag gctcaaatcg gtgttggagc atccggaact gtattcgttg     120
ctaatgtggc cggcagcact gatgtggtgg ctgtgaagag aatggctttc aagactcagc     180
cgaagaagga gatgttgctc accgagatta aggttatgaa gcagtatcga cacccgaacc     240
tcgtcaacta cattgaatcg tatctggttg atgctgatga tctttgggta gtgatggatt     300
atctggaagg tggaaacttg acagatgtcg ttgtgaagac tgagttggac gaaggacaaa     360
ttgcagcagt tttgcaagaa tgtcttaaag cgcttcactt ccttcataga cactccatag     420
tgcaccgaga tatcaagagt gacaacgtgc tgctcggcat gaacggagag gttaagctca     480
ccgatatggg attctgtgct cagattcagc cgggatcgaa aagagatact gtcgtcggaa     540
ctccatattg gatgtcgccg gagatattga acaagaagca gtacaactat aaggttgaca     600
tttggtcgct gggaattatg gctctagaga tgattgatgg agagccacca tatttgagag     660
aaacaccttt gaaggctatc tacttgattg ctcaaaacgg gaagcagag atcaagcaac      720 gcgacagact gtcttcagag ttcaacaatt tccttgacaa gtgtcttgtt gttgatccgg     780
```

```
atcagagagc cgatacaacg gagctcttgg cacatccatt cctgaaaaag gcgaagccac    840
tctcaagcct gattccatac atcagagccg tccgagaaaa gtagacccag ctttcttgta    900
caaagtggtg atatcaagct tatcgatacc gtcgacctcg agggggggcc cggtacccaa    960
ttcgccctat agtgagtcgt attacgcgcg ctcactggcc gtcgttttac aacgtcgtga   1020
ctgggaaaac cctggcgtta cccaacttaa tcgccttgca gcacatcccc ctttcgccag   1080
ctggcgtaat agcgaagagg cccgcaccga tcgcccttcc caacagttgc gcagcctgaa   1140
tggcgaatgg gacgcgccct gtagcggcgc attaagcgcg gcgggtgtgg tggttacgcg   1200
cagcgtgacc gctacacttg ccagcgccct agcgcccgct cctttcgctt tcttcccttc   1260
ctttctcgcc acgttcgccg gctttccccg tcaagctcta aatcggggggc tccctttagg   1320
gttccgattt agtgctttac ggcacctcga ccccaaaaaa cttgattagg gtgatggttc   1380
acgtagtggg ccatcgccct gatagacggt ttttcgccct ttgacgttgg agtccacgtt   1440
ctttaatagt ggactcttgt tccaaactgg aacaacactc aaccctatct cggtctattc   1500
ttttgattta tagggatttt tgccgatttc ggcctattgg ttaaaaaatg agctgattta   1560
acaaaaattt aacgcgaatt ttaacaaaat attaacgctt acaatttagg tggcacttttt   1620
cggggaaatg tgcgcggaac ccctatttgt ttatttttct aaatacattc aaatatgtat   1680
ccgctcatga caataaacc ctgataaatg cttcaataat attgaaaaag gaagagtatg   1740
agtattcaac atttccgtgt cgcccttatt ccctttttg cggcattttg ccttcctgtt   1800
tttgctcacc cagaaacgct ggtgaaagta aaagatgctg aagatcagtt gggtgcacga   1860
gtgggttaca tcgaactgga tctcaacagc ggtaagatcc ttgagagttt tcgccccgaa   1920
gaacgttttc caatgatgag cacttttaaa gttctgctat gtggcgcggt attatcccgt   1980
attgacgccg ggcaagagca actcggtcgc cgcatacact attctcagaa tgacttggtt   2040
gagtactcac cagtcacaga aaagcatctt acggatggca tgacagtaag agaattatgc   2100
agtgctgcca taaccatgag tgataacact gcggccaact tacttctgac aacgatcgga   2160
ggaccgaagg agctaaccgc ttttttgcac aacatggggg atcatgtaac tcgccttgat   2220
cgttgggaac cggagctgaa tgaagccata ccaaacgacg agcgtgacac cacgatgcct   2280
gtagcaatgg caacaacgtt gcgcaaacta ttaactggcg aactacttac tctagcttcc   2340
cggcaacaat taatagactg gatggaggcg gataaagttg caggaccact tctgcgctcg   2400
gcccttccgg ctggctggtt tattgctgat aaatctggag ccggtgagcg tgggtctcgc   2460
ggtatcattg cagcactggg gccagatggt aagccctccc gtatcgtagt tatctacacg   2520
acggggagtc aggcaactat ggatgaacga atagacaga tcgctgagat aggtgcctca   2580
ctgattaagc attggtaact gtcagaccaa gtttactcat atatacttta gattgattta   2640
aaacttcatt tttaatttaa aaggatctag gtgaagatcc ttttttgataa tctcatgacc   2700
aaaatccctt aacgtgagtt ttcgttccac tgagcgtcag accccgtaga aaagatcaaa   2760
ggatcttctt gagatccttt ttttctgcgc gtaatctgct gcttgcaaac aaaaaaacca   2820
ccgctaccag cggtggtttg tttgccggat caagagctac caactctttt tccgaaggta   2880
actggcttca gcagagcgca gataccaaat actgtccttc tagtgtagcc gtagttaggc   2940
caccacttca agaactctgt agcaccgcct acatacctcg ctctgctaat cctgttacca   3000
gtggctgctg ccagtggcga taagtcgtgt cttaccgggt tggactcaag acgatagtta   3060
ccggataagg cgcagcggtc gggctgaacg gggggttcgt gcacacagcc cagcttggag   3120
```

-continued

```
cgaacgacct acaccgaact gagataccta cagcgtgagc tatgagaaag cgccacgctt    3180
cccgaaggga gaaaggcgga caggtatccg gtaagcggca gggtcggaac aggagagcgc    3240
acgagggagc ttccaggggg aaacgcctgg tatctttata gtcctgtcgg gtttcgccac    3300
ctctgacttg agcgtcgatt tttgtgatgc tcgtcagggg ggcggagcct atggaaaaac    3360
gccagcaacg cggcctttt acggttcctg ccttttgct ggccttttgc tcacatgttc     3420
tttcctgcgt tatcccctga ttctgtggat aaccgtatta ccgcctttga gtgagctgat   3480
accgctcgcc gcagccgaac gaccgagcgc agcgagtcag tgagcgagga agc          3533
```

<210> SEQ ID NO 28
<211> LENGTH: 4323
<212> TYPE: DNA
<213> ORGANISM: Artificial Sequence
<220> FEATURE:
<223> OTHER INFORMATION: Description of Artificial Sequence:Vector

<400> SEQUENCE: 28

```
aacctggctt atcgaaatta atacgactca ctatagggag accggcagat ctgatatcac      60
aagtttgtac aaaaaagcag gctcaaatcg gtgttggagc atccggaact gtattcgttg    120
ctaatgtggc cggcagcact gatgtggtgg ctgtgaagag aatggctttc aagactcagc    180
cgaagaagga gatgttgctc accgagatta aggttatgaa gcagtatcga cacccgaacc    240
tcgtcaacta cattgaatcg tatctggttg atgctgatga tctttgggta gtgatggatt    300
atctggaagg tggaaacttg acagatgtcg ttgtgaagac tgagttggac gaaggacaaa    360
ttgcagcagt tttgcaagaa tgtcttaaag cgcttcactt ccttcataga cactccatag    420
tgcaccgaga tatcaagagt gacaacgtgc tgctcggcat gaacggagag gttaagctca    480
ccgatatggg attctgtgct cagattcagc cgggatcgaa aagagatact gtcgtcggaa    540
ctccatattg gatgtcgccg gagatattga acaagaagca gtacaactat aaggttgaca    600
tttggtcgct gggaattatg gctctagaga tgattgatgg agagccacca tatttgagag    660
aaacaccttt gaaggctatc tacttgattg ctcaaaacgg gaagccagag atcaagcaac    720
gcgacagact gtcttcagag ttcaacaatt tccttgacaa gtgtcttgtt gttgatccgg    780
atcagagagc cgatacaacg gagctcttgg cacatccatt cctgaaaaag gcgaagccac    840
tctcaagcct gattccatac atcagagccg tccgagaaaa gtagcaccgc tattgaaatt    900
agtaccgaag cggaggtggc tatcaagcag atgaacctga aggatcaacc aaagaaggaa    960
ttgatcatta atgagatttt ggtgatgcgt gagaataagc atgcaaatat tgtaaattat   1020
ttggattcgt atttggtgtg cgatgaatta tgggtagtga tggagtatct tgccggtgga   1080
tcattgactg atgttgtcac ggagtgccag atggaggatg gaattattgc agctgtttgc   1140
agagaagttc ttcaagcgct tgaattcctc cacagccgcc acgtcattca cagagatatt   1200
aaatctgaca atattcttt gggaatggat ggttcggtga aattgaccga ctttggattc    1260
tgtgctcagc tctcgccgga gcaaagaaaa cgcacgacaa tggtcggaac tccatactgg   1320
atggcgccgg aagtggtgac ccgcaaacaa tacggaccca aggttgatgt gtggtccttg   1380
ggaatcatgg cgattgagat ggtcgaagga gaaccgccat atttgaatga aaatccactc   1440
agggctatct atctcattgc tacaaatggc aaacccgact tccctggaag agattccatg   1500
actttgttgt tcaaggactt tgtcgactct gcgttggaag tacaagttga aaatcgatgg   1560
tcggcaagcc aactccttac gcatccattc ctccgatgcg ccaaaccgct tgcttcactg   1620
tactacttaa tcgttgcggc gaagaagagc atcgccgaag ctagcaactc ataaacccag   1680
```

-continued

```
ctttcttgta caaagtggtg atatcaagct tatcgatacc gtcgacctcg agggggggcc      1740
cggtacccaa ttcgccctat agtgagtcgt attacgcgcg ctcactggcc gtcgttttac      1800
aacgtcgtga ctgggaaaac cctggcgtta cccaacttaa tcgccttgca gcacatcccc      1860
ctttcgccag ctggcgtaat agcgaagagg cccgcaccga tcgcccttcc caacagttgc      1920
gcagcctgaa tggcgaatgg gacgcgcccg tagcggcgc attaagcgcg gcgggtgtgg       1980
tggttacgcg cagcgtgacc gctacacttg ccagcgccct agcgcccgct cctttcgctt      2040
tcttcccttc ctttctcgcc acgttcgccg gctttcccccg tcaagctcta atcgggggc      2100
tcccctttagg gttccgattt agtgctttac ggcacctcga ccccaaaaaa cttgattagg     2160
gtgatggttc acgtagtggg ccatcgccct gatagacggt ttttcgccct ttgacgttgg      2220
agtccacgtt ctttaatagt ggactcttgt tccaaactgg aacaacactc aaccctatct     2280
cggtctattc ttttgattta taagggattt tgccgatttc ggcctattgg ttaaaaaatg     2340
agctgattta acaaaaattt aacgcgaatt ttaacaaaat attaacgctt acaatttagg      2400
tggcactttt cggggaaatg tgcgcggaac ccctatttgt ttatttttct aaatacattc     2460
aaatatgtat ccgctcatga acaataaacc ctgataaatg cttcaataat attgaaaaag     2520
gaagagtatg agtattcaac atttccgtgt cgcccttatt cccttttttg cggcattttg     2580
ccttcctgtt tttgctcacc cagaaacgct ggtgaaagta aaagatgctg aagatcagtt     2640
gggtgcacga gtgggttaca tcgaactgga tctcaacagc ggtaagatcc ttgagagttt     2700
tcgccccgaa gaacgttttc caatgatgag cacttttaaa gttctgctat gtggcgcggt    2760
attatcccgt attgacgccg ggcaagagca actcggtcgc cgcatacact attctcagaa     2820
tgacttggtt gagtactcac cagtcacaga aaagcatctt acggatgggca tgacagtaag   2880
agaattatgc agtgctgcca taaccatgag tgataacact gcggccaact tacttctgac   2940
aacgatcgga ggaccgaagg agctaaccgc ttttttgcac aacatggggg atcatgtaac   3000
tcgccttgat cgttgggaac cggagctgaa tgaagccata ccaaacgacg agcgtgacac    3060
cacgatgcct gtagcaatgg caacaacgtt gcgcaaacta ttaactggcg aactacttac   3120
tctagcttcc cggcaacaat aatagactg gatggaggcg gataaagttg caggaccact    3180
tctgcgctcg gcccttccgg ctggctggtt tattgctgat aaatctggag ccggtgagcg   3240
tgggtctcgc ggtatcattg cagcactggg gccagatggt aagccctccc gtatcgtagt   3300
tatctacacg acggggagtc aggcaactat ggatgaacga atagacaga tcgctgagat   3360
aggtgcctca ctgattaagc attggtaact gtcagaccaa gtttactcat atatacttta   3420
gattgattta aaacttcatt tttaatttaa aaggatctag gtgaagatcc ttttgataa    3480
tctcatgacc aaaatccctt aacgtgagtt ttcgttccac tgagcgtcag accccgtaga   3540
aaagatcaaa ggatcttctt gagatccttt tttttctgcgc gtaatctgct gcttgcaaac   3600
aaaaaaacca ccgctaccag cggtggtttg tttgccggat caagagctac caactctttt   3660
tccgaaggta actggcttca gcagagcgca gataccaaat actgtccttc tagtgtagcc   3720
gtagttaggc caccacttca agaactctgt agcaccgcct acatacctcg ctctgctaat   3780
cctgttacca gtggctgctg ccagtggcga taagtcgtgt cttaccgggt tggactcaag    3840
acgatagtta ccggataagg cgcagcggtc gggctgaacg ggggggttcgt gcacacagcc   3900
cagcttggag cgaacgacct acaccgaact gagataccta cagcgtgagc tatgagaaag    3960
cgccacgctt cccgaaggga gaaaggcgga caggtatccg gtaagcggca gggtcggaac    4020
```

| | |
|---|---|
| aggagagcgc acgagggagc ttccaggggg aaacgcctgg tatctttata gtcctgtcgg | 4080 |
| gtttcgccac ctctgacttg agcgtcgatt tttgtgatgc tcgtcagggg ggcggagcct | 4140 |
| atggaaaaac gccagcaacg cggccttttt acggttcctg ccttttgct ggccttttgc | 4200 |
| tcacatgttc tttcctgcgt tatcccctga ttctgtggat aaccgtatta ccgcctttga | 4260 |
| gtgagctgat accgctcgcc gcagccgaac gaccgagcgc agcgagtcag tgagcgagga | 4320 |
| agc | 4323 |

<210> SEQ ID NO 29
<211> LENGTH: 2865
<212> TYPE: DNA
<213> ORGANISM: Artificial Sequence
<220> FEATURE:
<223> OTHER INFORMATION: Description of Artificial Sequence:Vector

<400> SEQUENCE: 29

| | |
|---|---|
| aacctggctt atcgaaatta atacgactca ctatagggag accggcagat ctgatatcac | 60 |
| aagtttgtac aaaaaagcag gctcaaaaat gtttcaaaat agtccgatga tgtacgactg | 120 |
| gtggaatgac accaccaaac cgaaacacca gcagccgaca cttaacgtgt tgtcaccatg | 180 |
| gggagcatat ttcaatcaca ttggaaatga actgctaccc agctttcttg tacaaagtgg | 240 |
| tgatatcaag cttatcgata ccgtcgacct cgagggggg cccggtaccc aattcgccct | 300 |
| atagtgagtc gtattacgcg cgctcactgg ccgtcgtttt acaacgtcgt gactgggaaa | 360 |
| accctggcgt tacccaactt aatcgccttg cagcacatcc ccctttcgcc agctggcgta | 420 |
| atagcgaaga ggcccgcacc gatcgccctt cccaacagtt gcgcagcctg aatggcgaat | 480 |
| gggacgcgcc ctgtagcggc gcattaagcg cggcgggtgt ggtggttacg cgcagcgtga | 540 |
| ccgctacact tgccagcgcc ctagcgcccg ctcctttcgc tttcttccct cctttctcg | 600 |
| ccacgttcgc cggctttccc cgtcaagctc taaatcgggg gctcccttta gggttccgat | 660 |
| ttagtgcttt acggcacctc gaccccaaaa aacttgatta gggtgatggt tcacgtagtg | 720 |
| ggccatcgcc ctgatagacg ttttttcgcc ctttgacgtt ggagtccacg ttctttaata | 780 |
| gtggactctt gttccaaact ggaacaacac tcaaccctat ctcggtctat tcttttgatt | 840 |
| tataagggat tttgccgatt tcggcctatt ggttaaaaaa tgagctgatt taacaaaaat | 900 |
| ttaacgcgaa ttttaacaaa atattaacgc ttacaattta ggtggcactt ttcggggaaa | 960 |
| tgtgcgcgga acccctattt gtttattttt ctaaatacat tcaaatatgt atccgctcat | 1020 |
| gagacaataa ccctgataaa tgcttcaata atattgaaaa aggaagagta tgagtattca | 1080 |
| acatttccgt gtcgccctta ttcccttttt tgcggcattt tgccttcctg tttttgctca | 1140 |
| cccagaaacg ctggtgaaag taaaagatgc tgaagatcag ttgggtgcac gagtgggtta | 1200 |
| catcgaactg gatctcaaca gcggtaagat ccttgagagt tttcgccccg aagaacgttt | 1260 |
| tccaatgatg agcactttta aagttctgct atgtggcgcg gtattatccc gtattgacgc | 1320 |
| cgggcaagag caactcggtc gccgcataca ctattctcag aatgacttgg ttgagtactc | 1380 |
| accagtcaca gaaaagcatc ttacggatgg catgacagta agagaattat gcagtgctgc | 1440 |
| cataaccatg agtgataaca ctgcggccaa cttacttctg acaacgatcg gaggaccgaa | 1500 |
| ggagctaacc gcttttttgc acaacatggg ggatcatgta actcgccttg atcgttggga | 1560 |
| accggagctg aatgaagcca taccaaacga cgagcgtgac accacgatgc ctgtagcaat | 1620 |
| ggcaacaacg ttgcgcaaac tattaactgg cgaactactt actctagctt cccggcaaca | 1680 |
| attaatagac tggatggagg cggataaagt tgcaggacca cttctgcgct cggcccttcc | 1740 |

-continued

```
ggctggctgg tttattgctg ataaatctgg agccggtgag cgtgggtctc gcggtatcat    1800
tgcagcactg gggccagatg gtaagccctc ccgtatcgta gttatctaca cgacggggag    1860
tcaggcaact atgatgaac gaaatagaca gatcgctgag ataggtgcct cactgattaa    1920
gcattggtaa ctgtcagacc aagtttactc atatatactt tagattgatt taaaacttca    1980
tttttaattt aaaaggatct aggtgaagat cctttttgat aatctcatga ccaaaatccc    2040
ttaacgtgag ttttcgttcc actgagcgtc agaccccgta gaaaagatca aaggatcttc    2100
ttgagatcct ttttttctgc gcgtaatctg ctgcttgcaa acaaaaaaac caccgctacc    2160
agcggtggtt tgtttgccgg atcaagagct accaactctt tttccgaagg taactggctt    2220
cagcagagcg cagataccaa atactgtcct tctagtgtag ccgtagttag gccaccactt    2280
caagaactct gtagcaccgc ctacatacct cgctctgcta atcctgttac cagtggctgc    2340
tgccagtggc gataagtcgt gtcttaccgg gttggactca agacgatagt taccggataa    2400
ggcgcagcgg tcgggctgaa cggggggttc gtgcacacag cccagcttgg agcgaacgac    2460
ctacaccgaa ctgagatacc tacagcgtga gctatgagaa agcgccacgc ttcccgaagg    2520
gagaaaggcg gacaggtatc cggtaagcgg cagggtcgga acaggagagc gcacgaggga    2580
gcttccaggg ggaaacgcct ggtatcttta tagtcctgtc gggtttcgcc acctctgact    2640
tgagcgtcga tttttgtgat gctcgtcagg gggcggagc ctatgaaaaa cgccagcaa    2700 cgcggccttt ttacggttcc tggccttttg ctggccttt gctcacatgt tctttcctgc    2760
gttatcccct gattctgtgg ataaccgtat taccgccttt gagtgagctg ataccgctcg    2820
ccgcagccga cgaccgagc gcagcgagtc agtgagcgag gaagc                    2865
```

<210> SEQ ID NO 30
<211> LENGTH: 3525
<212> TYPE: DNA
<213> ORGANISM: Artificial Sequence
<220> FEATURE:
<223> OTHER INFORMATION: Description of Artificial Sequence:Vector

<400> SEQUENCE: 30

```
aacctggctt atcgaaatta atacgactca ctatagggag accggcagat ctgatatcac     60
aagtttgtac aaaaaagcag gctcaaaaat gtcaacttca aaaagttcca aggtgcgaat    120
acggaatttc atcgggcgaa tcttctctcc cagcgataaa gacaaggatc gagacgatga    180
gatgaagcca tcctcgtccg caatggatat tagtcagcca tataacacag tgcatcgagt    240
ccacgttgga tacgacggcc agaagttcag cggactgccg caaccatgga tggatattct    300
tctccgagac attagtcttg ccgatcagaa gaaggatccg aacgcggtgg tgactgcgtt    360
gaagttctac gcacaatcaa tgaaggagaa cgagaagacg aaattcatga cgacgaatag    420
tgttttcacg aatagcgatg acgatgatgt ggacgttcag ttgaccggac aagtcacgga    480
acatttgagg aatttgcagt gtagtaatgg ttccgcaact tccccatcta catcagtgtc    540
agcttcatct tcttctgctc gtccactgac aaatggaaat aatcatcttt ccacggcgtc    600
gtctaccgac acatctctct cattatcgga aaggaataac gttccgtctc cagctccagt    660
tccatatagt gaaagtgctc cacaactgaa acattcacc ggagagactc caaaactgca    720
tccacgatct ccgttcccgc ctcaaccgcc agttcttccg caacgaagca aaaccgcatc    780
ggcagtggcg acgacgacga cgaatccgac gacttcgaat ggagcaccac caccagttcc    840
tggatcgaaa ggaccccgg tgccaccgaa accatcaccc agctttcttg tacaaagtgg    900
```

```
tgatatcaag cttatcgata ccgtcgacct cgagggggggg cccggtaccc aattcgccct    960
atagtgagtc gtattacgcg cgctcactgg ccgtcgtttt acaacgtcgt gactgggaaa   1020
accctggcgt tacccaactt aatcgccttg cagcacatcc ccctttcgcc agctggcgta   1080
atagcgaaga ggcccgcacc gatcgccctt cccaacagtt gcgcagcctg aatggcgaat   1140
gggacgcgcc ctgtagcggc gcattaagcg cggcgggtgt ggtggttacg cgcagcgtga   1200
ccgctacact tgccagcgcc ctagcgcccg ctcctttcgc tttcttccct cctttctcg    1260
ccacgttcgc cggctttccc cgtcaagctc taaatcgggg gctcccttta gggttccgat   1320
ttagtgcttt acggcacctc gaccccaaaa aacttgatta gggtgatggt tcacgtagtg   1380
ggccatcgcc ctgatagacg gttttttcgcc ctttgacgtt ggagtccacg ttctttaata  1440
gtggactctt gttccaaact ggaacaacac tcaaccctat ctcggtctat tcttttgatt   1500
tataagggat tttgccgatt tcggcctatt ggttaaaaaa tgagctgatt taacaaaaat   1560
ttaacgcgaa ttttaacaaa atattaacgc ttacaattta ggtggcactt ttcggggaaa   1620
tgtgcgcgga acccctattt gtttattttt ctaaatacat tcaaatatgt atccgctcat   1680
gagacaataa ccctgataaa tgcttcaata atattgaaaa aggaagagta tgagtattca   1740
acatttccgt gtcgccctta ttcccttttt tgcggcattt tgccttcctg tttttgctca   1800
cccagaaacg ctggtgaaag taaaagatgc tgaagatcag ttgggtgcac gagtgggtta   1860
catcgaactg gatctcaaca gcggtaagat ccttgagagt tttcgccccg aagaacgttt   1920
tccaatgatg agcacttttaa aagttctgct atgtggcgcg gtattatccc gtattgacgc   1980
cgggcaagag caactcggtc gccgcataca ctattctcag aatgacttgg ttgagtactc   2040
accagtcaca gaaaagcatc ttacggatgg catgacagta agagaattat gcagtgctgc   2100
cataaccatg agtgataaca ctgcggccaa cttacttctg acaacgatcg gaggaccgaa   2160
ggagctaacc gcttttttgc acaacatggg ggatcatgta actcgccttg atcgttggga   2220
accggagctg aatgaagcca taccaaacga cgagcgtgac accacgatgc ctgtagcaat   2280
ggcaacaact ttgcgcaaac tattaactgg cgaactactt actctagctt cccggcaaca   2340
attaatagac tggatggagg cggataaagt tgcaggacca cttctgcgct cggcccttcc   2400
ggctggctgg tttattgctg ataaatctgg agccggtgag cgtgggtctc gcggtatcat   2460
tgcagcactg gggccagatg gtaagccctc ccgtatcgta gttatctaca cgacggggag   2520
tcaggcaact atggatgaac gaaatagaca gatcgctgag ataggtgcct cactgattaa   2580
gcattggtaa ctgtcagacc aagtttactc atatatactt tagattgatt taaaacttca   2640
tttttaattt aaaaggatct aggtgaagat ccttttttgat aatctcatga ccaaaatccc   2700
ttaacgtgag ttttcgttcc actgagcgtc agaccccgta gaaaagatca aaggatcttc   2760
ttgagatcct ttttttctgc gcgtaatctg ctgcttgcaa acaaaaaaac caccgctacc   2820
agcggtggtt tgtttgccgg atcaagagct accaactctt tttccgaagg taactggctt   2880
cagcagagcg cagataccaa atactgtcct tctagtgtag ccgtagttag gccaccactt   2940
caagaactct gtagcaccgc ctacatacct cgctctgcta atcctgttac cagtggctgc   3000
tgccagtggc gataagtcgt gtcttaccgg gttggactca agacgatagt taccggataa   3060
ggcgcagcgg tcgggctgaa cggggggttc gtgcacacag cccagcttgg agcgaacgac   3120
ctacaccgaa ctgagatacc tacagcgtga gctatgagaa agcgccacgc ttcccgaagg   3180
gagaaaggcg gacaggtatc cggtaagcgg cagggtcgga acaggagagc gcacgaggga   3240
gcttccaggg ggaaacgcct ggtatcttta tagtcctgtc gggtttcgcc acctctgact   3300
```

```
tgagcgtcga ttttttgtgat gctcgtcagg ggggcggagc ctatggaaaa acgccagcaa    3360
cgcggccttt ttacggttcc tggccttttg ctggccttttt gctcacatgt tctttcctgc    3420
gttatcccct gattctgtgg ataaccgtat taccgccttt gagtgagctg ataccgctcg    3480
ccgcagccga acgaccgagc gcagcgagtc agtgagcgag gaagc                    3525
```

<210> SEQ ID NO 31
<211> LENGTH: 3292
<212> TYPE: DNA
<213> ORGANISM: Artificial Sequence
<220> FEATURE:
<223> OTHER INFORMATION: Description of Artificial Sequence:Vector

<400> SEQUENCE: 31

```
aacctggctt atcgaaatta atacgactca ctatagggag accggcagat ctgatatcat      60
cgatgaattc gagctccacc gcggtggcgg ccgctctaga actagtggat ccccccgggct    120 gcaggaattc gcccgtcgg taaaacgtgt ctcctgatat cctacaccac aaacgcattt     180 cccgagaat atattccgac ggtattcgac aactactcag caaatgtgat ggtcgacgt       240 cggccgataa atctcgggct ctgggataca gctggacagg aagattacga tcgactccga    300
ccactgtcat atccacaaac agacgtgttt ctcgtatgct ttgccctgaa caatccggcg    360
agttttgaga atgttcgtgc gaaatggtat ccagaagtgt cacatcattg cccgaatacg    420
ccgattattt tggttggaac gaaagctgat ctgcgtgagg atcgagatac tgttgaacgg    480
ctccgcgaac gccggctcca accagtgagc caaacccagg gctacgtgat ggcaaaggaa    540
atcaaggctg tcaagtatct ggagtgctcg gcgctcacgc aacgtggtct gaaacaagtt    600
ttcgatgagg cgatccgagc cgtgctcacg ccgccacaaa gagccaaaaa gagcaagtgg    660
gcgaattcga tatcaagctt atcgataccg tcgacctcga ggggggggccc ggtacccaat    720 tcgccctata gtgagtcgta ttacgcgcgc tcactggccg tcgttttaca acgtcgtgac    780
tgggaaaacc ctggcgttac ccaacttaat cgccttgcag cacatccccc tttcgccagc    840
tggcgtaata gcgaagaggc ccgcaccgat cgccttccc aacagttgcg cagcctgaat    900
ggcgaatggg acgcgccctg tagcggcgca ttaagcgcgg cgggtgtggt ggttacgcgc    960
agcgtgaccg ctacacttgc cagcgcccta gcgcccgctc ctttcgcttt cttcccttcc   1020
tttctcgcca cgttcgccgg ctttccccgt caagctctaa atcgggggct cccttaggg   1080 ttccgattta gtgctttacg gcacctcgac cccaaaaaac ttgattaggg tgatggttca   1140
cgtagtgggc catcgccctg atagacggtt tttcgccctt tgacgttgga gtccacgttc   1200
tttaatagtg gactcttgtt ccaaactgga acaacactca accctatctc ggtctattct   1260
tttgatttat aagggatttt gccgatttcg gcctattggt taaaaaatga gctgatttaa   1320
caaaaattta acgcgaattt taacaaaata ttaacgctta catttaggt ggcacttttc    1380 ggggaaatgt gcgcggaacc cctatttgtt tatttttcta aatacattca aatatgtatc   1440
cgctcatgag acaataaccc tgataaatgc ttcaataata ttgaaaaagg aagagtatga   1500
gtattcaaca tttccgtgtc gcccttattc ccttttttgc ggcattttgc cttcctgttt   1560
ttgctcaccc agaaacgctg gtgaaagtaa aagatgctga agatcagttg ggtgcacgag   1620
tgggttacat cgaactggat ctcaacagcg gtaagatcct tgagagtttt cgccccgaag   1680
aacgttttcc aatgatgagc acttttaaag ttctgctatg tggcgcggta ttatcccgta   1740
ttgacgccgg gcaagagcaa ctcggtcgcc gcatacacta ttctcagaat gacttggttg   1800
```

```
agtactcacc agtcacagaa aagcatctta cggatggcat gacagtaaga gaattatgca    1860
gtgctgccat aaccatgagt gataacactg cggccaactt acttctgaca acgatcggag    1920
gaccgaagga gctaaccgct tttttgcaca acatggggga tcatgtaact cgccttgatc    1980
gttgggaacc ggagctgaat gaagccatac caaacgacga gcgtgacacc acgatgcctg    2040
tagcaatggc aacaacgttg cgcaaactat taactggcga actacttact ctagcttccc    2100
ggcaacaatt aatagactgg atggaggcgg ataaagttgc aggaccactt ctgcgctcgg    2160
cccttccggc tggctggttt attgctgata atctggagc cggtgagcgt gggtctcgcg     2220
gtatcattgc agcactgggg ccagatggta agccctcccg tatcgtagtt atctacacga    2280
cggggagtca ggcaactatg gatgaacgaa atagacagat cgctgagata ggtgcctcac    2340
tgattaagca ttggtaactg tcagaccaag tttactcata tatactttag attgatttaa    2400
aacttcattt ttaatttaaa aggatctagg tgaagatcct ttttgataat ctcatgacca    2460
aaatccctta acgtgagttt tcgttccact gagcgtcaga ccccgtagaa aagatcaaag    2520
gatcttcttg agatcctttt tttctgcgcg taatctgctg cttgcaaaca aaaaaaccac    2580
cgctaccagc ggtggtttgt ttgccggatc aagagctacc aactcttttt ccgaaggtaa    2640
ctggcttcag cagagcgcag ataccaaata ctgtccttct agtgtagccg tagttaggcc    2700
accacttcaa gaactctgta gcaccgccta catacctcgc tctgctaatc ctgttaccag    2760
tggctgctgc cagtggcgat aagtcgtgtc ttaccgggtt ggactcaaga cgatagttac    2820
cggataaggc gcagcggtcg ggctgaacgg ggggttcgtg cacacagccc agcttggagc    2880
gaacgaccta caccgaactg agatacctac agcgtgagct atgagaaagc gccacgcttc    2940
ccgaagggag aaaggcggac aggtatccgg taagcggcag ggtcggaaca ggagagcgca    3000
cgagggagct tccaggggga aacgcctggt atctttatag tcctgtcggg tttcgccacc    3060
tctgacttga gcgtcgattt ttgtgatgct cgtcaggggg gcggagccta tggaaaaacg    3120
ccagcaacgc ggccttttta cggttcctgg ccttttgctg gccttttgct cacatgttct    3180
ttcctgcgtt atcccctgat tctgtggata accgtattac cgcctttgag tgagctgata    3240
ccgctcgccg cagccgaacg accgagcgca gcgagtcagt gagcgaggaa gc            3292
```

<210> SEQ ID NO 32
<211> LENGTH: 3323
<212> TYPE: DNA
<213> ORGANISM: Artificial Sequence
<220> FEATURE:
<223> OTHER INFORMATION: Description of Artificial Sequence:Vector

<400> SEQUENCE: 32

```
aacctggctt atcgaaatta atacgactca ctatagggag accggcagat ctgatatcat      60
cgatgaattc gagctccacc gcggtggcgg ccgctctaga actagtggat cccccgggct     120
gcaggaattc cgcccctcgag gcagatcaaa tgtgtagttg ttggagacgg aacagttgga    180
aaaacatgca tgttaatatc ttacacaact gactcttttc cagttcagta tgtgcctaca    240
gtatttgata actattcggc acagatgagt cttgatggga acgttgtgaa cttaggattg    300
tgggatactg ctggacagga ggattatgat cgtttacgac cactttccta cccacagacg    360
gatgttttca ttctctgctt ctctgtcgtc tcgcccgtat cgtttgacaa tgtggcaagc    420
aagtggattc cggaaatacg acagcattgt ccagatgcgc ctgtcattct agttggtacc    480
aaactcgatt tgcgcgacga ggccgaaccg atgcgtgctc tgcaggccga aggaaagtcc    540
ccaatttcca aaacgcaagg catgaaaatg gctcaaaaaa ttaaagctgt caagtatttg    600
```

```
gaatgctctg cattgacgca acagggactc acacaggtgt tcgaagacgc cgtacggtcc    660
attcttcatc cgaaaccaca gaaaagaag  ggcgaattcg atatcaagct tatcgatacc    720
gtcgacctcg aggggggggcc cggtacccaa ttcgccctat agtgagtcgt attacgcgcg   780
ctcactggcc gtcgttttac aacgtcgtga ctgggaaaac cctggcgtta cccaacttaa   840
tcgccttgca gcacatcccc ctttcgccag ctggcgtaat agcgaagagg cccgcaccga   900
tcgcccttcc caacagttgc gcagcctgaa tggcgaatgg gacgcgccct gtagcggcgc   960
attaagcgcg gcgggtgtgg tggttacgcg cagcgtgacc gctacacttg ccagcgccct  1020
agcgcccgct cctttcgctt tcttcccttc ctttctcgcc acgttcgccg gctttccccg  1080
tcaagctcta atcgggggc tcccttagg gttccgattt agtgctttac ggcacctcga   1140
ccccaaaaaa cttgattagg gtgatggttc acgtagtggg ccatcgccct gatagacggt  1200
ttttcgccct ttgacgttgg agtccacgtt ctttaatagt ggactcttgt tccaaactgg  1260
aacaacactc aaccctatct cggtctattc ttttgattta agggatttt  tgccgatttc   1320 ggcctattgg ttaaaaaatg agctgattta caaaaattt  aacgcgaatt ttaacaaaat   1380
attaacgctt acaatttagg tggcacttt  cggggaaatg tgcgcggaac ccctatttgt   1440
ttatttttct aaatacattc aaatatgtat ccgctcatga caataaacc  ctgataaatg   1500 cttcaataat attgaaaaag gaagagtatg agtattcaac atttccgtgt cgcccttatt   1560 ccctttttg  cggcattttg ccttcctgtt tttgctcacc cagaaacgct ggtgaaagta   1620
aaagatgctg aagatcagtt gggtgcacga gtgggttaca tcgaactgga tctcaacagc   1680
ggtaagatcc ttgagagttt tcgccccgaa gaacgttttc caatgatgag cacttttaaa   1740
gttctgctat gtggcgcggt attatcccgt attgacgccg ggcaagagca actcggtcgc   1800
cgcatacact attctcagaa tgacttggtt gagtactcac cagtcacaga aaagcatctt   1860
acggatggca tgacagtaag agaattatgc agtgctgcca taaccatgag tgataacact   1920
gcggccaact tacttctgac aacgatcgga ggaccgaagg agctaaccgc ttttttgcac   1980
aacatggggg atcatgtaac tcgccttgat cgttgggaac cggagctgaa tgaagccata   2040
ccaaacgacg agcgtgacac cacgatgcct gtagcaatgg caacaacgtt gcgcaaacta   2100
ttaactggcg aactacttac tctagcttcc cggcaacaat taatagactg gatggaggcg   2160
gataaagttg caggaccact tctgcgctcg gcccttccgg ctggctggtt tattgctgat   2220
aaatctggag ccggtgagcg tgggtctcgc ggtatcattg cagcactggg gccagatggt   2280
aagccctccc gtatcgtagt tatctacacg acggggagtc aggcaactat ggatgaacga   2340
aatagacaga tcgctgagat aggtgcctca ctgattaagc attggtaact gtcagaccaa   2400
gtttactcat atatacttta gattgattta aaacttcatt tttaatttaa aaggatctag   2460
gtgaagatcc tttttgataa tctcatgacc aaaatccctt aacgtgagtt ttcgttccac   2520
tgagcgtcag accccgtaga aaagatcaaa ggatcttctt gagatccttt ttttctgcgc   2580
gtaatctgct gcttgcaaac aaaaaaacca ccgctaccag cggtggtttg tttgccggat   2640
caagagctac caactctttt tccgaaggta actggcttca gcagagcgca gataccaaat   2700
actgtccttc tagtgtagcc gtagttaggc caccacttca agaactctgt agcaccgcct   2760
acatacctcg ctctgctaat cctgttacca gtggctgctg ccagtggcga taagtcgtgt   2820
cttaccgggt tggactcaag acgatagtta ccggataagg cgcagcggtc gggctgaacg   2880
gggggttcgt gcacacagcc cagcttggag cgaacgacct acaccgaact gagataccta   2940
```

```
cagcgtgagc tatgagaaag cgccacgctt cccgaaggga gaaaggcgga caggtatccg    3000
gtaagcggca gggtcggaac aggagagcgc acgagggagc ttccaggggg aaacgcctgg    3060
tatctttata gtcctgtcgg gtttcgccac ctctgacttg agcgtcgatt tttgtgatgc    3120
tcgtcagggg ggcggagcct atggaaaaac gccagcaacg cggcctttt acggttcctg     3180 gccttttgct ggccttttgc tcacatgttc tttcctgcgt tatcccctga ttctgtggat    3240
aaccgtatta ccgcctttga gtgagctgat accgctcgcc gcagccgaac gaccgagcgc    3300
agcgagtcag tgagcgagga agc                                            3323

<210> SEQ ID NO 33
<211> LENGTH: 1281
<212> TYPE: DNA
<213> ORGANISM: Caenorhabditis elegans

<400> SEQUENCE: 33
atgtttcaaa atagtccgat gatgtacgac tggtggaatg acaccaccaa accgaaacac     60
cagcagccga cacttaacgt gttgtcacca tggggagcat atttcaatca cattggaaat    120
gaactgctgc atctgaaaat cgcatcgtcg acagtatcct cgggatgctc gtctccacaa    180
cagtattcgt ctgctcgatc cgttggtaac tcgctctcca acggcagtgt tgtctccaca    240
acatcgtcag atggtgatgt gcaattgtcg aataaggaaa attcgaatga caaatcagtt    300
ggagacaaga atgggaacac caccacaaac aaaacgaccg tcgaaccacc tccaccagaa    360
gagccacctg ttcgtgttcg agcatctcat cgtgaaaagc tttctgattc cgaagtgctc    420
aatcaactcc gcgagattgt taatccaagt aatccacttg gaaagtacga gatgaagaag    480
caaatcggtg ttggagcatc cggaactgta ttcgttgcta atgtggccgg cagcactgat    540
gtggtggctg tgaagagaat ggctttcaag actcagccga agaaggagat gttgctcacc    600
gagattaagg ttatgaagca gtatcgacac ccgaacctcg tcaactacat tgaatcgtat    660
ctggttgatg ctgatgatct ttgggtagtg atggattatc tggaaggtgg aaacttgaca    720
gatgtcgttg tgaagactga gttggacgaa ggacaaattg cagcagtttt gcaagaatgt    780
cttaaagcgc ttcacttcct tcatagacac tccatagtgc accgagatat caagagtgac    840
aacgtgctgc tcggcatgaa cggagaggtt aagctcaccg atatgggatt ctgtgctcag    900
attcagccgg gatcgaaaag agatactgtc gtcggaactc catattggat gtcgccggag    960
atattgaaca gaagcagta caactataag gttgacattt ggtcgctggg aattatggct    1020
ctagagatga ttgatggaga gccaccatat ttgagagaaa cacctttgaa ggctatctac    1080
ttgattgctc aaaacgggaa gccagagatc aagcaacgcg acagactgtc ttcagagttc    1140
aacaatttcc ttgacaagtg tcttgttgtt gatccggatc agagagccga tacaacggag    1200
ctcttggcac atccattcct gaaaaaggcg aagccactct caagcctgat tccatacatc    1260
agagccgtcc gagaaaagta g                                              1281

<210> SEQ ID NO 34
<211> LENGTH: 360
<212> TYPE: DNA
<213> ORGANISM: Caenorhabditis elegans
<220> FEATURE:
<221> NAME/KEY: misc_feature
<222> LOCATION: (303)..(303)
<223> OTHER INFORMATION: n is a or c or g or t or unknown

<400> SEQUENCE: 34
cgacgaaata gtgttttcac gaatagcgat gacgatgatg tggacgttca gttgaccgga     60
```

```
caagtcacgg aacatttgag gaatttgcag tgtagtaatg gttccgcaac ttccccatct    120
acatcagtgt cagcttcatc ttcttctgct cgtccactga caaatggaaa taatcatctt    180
tccacggcgt cgtctaccga cacatctctc tcattatcgg aaaggaataa cgttccgtct    240
ccagctccag ttccatatag tgaaagtgct ccacaactga aaacattcac cggagagact    300
ccnaaactgc atccacgatc tccgttcccg cctcaaccgc cagttcttcc gcaacgaagc    360
```

<210> SEQ ID NO 35
<211> LENGTH: 300
<212> TYPE: DNA
<213> ORGANISM: Caenorhabditis elegans
<220> FEATURE:
<221> NAME/KEY: misc_feature
<222> LOCATION: (33)..(33)
<223> OTHER INFORMATION: a or c or g or t or unknown
<220> FEATURE:
<221> NAME/KEY: misc_feature
<222> LOCATION: (131)..(131)
<223> OTHER INFORMATION: a or c or g or t or unknown

<400> SEQUENCE: 35

```
atgtttctgt atattttatg tgaaatgcaa cangaatctt ctagcaaaaa agtacgatgc     60
tggcaggtag ttgttggggg atggagagaa ggggagaaac aaaacaaaaa tgacaatagg    120
tgataaaaat nataataatg ttttcgccac agttttcgcg cttaattcac aggaaggttt    180 tttttttgcat acaataaaat agtgtgaatg ggagagattt ttagagagaa aaaaactaca    240
aaaaaaacga ggagcaagat ataagggctt gtgtatggta aaacatataa aacgctgtgt    300
```

<210> SEQ ID NO 36
<211> LENGTH: 750
<212> TYPE: DNA
<213> ORGANISM: Caenorhabditis elegans

<400> SEQUENCE: 36

```
atgaagccat cctcgtccgc aatggatatt agtcagccat ataacacagt gcatcgtctt     60
gccgatcaga agaaggatcc gaacgcggtg gtgactgcgt tgaagttcta cgcacaatca    120
atgaaggaga acgagaagac gaaattcatg acgacgaata gtgttttcac gaatagcgat    180
gacgatgatg tggacgttca gttgaccgga caagtcacgg aacatttgag gaatttgcag    240
tgtagtaatg gttccgcaac ttccccatct acatcagtgt cagcttcatc ttcttctgct    300
cgtccactga caaatggaaa taatcatctt tccacggcgt cgtctaccga cacatctctc    360
tcattatcgg aaaggaataa cgttccgtct ccagctccag ttccatatag tgaaagtgct    420
ccacaactga aaacattcac cggagagact ccaaaactgc atccacgatc tccgttcccg    480
cctcaaccgc cagttcttcc gcaacgaagc aaaaccgcat cggcagtggc gacgacgacg    540
acgaatccga cgacttcgaa tggagcacca ccaccagttc ctggatcgaa aggacccccg    600
gtgccaccga aaccatcgac ttcagttatc tcttttcgtg agtgttcact gatttgtgtt    660
ttgatttatg ttgttcgtca aatttgtaga tttgatcttc tcacttccaa gctcggtgca    720
cattgttcaa actctttgca attctggtag                                     750
```